US006235278B1

(12) United States Patent
Miller et al.

(10) Patent No.: US 6,235,278 B1
(45) Date of Patent: May 22, 2001

(54) BIOLOGICAL INSECT CONTROL AGENTS EXPRESSING INSECT-SPECIFIC TOXIN GENES, METHODS AND COMPOSITIONS

(75) Inventors: Lois K. Miller, Athens, GA (US); Albert Lu, Newark, DE (US); Bruce Christian Black; Peter Michael Dierks, both of Yardley, PA (US)

(73) Assignees: University of Georgia Research Foundation, Inc., Athens, GA (US); American Cyanamid Co.,, Madison, NJ (US)

( * ) Notice: Subject to any disclaimer, the term of this patent is extended or adjusted under 35 U.S.C. 154(b) by 0 days.

(21) Appl. No.: 08/942,012

(22) Filed: Oct. 1, 1997

Related U.S. Application Data

(63) Continuation-in-part of application No. 08/720,606, filed on Oct. 1, 1996, now abandoned.

(51) Int. Cl.[7] .................. A61K 48/00; C12N 15/866; C12N 15/63; C12N 7/01
(52) U.S. Cl. .................. 424/93.2; 424/93.6; 435/69.1; 435/320.1; 435/235.1; 435/455; 435/456; 536/23.1; 536/23.5; 536/24.1; 536/23.4
(58) Field of Search .................. 435/69.1, 172.1, 435/172.3, 320.1, 235.1, 455, 456; 536/23.1, 23.5, 24.1, 23.4; 424/93.2, 93.6

(56) References Cited

U.S. PATENT DOCUMENTS

| | | | |
|---|---|---|---|
| 5,004,687 | 4/1991 | Miller | 435/69.1 |
| 5,041,379 | * 8/1991 | Frasier et al. | 435/235.1 |
| 5,266,317 | 11/1993 | Tomalski | 424/93.2 |
| 5,643,776 | 7/1997 | Hammock | 435/196 |
| 5,965,123 | * 10/1999 | Ahmed | 424/93.2 |

FOREIGN PATENT DOCUMENTS

| | | |
|---|---|---|
| 0 505 207 A1 | 9/1992 | (EP) . |
| 0 697 170 A1 | 2/1996 | (EP) . |
| 92/06181 | 4/1992 | (WO) . |
| 94/28114 | 12/1994 | (WO) . |
| 96/03048 | 2/1996 | (WO) . |
| 97/08297 | 3/1997 | (WO) . |

OTHER PUBLICATIONS

Bonning, B.C., et al., "Superior expression of juvenile hormone esterase and β–galactosidase from the basic protein promoter of Autographa californica nuclear polydedrosis virus compared to the p10 protein and polyhedrin promoters" *J. General Virology* (1994) 75:1551–1556.

Clarke, E.E., et al., "Characterization of the ecdysteroid UDP–glucosyltransferase gene from Mamestra brassicae nucleopolyhedrovirus" *J. of General Virology* (1996) 77:2865–2871.

Hill–Perkins, M.S. and Possee, R.D., "A baculovirus expression vector derived from the basic protein promoter of Autographa californica nuclear polyhedrosis virus" *J. General Virology* (1990) 71:971–976.

Jarvis, D.L., et al., "Influence of different signal peptides and prosequences on expression and secretion of human tissue plasminogen activator in the baculovirus system" *J. Biological Chesmistry* (1993) 268(22):16754–16762.

Lu, A., et al., "Signal sequence and promoter effects on the efficacy of toxin–expressing baculoviruses as biopesticides" *bio. Control* (1996) 7:320–332.

McNitt, L., et al., "Assessing the safety of toxin–producing baculvirus biopesticides to a nontarget predator, the social wasp polistes metricus say" *Bio. Control* (1995) 5:267–278.

Morris, T.D. and Miller, L.K., "Promoter influence on baculovirus–mediated gene expression in permissive and nonpermissive insect cell lines" *J. Virology* (1992) 66(12):7397–7405.

O'Reilly, D.R., "Baculovirus–encoded ecdysteroid UDP–glucosyltransferases" *Insect Biochem. Molec. Biol.* (1995) 5:541–550.

O'Reilly, D.R., et al., "Overexpression of bombyx mori prothoracicotropic hormone using baculovirus vectors" *Insect Biochem. Molec. Biol.* (1995) 25(4):475–485.

O'Reilly, D.R., et al., "Characterization of the DA26 gene in a hyeprvariable region of the autographa californica nuclear polyhedrosis virus genome" *J. General Virology* (1990) 71:1029–1037.

Popham, J.J.R., et al., "Genetic improvement of helicoverpa zea nuclear polyhedrosis virus as a biopesticide"(1997) 10:83–91.

Stewart, L.M.D., et al., "Construction of an improved baculovirus insecticide containing an insect–specific toxin gene" *Nature* (1991) 352:85–88.

Thiem, S.M. and Miller, L.K. "Differential gene expression mediated by late, very late and hybrid baculovirus promoters" *Gene* (1990) 91:87–94.

(List continued on next page.)

*Primary Examiner*—David Guzo
(74) *Attorney, Agent, or Firm*—Greenlee Winner and Sullivan PC

(57) ABSTRACT

Provided herein are genetically engineered baculoviruses which express insect-specific toxins, preferably paralytic neurotoxins, under the regulatory control of strong promoters expressed early after infection and in a wide variety of insect cells. Particularly preferred insect-specific paralytic neurotoxins are those of insect-predacious mites, including Pyemotes. The genetically engineered baculoviruses of the present invention are improved over prior art viruses in that they produce efficacious insect-toxic levels of the neurotoxin at earlier times after infection, particularly in comparison to baculoviruses in which the toxin is expressed under the control of a polyhedrin or granulin promoter. Insect-toxic compositions are also provided and methods of insect control using these compositions are described.

27 Claims, 15 Drawing Sheets

OTHER PUBLICATIONS

Thiem, S.M. and Miller, L.K. "Identification, Sequence, and Transcriptional mapping of the major capsid protein gene of the baculovirus autographa californica nuclear polyhedrosis virus" *J. Virology* (1996) 63(5):2008–2018.

Todd, J.W., et al., *"Factors regulating baculovirus late and very late gene expression in transient–expression assays" J. Virology* (1995) 8(4):2307–2317.

Todd, J.W., et al, "Eighteen Baculovirus Genes, Including lef–11, p35, 39K and p47, support late gene expression" *J. Virology* (1995) 69(2):968–974.

Torok, I. and Katch, F., "Nucleotide sequences of heat shock activated genes in Drosophila melanogaster. I. Sequences in the regions of the 5' and 3' ends of the hsp 70 gene in the hybrid plasmid 56H8" *Nucleic Acids Research* (1980) 8(14):3106–3123.

Wilson, M.E., et al., "Location, transcription, and sequence of a baculovirus gene encoding a small arginine–rich polypetide" *J. Virology* (1987) 61(3):661–666.

Wang, X., et al., "Baculovirus vector for multiple gene expression and for eccluded virus production" *Gene* (1991) 100:131–137.

\* cited by examiner

FIG. 1A

```
ATG AAA ATT TGT ACA TTT TTT ATT CTT TTA TTC AAA ATG AAC TTG
 M   K   I   C   T   F   F   I   P   L   F   K   M   N   L
TTT TTT TTA TTT ATT CCA ACA ATT TTA GCA GTT AAA CCT TTT AGG TCT TTT AAT AAT ATT TCC TTA ATT GAT AAT GGC
 F   F   L   F   I   P   T   I   L   A   V   K   P   F   R   S   F   N   N   I   S   L   I   D   N   G
```
'c'

FIG. 1B

```
ATG AAC TTC CAA AAC ATA TTC ATA TTT GTG GCG TTA ATA TTC GTG GCG GGA CAA TCT CAG GCG GGG GAT AAT GGC
 M   N   F   Q   N   I   F   I   F   V   A   L   I   L   F   V   A   G   Q   S   Q   A   G   D   N   G
```

FIG. 1C

```
ATG TTC AAG TTT GTC ATG ATC TGC GCA GTT TTG GGC CTG GCG GTG GCC GAT AAT GGC
 M   F   K   F   V   M   I   C   A   V   L   G   L   A   V   A   D   N   G
```

'b'

```
ATG AAC TTG TAT TTT TTA TTT TTT ATT TCA ACT ATT TTA GCA GCT AAA CCT TTC AAT TCT TTT AAT AAA ACT TCA TTA ATT GAT AAT GGC
 M   N   L   Y   F   L   F   F   I   S   T   I   L   A   A   K   P   F   N   S   F   N   K   T   S   L   I   D   N   G
```

```
ATG AAA ATT TGT ACA TTT TTT ATT CTT TTA TTC AAA ATG AAC TTG
 M   K   I   C   T   F   F   I   L   L   F   K   M   N   L
TTT TTT TTA TTT ATT CCA ACA ATT TTA GCA GTT AAA CCT TTT AGG TCT TTT AAT AAT ATT TCC TTG ATT GAT AAT GGC
 F   F   L   F   I   P   T   I   L   A   V   K   P   F   R   S   F   N   N   I   S   L   I   D   N   G
```

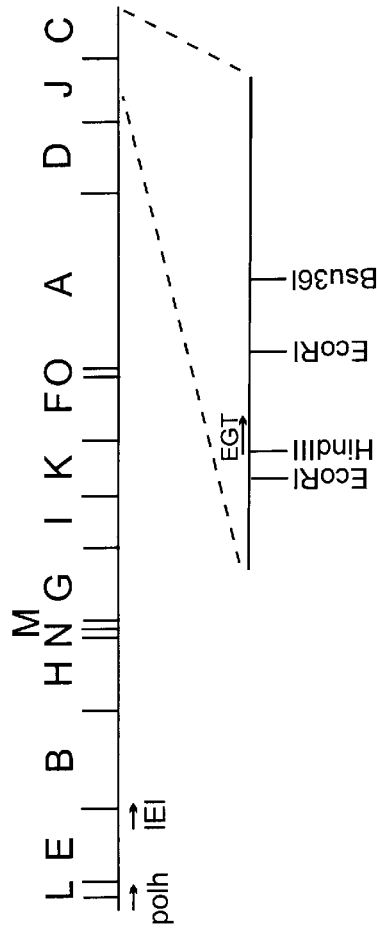

```
5'    1   CGATAACAAC TTTAAAGTAA CCATATTATG GAACACTTGA CCGCACACCC
     51   AAATAGAATG ACAAAGAATG TTTTCATCGT TTCGTCGCCC ACACAATTCA
    101   AACATAAACGT TATCTTTAAA GATAACAAAT GATGACATAT ATTAAATTAT
    151   GGTGCAATAT ACATGACACA AACAACTTAC GTCATCGTAA CCTTGAATTA
    201   AAATGTAAAA ACAATTGTG ATATCGTTAA TTCTAGGAAG TTGGGCACAA
    251   ACAACTTACG TCATCGTAAC CTTAGGTCAA ATCGTTAATT CTAGGAAGTT
                            Bsu36I
    301   GTGCACAAAC AACTTACGTC ATACATGTTA TTAATCATTT GCGGTGCAAT
    351   CGTCATCGGA TCAAACGATT TCGGTTAAAT TTCGACACTG GTGTG 3'
```

```
   1 TCGACAGAGTTATATTATTTATTAATGTGTTGCTGTTGTTGCGTATGACATCATAGGTAT

61 TAGTACTGTCATTGCTAAATATAGACATGAAATAATTATCTTCGTTGAGGTTATCACGAA

121 CACTAGTAGTCATCGTGACGATAGATATCTGTAATACACACATCAAAGTAAACATGTTTA

181 CTTAAACAGTAACTGAATAATAATTTCAACATAGCTACGCCACTATAAGATGCAGCATCC

241 CGTCCGTTCGTCATCTTTCGATAAACGCTCTGACCCATAAACGGACGTGCGCTAATTTTT

301 TTTTATTGCTAAATTCAAAATGTACAAACAAATAATAACTATGTTATTGTTGGTGTTGTT
                       M  Y  K  Q  I  I  T  M  L  L  V  L  F

361 TCTGTCGGTTCTGGATGGAGCGCGTATCCTGTGCGTTTTTCCTGTTCCTTCGTACAGTCA
      L  S  V  L  D  G  A  R  I  L  C  V  F  P  V  P  S  Y  S  H

421 TCATGCAGTGTTCGAAGCTTACACCAATGCTCTAGCGTCGCGTGGCCATACAATAGTCAG
      H  A  V  F  E  A  Y  T  N  A  L  A  S  R  G  H  T  I  V  R

481 AATTACACCGTTTCCCACTAAGAAAAACGATTCATCCAACGTGACAGATGTCGACGTTAG
      I  T  P  F  P  T  K  K  N  D  S  S  N  V  T  D  V  D  V  S

541 CTTGTCGAAAGATTATTTTAAAAGTCTTGTGGACCGATCTAGACTGTTCAAGAAACGAGG
      L  S  K  D  Y  F  K  S  L  V  D  R  S  R  L  F  K  K  R  G

601 CGTTATTTCGGAAACGTCCAGCGTGACCGCTCGCAATTACATCAGTCTAGTACACATGTT
      V  I  S  E  T  S  S  V  T  A  R  N  Y  I  S  L  V  H  M  L

661 GATTGATCAATTCTCTGTGGAGAGTCTACGACAATTGATCGAATCCAACAATGTTTTCGA
      I  D  Q  F  S  V  E  S  V  R  Q  L  I  E  S  N  N  V  F  D

721 TTTGTTGGTGACCGAAGCCTTTCTAGATTATCCTCTGGTGTTTTCGCATTTGTTTGGCGA
      L  L  V  T  E  A  F  L  D  Y  P  L  V  F  S  H  L  F  G  D

781 TGTGCCTGTCATACAAATTTCGTCGGGTCACGCTTTGGCCGAAAATTTTGAGACAATGGG
      V  P  V  I  Q  I  S  S  G  H  A  L  A  E  N  F  E  T  M  G

841 AGCCGTGAGCCGACATCCCATTTACTATCCAAATTTGTGGCGCAACAAATTTCAAAATTT
      A  V  S  R  H  P  I  Y  Y  P  N  L  W  R  N  K  F  Q  N  L

901 AAACGTTTGGGAGATAATAACGGAAATCTATACAGAACTGGTGCTGTACTTGGAATTTGC
      N  V  W  E  I  I  T  E  I  Y  T  E  L  V  L  Y  L  E  F  A

961 TCGTTTAGCCGACGAACAAACTAAAATGCTTCGCCATCAATTCGGACCAAACACGCCCAG
      R  L  A  D  E  Q  T  K  M  L  R  H  Q  F  G  P  N  T  P  S

1021 CGTGGAAGAACTGCGACAACGCGTTCAATTATTGTTTGTGAATACGCATCCGCTGTTTGA
      V  E  E  L  R  Q  R  V  Q  L  L  F  V  N  T  H  P  L  F  D

1081 TAATAACAGACCAGTACCGCCGAGTGTACAATATTTGGGAAGTCTACATCTTGATCGAAA
      N  N  R  P  V  P  P  S  V  Q  Y  L  G  S  L  H  L  D  R  N
```

FIG. 10A

```
1141 CAATGATGTCGACGAACAGCAAACGATGGACTATAATTTGATGCAATTTTTAAATAATTC
      N   D   V   D   E   Q   Q   T   M   D   Y   N   L   M   Q   F   L   N   N   S

1201 TACAAACGGTGTGGTGTACGTGAGCTTCGGTACGTCTATACGAGTTTCAGACATGGACGA
      T   N   G   V   V   Y   V   S   F   G   T   S   I   R   V   S   D   M   D   D

1261 CGAATTTCTGTTTGAATTTATAACAGCTTTCAAGCAATTACCCTATAATATATTGTGGAA
      E   F   L   F   E   F   I   T   A   F   K   Q   L   P   Y   N   I   L   W   K

1321 GACCGATGGAATGCCCATGGAACACGTACTGCCTAAAAATGTGTTGACACAAACTTGGCT
      T   D   G   M   P   M   E   H   V   L   P   K   N   V   L   T   Q   T   W   L

1381 GCCGCAACACCATGTATTGAAACACAGCAATGTAGTTGCTTTTGTTACTCAAGGCGGAAT
      P   Q   H   H   V   L   K   H   S   N   V   V   A   F   V   T   Q   G   G   M

1441 GCAGTCAACGGACGAAGCCATCGACGCTTGTGTACCACTAATCGGAATCCCGTTTATGGG
      Q   S   T   D   E   A   I   D   A   C   V   P   L   I   G   I   P   F   M   G

1501 CGACCAAGCATACAATACCAATAAATACGAAGAACTCGGAATCGGACGCAACCTCGATCC
      D   Q   A   Y   N   T   N   K   Y   E   E   L   G   I   G   R   N   L   D   P

1561 CGTAACGCTCACAAGTCATATTTTGGTGTCTGCCGTTTTAGATGTCACCGTCAACAACAA
      V   T   L   T   S   H   I   L   V   S   A   V   L   D   V   T   V   N   N   K

1621 GAGTCGCTACACAGATAATATTAAAGCATTGAATCGTTCCACTAATTATCGAACACGGAA
      S   R   Y   T   D   N   I   K   A   L   N   R   S   T   N   Y   R   T   R   K

1681 ACCTATGGAAAAGGCCATCTGGTACACAGAACATGTAATTGATAATGGTAAAAATCCCAT
      P   M   E   K   A   I   W   Y   T   E   H   V   I   D   N   G   K   N   P   I

1741 TTTAAAAACGAAGGCCGCCAACGTATCGTATAGCAAATATTATATGAGTGATATCATCGT
      L   K   T   K   A   A   N   V   S   Y   S   K   Y   Y   M   S   D   I   I   V

1801 TCCTGTTATAACGTTTTTGGTAATGACTCATTTGGGTCAGGCTATTCGGCGGTTGGTTGT
      P   V   I   T   F   L   V   M   T   H   L   G   Q   A   I   R   R   L   V   V

1861 TATTTAATACTGTATGACAATGTACACATGTGTTAATAAAAAAGGCATTACTAATATTTA
      I   *

1921 GATTGTTTCAAATTATTTACGCATGACTACCCGTCTCCTATTGCGCAGCTACGCTAGCTT

1981 TAAATACAGCCGATGGCGTAGTAAAGTTCATTTAAATATCTAAAT
```

FIG. 10B

```
HzNPV    1  ..........MYKQIITMLLLVLFLSVL...DGARILCVFPVPSYSHHAVFEAYTNALA
MbNPV    1  MGHLHIVHWRLTMNGAIAALFLCLVMVH..QQHAVRILAVFPTPSYSHHSVFKVYIEALA
LdNPV    1  ................MTAYLIVFCLCCWSAARSANILAYFPTPSYSHQLVFRAYVELLA
S1NPV    1  ................MKMLILVVSLHVLRNSAAVRVLCHFPTPSYSHQTVFDVYVNALL
AcNPV    1  ................MTILCWLALLSTLTAVNAANILAVFPTPAYSHHIVYKVYIEALA
BmNPV    1  ................MTILCWLALLSTLTAVNAVNILAVFPTPAYSHHIVYKVYIEALA
CfNPV    1  ................MASLLIALTLLAADAQTANILAVLPTPAYSHHAVYKAYVHALA
CfDEF    1  ................MIFILLTTLLAVGGAQTANILAVLPTPAYSHHLVYQAYVQALA
OpNPV    1  ................MVFLIIALTLIATGARAASILAVLPTPAYSHHVVYRAYVHALV
LoGV     1  ................MFISILLLALAVERILCANILCVFPTPAYSHQSVFSAYIDKLS

HzNPV   47  SRGHTIVRITPFPTKKNDS......SNVTDVDV.SLSKDYFKSLVDRSRLFKKRGVISET
MbNPV   59  ERGHDVVVIKS.TDRINYANRNGLRGNVSEID.ASLSQEYYGRLMRHAGVFRKRGIVADS
LdNPV   45  ERGHAVTVIRP.LTRVDF.NRNA..GNLTTID...LDGDGLLLLMKASTTHRKRGIVADT
S1NPV   45  RRGHSLVVISPKIHNHNHGHRHHRHENLTEIDVGSVTNNFEKRLLQDSKVSRKRGIVSDS
AcNPV   45  EKCHNVTVVKPKLFAYS..TK.TYCGNITEIN.ADMSVEQYKKLVANSAMFRKRGVVSDT
BmNPV   45  EKCHNVTVVKPKLFAYS..TK.TYCGNITEVN.SDMSVKQYKKLVTNSAMFRKRGVVSDT
CfNPV   44  KNCHNVTAVKPRLLDYALLNE...CGRIEQID.ADMSLEQYQKLMAGSGAFRKRGVVADE
CfDEF   44  DKCHNVTVVKPQLLDYAAANK.QRCGRIEQID.ADMSSQQYKKLVASSGAFRKRGVVSDE
OpNPV   44  KNCHNVTVIKPQLLDYAVQDE...CGRVEQID.ADMSAQQYKKLVASSGVFRKRGVVADE
LoGV    44  WAGHNVTVITPMPRAVDHVHQV.........VSSLSVHYFNNLIKNSTMIKKRGVVADE

HzNPV  100  SSVTARNYISLVHMLIDQFSVESVRQLIES..NNVFDLLVTEAFLDYPLVFSHLFGDVPV
MbNPV  117  STVTAHNYMGLVRMMSDQFDLPIVKSFIEEAHKHKFDLLITEAYIDYPLVFSHLFGDLPV
LdNPV   98  DTVTADNYEALVRMVDRQIHSEPFQRHLKSA.RRGYDLLVVEAFVDYALIASHLFGDVPV
S1NPV  105  STVTRVNYLGLARMISAQFEHEQVKRLLRS..NQTFDVIVIEAFVSYPLILSYFFKDTPV
AcNPV  101  DTVTAANYLGLIEMFKDQFDNINVRNLI..ANNQTFDLVVVEAFADYALVFGHLYDPAPV
BmNPV  101  DTVTAANYLGLIEMFKDQFDNINVRNLI..ANNQTFDLVVVEAFADYALVFGHLYDPAPV
CfNPV  100  TTVTADNYMSLIEMFKDQFDNANVRHFL..ASNRTFDAVVVEASADYELVFGHLFRPATV
CfDEF  102  TTVTAENYMGLVEMFRDQFDNAHVRSFL..ATNRTFDVVVVEAFADYALVFGHLFRPAPV
OpNPV  100  TTVTADNYMGLIEMFKDQFDNANVRRFL..STNRTFDAVVVEAFADYALVFGHLFRPAPV
LoGV    94  TTVTKENYMGLINLVAHEIKSPNVTRLLRNKGNK.FDLIVCEAYVSYILVFGAIY.DAPV

HzNPV  158  IQISSGHALAENFETMGA.VSRHPIYYPNLWRNKFQNLNVWEIITEIYTELVLYLEFARL
MbNPV  177  VQISSGYAVAENFETMGA.VSRHPVYYPNLWRDKFSGLNVWKQSMKCTLSWRYRMNLVNW
LdNPV  157  VQISSGHATAENFETMGA.TSRHPRYYPNLWRFNFGPLSVWDGVRELYTELRLQREFGLL
S1NPV  163  IQISSGHGTAENFETMGA.VARHPVYYPNMWRDRFKGLSVWQTVRQVFTEIRLYMEFSQL
AcNPV  159  IQIAPGYGLAENFDTVGA.VARHPVHHPNIWRSNFDD.....TEANVMTEMRLYKEFKIL
BmNPV  159  IQIAPGYGLAENFDTVGA.VARHPVHHPNIWRNNFDD.....TKANLMTEMRLYKEFKIL
CfNPV  158  IQIAPGYGLAENFDAAGA.VARHPVHYPNIWRSSFSG.....EAAGALSEWRLLNEFELL
CfDEF  160  IQIAPGYGLAENFDAVGA.VGRHPVHYPNIWRSSSIG.....NADGALIEWRLYNEFELL
OpNPV  158  IQIAPGYGLAENFERRRA.VARHPLHYPTFGAAAL.T.....RRGGALSEWRLLNEFELL
LoGV   152  IQFSSGYAIPENFETVGGEVARNHIKHPNIWRSDFSKSNF....EQLMTENYLKNEWALL

HzNPV  217  ADEQ.TKMLRHQFGPNTPSVEELRQRVQLLFVNTHPLFDNNRPVPPSVQYL.GSLHLDRN
MbNPV  236  PDEQ.NALLKRQFGESTPTIQELRNRVELLFVNTHAIFDNNRPVPPSVQYL.GALHLHDK
LdNPV  216  ADRQ.DALLKRRFGPEAPGLRELRSRVRLLFVNVHSVFDNNRPVPPSVQYL.GGLHLHDR
S1NPV  222  DADQ.SAMMKRQFGSKVPDVDALRKNVHMMFVNTHPVFDTNRPVPSNVQYL.GGIHIDPA
AcNPV  213  A.NMSNALLKQQFGPNTPTIEKLRNKVQLLLLNLHPIFDNNRPVPPSVQYLGGGIHLVKS
BmNPV  213  A.NMSNALLKQQFGPDTPTIEELRNKVQLLLLNLHPIFDNNRPVSPSVQYLGGGIHLVKS
CfNPV  212  ASQRSNELLKQQFGLDTPTIRQLRDNVQLLLLNLHPVYDNNRPVPPSVQYLGGGLHLSQA
CfDEF  214  A.RRSDALLKLQFGPNTPTIRQLRNNVQLLLLNLHPVYDNNRPVPPSVQYLGGGLHLTLE
OpNPV  211  A.RRSDELLKQQFGKSTPTIRQLRDNVQLLLLNLHPVYDNNRPVPPSVQYLGGGLHLAQA
LoGV   208  EKEQEN.MLKRDFGYH.HDMCQLKSRVLMLFINVPAVFDNNRDVSNNIQYL.GGIHLKKP
```

FIG. 11B

```
HzNPV  275 NDVDEQQTMDYNLMQFLNNSTNGVVYVSFGTSIRVSDMDDEFLFEFITAFKQLP.YNILW
MbNPV  294 RP....DSMYGMVREFLDNATTGAIYVSFGSAISSEDMEPEFIEMLLRVFEKLP.YSILW
LdNPV  274 RA....EPLSEAVARFLDESRRGVVYVSFGSGLATEDMDADMAAALLDAFKMMP.YDVLW
S1NPV  280 VTSVADE.IDNDLAEFLENSTMGVVYVSLGSSVRASDMDSNMLNVFVETFRSIP.YRVLW
AcNPV  272 APL...TKLSPVINAQMNKSKSGTIYVSFGSSIDTKSFANEFLYMLINTFKTLDNYTILW
BmNPV  272 APL...TKLSPVIDAKMNKSKSGAIYVSFGSSIDTKSFANEFFYMLINTFKALDNYTILW
CfNPV  272 PS....HKLTAALERRLNESVDGAIYVSFGSSIDTNSIHAEFIQMLLESFVQLNNYTVLW
CfDEF  273 PP....QRLDIELEKRLNASVNGTVYVSFGSSIDTNSIHAEFLEMLLDTFAKLDNRTVLW
OpNPV  270 LP....QRLDAPLERRLNESVDGAVYVS................................
LoGV   265 RTVRDSRLLS......FMEKHHIIVYASFGSGIDVLNMDANLIAEFVRVFNSIP.YAVLW

HzNPV  334 KTD.GMPMEHVLPKNVLTQTWLPQHHVLKHSNVVAFVTQGGMQSTDEAIDACVPLIGIPF
MbNPV  349 KYDGYMNRM...PANVFVQSWFEQYNLLHHKNVRAFVTQGGVQSTDEAVEAIVPMVGMPM
LdNPV  329 KHDGRVDGL.TIPANVFVQKWFAQFEVLQHKNVKAFVTQAGVQSTDEAVENLVPDVGVPL
S1NPV  338 KVDKSDKIFDNIPSNVLIQRWFPQRRVLKHRNVKVFITQGGVQSTDEAIDAGVPMFGVPI
AcNPV  329 KIDDEVVKNITLPANVITQNWFNQRAVLRHKKMAAFITQGGLQSSDEALEAGIPMVCLPM
BmNPV  329 KIDDEVVKNITLPANVITQNWFNQRAVLRHKKMAAFITQGGLQSSDEALEAGIPMVCLPM
CfNPV  328 KVDDTVPASVKLPSNVVTQKWFDQRAVLHHKKVVAFVMQAGLQSSDEALESRVPMVCLPM
CfDEF  329 KVDDAVAKSVVLPRNVIAQKWFNQRAVLNHRNVVAFVTQGGLQSSDEALHARVPMVCLPM
OpNPV      ............................................................
LoGV   318 KVDSSIHLKHNISSNVHTQSWFPQRDVLNHPHIKVFITQGGVQSTDEAVNSGVPMIGIPI

HzNPV  393 MGDQAYNTNKYEELGIGRNLDPVTLTSHILVSAVLDVTVNNKSRYTDNIKALNRSTNYR.
MbNPV  406 MGDQAYNMNKIVELGLGKVVDTVRVNAEQLIEAIVDVAESPK..YRKRLRELRHMIHHQ.
LdNPV  388 MGDQAFNAHRYVELGIGVALDATRLTAADLARAVEQVTSDRA..YRENLERLRRLLRHQ.
S1NPV  398 MGDQFYNVYMYETYGIGRGVDTLTVDARQLTEIVMDVADNEK..YKNGTLWLRDAIMDQ.
AcNPV  389 MGDQFYHAHKLQQLGVARALDTVTVSSDQLLVAINDVLFN.APTYKKHMAELYALINHDK
BmNPV  389 MGDQFYHAHKLQQLGVARALDTVTVSSDQLLLAINDVLFN.ASTYKKHMAELYALINNDK
CfNPV  388 MGDQFHHARKLQQFGVARTLDTAVVSAAQLTLAIGEVIAD.AEAYRARIDDLRAVLE.HD
CfDEF  389 MGDQFHHSAKLEQFGVARALNTVTVSAAQLALAVGDVIAI.RLAYQLRMTNLLNVVAFDE
OpNPV      ............................................................
LoGV   378 MGDQFYNVRRYTELGIGEKVNILRLEEEGLDRKIKNLVHNKS..YELNIKRLNLFIS..D

HzNPV  452 .TRKPMEKAIWYTEHVI...DNGKNPI..LKTKAANVSYSKYYMSDIIVPVITFLVMTHL
MbNPV  463 .PMTPLQKAVWYTEHVIESRRRVVPTM..LKTRAANVNYSDYIMSYVFVPFIMFTVMNHL
LdNPV  445 .CASPTHKAVWYTEHAL....RRDGDA..LKTKAANVDYAEYCMSTCWRPC.........
S1NPV  455 .PMRPLEKAVWYTEHVA..RRKGAKKH..LGTRAANVTYSKYAMFDLILP....MLITIF
AcNPV  448 ATFPPLDKAIKFTERVIRYRHDISRQLYSLKTTAANVPYSNYYMYKSVFSIVMNHLTHF.
BmNPV  448 ATFPPLDKAIKFTERVIRYRHDISRRLYSLKTTAANVPYSNYYMYKSVLSIVMNHIAHF.
CfNPV  446 AA..PAEKAVKFTERVIIFKHDMTRPARTLKTTSANIAYSDYELRFPL............
CfDEF  448 AT..PADKAIKFTERVIREGHDITRSECSLKSPSANTDYSDYFVRFPL............
OpNPV      ............................................................
LoGV   434 TPVKPLRKALWFTNYVLRNKDAIDFK..................................

HzNPV  506 GQAIRRLVVI
MbNPV  520 RQLLKMNMV.
LdNPV      ..........
S1NPV  506 STYLQKILSI
AcNPV      ..........
BmNPV      ..........
CfNPV      ..........
CfDEF      ..........
OpNPV      ..........
LoGV       ..........
```

FIG. 11C

SEQUENCE LISTING

<160> NUMBER OF SEQ ID NOS: 33

<210> SEQ ID NO 1
<211> LENGTH: 917
<212> TYPE: DNA
<213> ORGANISM: Pyemotes tritici
<220> FEATURE:
<221> NAME/KEY: CDS
<222> LOCATION: (12)..(884)
<221> NAME/KEY: mat_peptide
<222> LOCATION: (129)..(884)

<400> SEQUENCE: 1

```
cttattaatt a atg aaa att tgt aca ttt ttt att cct tta ttc aaa atg        50
           Met Lys Ile Cys Thr Phe Phe Ile Pro Leu Phe Lys Met
               -35                 -30 aac ttg ttt ttt tta ttt att att cca aca att tta gca gtt aaa cct        98
Asn Leu Phe Phe Leu Phe Ile Ile Pro Thr Ile Leu Ala Val Lys Pro
    -25                 -20                 -15 ttt agg tct ttt aat aat att tcc tta att gat aat ggc aat gtc gaa       146
Phe Arg Ser Phe Asn Asn Ile Ser Leu Ile Asp Asn Gly Asn Val Glu
-10                  -5              -1   1                   5 tct gta aga gca gta gtt att gat tat tgt gat att aga cat cca aat       194
Ser Val Arg Ala Val Val Ile Asp Tyr Cys Asp Ile Arg His Pro Asn
                10                  15                  20 aat tta tgt aaa aaa cat ttt gaa atc gat tca tat tgg aat gat gat       242
Asn Leu Cys Lys Lys His Phe Glu Ile Asp Ser Tyr Trp Asn Asp Asp
            25                  30                  35 acg gat tgt ttt aca aat att gga tgc aaa gta tat gga gga ttt gat       290
Thr Asp Cys Phe Thr Asn Ile Gly Cys Lys Val Tyr Gly Gly Phe Asp
        40                  45                  50 att att ggt ggt cat acc cct aaa gtt gga act gta tgt aga ctt aaa       338
Ile Ile Gly Gly His Thr Pro Lys Val Gly Thr Val Cys Arg Leu Lys
55                  60                  65                  70 aaa gga gaa aat aaa ttt gga tat tgt aat tca aag gga aat tgc gtt       386
Lys Gly Glu Asn Lys Phe Gly Tyr Cys Asn Ser Lys Gly Asn Cys Val
                75                  80                  85 gaa aga gat ttt aaa gaa agt ttt gga ata tct ata aaa ata aaa gga       434
Glu Arg Asp Phe Lys Glu Ser Phe Gly Ile Ser Ile Lys Ile Lys Gly
            90                  95                  100 att tct aat aaa gga gat gat gaa cca gca tgt cca caa tat aaa aat       482
Ile Ser Asn Lys Gly Asp Asp Glu Pro Ala Cys Pro Gln Tyr Lys Asn
        105                 110                 115 act tgg att aat tat ggg aaa tgt aat gaa cct tat tat tgt gga aca       530
Thr Trp Ile Asn Tyr Gly Lys Cys Asn Glu Pro Tyr Tyr Cys Gly Thr
120                 125                 130
```

```
aat cat gga tta ttt tat gca aac aaa aga aaa ctc gat tac ttt ccc    578
Asn His Gly Leu Phe Tyr Ala Asn Lys Arg Lys Leu Asp Tyr Phe Pro
135                 140                 145                 150 aca gac ggt gaa aaa tgt aat tca aat aat ata cca tat gct gtt tgt    626
Thr Asp Gly Glu Lys Cys Asn Ser Asn Asn Ile Pro Tyr Ala Val Cys
                155                 160                 165 tat tta gga aga tgt cat aca aca ggt ggt ttt ttt agt gaa ttt gga    674
Tyr Leu Gly Arg Cys His Thr Thr Gly Gly Phe Phe Ser Glu Phe Gly
            170                 175                 180 act att gtt aaa aat gtc gaa atc gta act tta tca gat gga aag aac    722
Thr Ile Val Lys Asn Val Glu Ile Val Thr Leu Ser Asp Gly Lys Asn
        185                 190                 195 agt tct aga aga gga aaa cat aaa aat tta cct act tct aaa gta ttt    770
Ser Ser Arg Arg Gly Lys His Lys Asn Leu Pro Thr Ser Lys Val Phe
    200                 205                 210 gat agt tat agt ata tat gat att gat cct aaa aat tgg aaa att gaa    818
Asp Ser Tyr Ser Ile Tyr Asp Ile Asp Pro Lys Asn Trp Lys Ile Glu
215                 220                 225                 230 gat gat gat aaa gat gtt act gtt cat gaa aat aca tta gat cca aaa    866
Asp Asp Asp Lys Asp Val Thr Val His Glu Asn Thr Leu Asp Pro Lys
                235                 240                 245 agt gat tca aga ctg tgt taaattttta aaaatttgat tttttaaat aaa        917
Ser Asp Ser Arg Leu Cys
            250

<210> SEQ ID NO 2
<211> LENGTH: 291
<212> TYPE: PRT
<213> ORGANISM: Pyemotes tritici

<400> SEQUENCE: 2

Met Lys Ile Cys Thr Phe Phe Ile Pro Leu Phe Lys Met Asn Leu Phe
                -35                 -30                 -25

Phe Leu Phe Ile Ile Pro Thr Ile Leu Ala Val Lys Pro Phe Arg Ser
            -20                 -15                 -10

Phe Asn Asn Ile Ser Leu Ile Asp Asn Gly Asn Val Glu Ser Val Arg
        -5                  -1  1                   5

Ala Val Val Ile Asp Tyr Cys Asp Ile Arg His Pro Asn Asn Leu Cys
 10                  15                  20                  25

Lys Lys His Phe Glu Ile Asp Ser Tyr Trp Asn Asp Thr Asp Cys
                 30                  35                  40

Phe Thr Asn Ile Gly Cys Lys Val Tyr Gly Phe Asp Ile Ile Gly
             45                  50                  55

Gly His Thr Pro Lys Val Gly Thr Val Cys Arg Leu Lys Lys Gly Glu
         60                  65                  70

Asn Lys Phe Gly Tyr Cys Asn Ser Lys Gly Asn Cys Val Glu Arg Asp
     75                  80                  85

Phe Lys Glu Ser Phe Gly Ile Ser Ile Lys Ile Lys Gly Ile Ser Asn
 90                  95                 100                 105

Lys Gly Asp Asp Glu Pro Ala Cys Pro Gln Tyr Lys Asn Thr Trp Ile
                110                 115                 120

Asn Tyr Gly Lys Cys Asn Glu Pro Tyr Tyr Cys Gly Thr Asn His Gly
            125                 130                 135

Leu Phe Tyr Ala Asn Lys Arg Lys Leu Asp Tyr Phe Pro Thr Asp Gly
        140                 145                 150

Glu Lys Cys Asn Ser Asn Asn Ile Pro Tyr Ala Val Cys Tyr Leu Gly
    155                 160                 165
```

```
Arg Cys His Thr Thr Gly Gly Phe Phe Ser Glu Phe Gly Thr Ile Val
170                 175                 180                 185

Lys Asn Val Glu Ile Val Thr Leu Ser Asp Gly Lys Asn Ser Ser Arg
            190                 195                 200

Arg Gly Lys His Lys Asn Leu Pro Thr Ser Lys Val Phe Asp Ser Tyr
                205                 210                 215

Ser Ile Tyr Asp Ile Asp Pro Lys Asn Trp Lys Ile Glu Asp Asp Asp
            220                 225                 230

Lys Asp Val Thr Val His Glu Asn Thr Leu Asp Pro Lys Ser Asp Ser
        235                 240                 245

Arg Leu Cys
250

<210> SEQ ID NO 3
<211> LENGTH: 1241
<212> TYPE: DNA
<213> ORGANISM: Pyemotes tritici
<220> FEATURE:
<221> NAME/KEY: CDS
<222> LOCATION: (119)..(985)

<400> SEQUENCE: 3
gaattccaac aacagtgcct ttgggcggcc gcactggtct taacttttt ctctttttta      60 gcagcggcca tgataattta ataatcttat ttacaaattt tttattattt tattcaga    118 atg aac ttg tat ttt tta ttt ttt att tca act att tta gca gct aaa     166
Met Asn Leu Tyr Phe Leu Phe Phe Ile Ser Thr Ile Leu Ala Ala Lys
 1               5                  10                  15 cct ttc aat tct ttt aat aaa act tca tta att gat gaa gga gtt gac     214
Pro Phe Asn Ser Phe Asn Lys Thr Ser Leu Ile Asp Glu Gly Val Asp
             20                  25                  30 aac gat gac gat att gtc tct aaa aga gca gta gtt att gat tat tgt     262
Asn Asp Asp Asp Ile Val Ser Lys Arg Ala Val Val Ile Asp Tyr Cys
         35                  40                  45 gat act aga cat cca aat aat tta tgt aaa aaa tat ttt gaa atc gat     310
Asp Thr Arg His Pro Asn Asn Leu Cys Lys Lys Tyr Phe Glu Ile Asp
     50                  55                  60 tca tat tgg aat gat gat acg gat tgt ttt aca aat att gga tgc aaa     358
Ser Tyr Trp Asn Asp Asp Thr Asp Cys Phe Thr Asn Ile Gly Cys Lys
 65                  70                  75                  80 gta tat gga gga ttt gat att att ggt ggt aaa gct cct aaa att gga     406
Val Tyr Gly Gly Phe Asp Ile Ile Gly Gly Lys Ala Pro Lys Ile Gly
                 85                  90                  95 act gta tgt aga ctt aaa aaa gga aaa aat aaa ttt gga tat tgt aat     454
Thr Val Cys Arg Leu Lys Lys Gly Lys Asn Lys Phe Gly Tyr Cys Asn
            100                 105                 110 tca aaa gga aat tgc gtt gaa aga gat ttt att gaa agt ttt gga gta     502
Ser Lys Gly Asn Cys Val Glu Arg Asp Phe Ile Glu Ser Phe Gly Val
        115                 120                 125 tct ata aaa ata aaa gga att tct cat aga gga gat gat gaa cca gca     550
Ser Ile Lys Ile Lys Gly Ile Ser His Arg Gly Asp Asp Glu Pro Ala
    130                 135                 140 tgt cca ctt tat gaa aat act tgg att aat tat gga aaa tgt aat gaa     598
Cys Pro Leu Tyr Glu Asn Thr Trp Ile Asn Tyr Gly Lys Cys Asn Glu
145                 150                 155                 160 cct tat cat tgt gga aca aat tat ggg tta ttt tat gca aac aaa aga     646
Pro Tyr His Cys Gly Thr Asn Tyr Gly Leu Phe Tyr Ala Asn Lys Arg
                165                 170                 175
```

```
aaa ctc aat tac ttt cct gat aac ggt caa aaa tgt aat tca aaa tat      694
Lys Leu Asn Tyr Phe Pro Asp Asn Gly Gln Lys Cys Asn Ser Lys Tyr
        180                 185                 190 gaa ata tac ggt gta tgt tat tta gga cgc tgt cat gga aca gga aat      742
Glu Ile Tyr Gly Val Cys Tyr Leu Gly Arg Cys His Gly Thr Gly Asn
            195                 200                 205 ttt tca aat ggt gaa gtt ttt agt gaa ttt gga act att ttt aaa gat      790
Phe Ser Asn Gly Glu Val Phe Ser Glu Phe Gly Thr Ile Phe Lys Asp
        210                 215                 220 gtc gaa att gta act tta tca gat gga aag aac agt tct aaa aga gga      838
Val Glu Ile Val Thr Leu Ser Asp Gly Lys Asn Ser Ser Lys Arg Gly
225                 230                 235                 240 aaa cat aaa aat tta cat ggt tct aaa gta ttt gat agt aat ggt ata      886
Lys His Lys Asn Leu His Gly Ser Lys Val Phe Asp Ser Asn Gly Ile
            245                 250                 255 tat gat att gat cct aaa aat tgg aaa att gaa gat gat gat aaa gat      934
Tyr Asp Ile Asp Pro Lys Asn Trp Lys Ile Glu Asp Asp Asp Lys Asp
        260                 265                 270 att act gtt cat gaa aat gct gga gat cca aaa agt gat tca aga cgt      982
Ile Thr Val His Glu Asn Ala Gly Asp Pro Lys Ser Asp Ser Arg Arg
            275                 280                 285 tgt taaatttta aatatttgat tttttttaaa taaatataaa tctatatatt           1035
Cys taataatata atttctttta atttttaaat tagtaaaatt tcgataattt tacttaattt    1095
tttaaattta ctaaattgac taatttttatt aagaagtaac ttctaaaaaa tttgattttt   1155
tttaaaacaa ataattataa atatttttta attaaataaa tttaataatt acaagataaa    1215
aaaaaaaaaa aaaaaaaaag gaattc                                         1241

<210> SEQ ID NO 4
<211> LENGTH: 289
<212> TYPE: PRT
<213> ORGANISM: Pyemotes tritici

<400> SEQUENCE: 4

Met Asn Leu Tyr Phe Leu Phe Phe Ile Ser Thr Ile Leu Ala Ala Lys
1               5                   10                  15

Pro Phe Asn Ser Phe Asn Lys Thr Ser Leu Ile Asp Glu Gly Val Asp
            20                  25                  30

Asn Asp Asp Asp Ile Val Ser Lys Arg Ala Val Val Ile Asp Tyr Cys
        35                  40                  45

Asp Thr Arg His Pro Asn Asn Leu Cys Lys Lys Tyr Phe Glu Ile Asp
    50                  55                  60

Ser Tyr Trp Asn Asp Asp Thr Asp Cys Phe Thr Asn Ile Gly Cys Lys
65                  70                  75                  80

Val Tyr Gly Gly Phe Asp Ile Ile Gly Gly Lys Ala Pro Lys Ile Gly
                85                  90                  95

Thr Val Cys Arg Leu Lys Lys Gly Lys Asn Lys Phe Gly Tyr Cys Asn
            100                 105                 110

Ser Lys Gly Asn Cys Val Glu Arg Asp Phe Ile Glu Ser Phe Gly Val
        115                 120                 125

Ser Ile Lys Ile Lys Gly Ile Ser His Arg Gly Asp Asp Glu Pro Ala
    130                 135                 140

Cys Pro Leu Tyr Glu Asn Thr Trp Ile Asn Tyr Gly Lys Cys Asn Glu
145                 150                 155                 160

Pro Tyr His Cys Gly Thr Asn Tyr Gly Leu Phe Tyr Ala Asn Lys Arg
                165                 170                 175
```

-continued

```
Lys Leu Asn Tyr Phe Pro Asp Asn Gly Gln Lys Cys Asn Ser Lys Tyr
            180                 185                 190
Glu Ile Tyr Gly Val Cys Tyr Leu Arg Cys His Gly Thr Gly Asn
        195                 200                 205
Phe Ser Asn Gly Glu Val Phe Ser Glu Phe Gly Thr Ile Phe Lys Asp
    210                 215                 220
Val Glu Ile Val Thr Leu Ser Asp Gly Lys Asn Ser Ser Lys Arg Gly
225                 230                 235                 240
Lys His Lys Asn Leu His Gly Ser Lys Val Phe Asp Ser Asn Gly Ile
                245                 250                 255
Tyr Asp Ile Asp Pro Lys Asn Trp Lys Ile Glu Asp Asp Lys Asp
                260                 265                 270
Ile Thr Val His Glu Asn Ala Gly Asp Pro Lys Ser Asp Ser Arg Arg
        275                 280                 285
Cys
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
atgaacttgt attttttatt tttt                                              24

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
atcaattaat gaagttttat taaaaga                                           27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
tcttttaata atatttcctt aattgat                                           27

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gggtcgacac agctgcagct c                                                 21

<210> SEQ ID NO 9
<211> LENGTH: 23
<212> TYPE: DNA

```
<213> ORGANISM: Artificial Sequence
<220> FEATURE:
<223> OTHER INFORMATION: Description of Artificial Sequence:
      oligonucleotide

<400> SEQUENCE: 9
gccattatca atcaaggaaa tat                                                23

<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence:coding
      sequence for sarcotoxin IA signal peptide fused to start of
      mite toxin coding sequence

<400> SEQUENCE: 10
atgaacttcc aaaacatatt catattcgtg gcgttaatat tggcggtgtt cgcgggacaa        60
tctcaggcgg gggataatgg c                                                  81

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence:sarcotoxin
      signal peptide sequence fused to the start of the mite toxin
      sequence

<400> SEQUENCE: 11

Met Asn Phe Gln Asn Ile Phe Ile Phe Val Ala Leu Ile Leu Ala Val
 1               5                  10                  15

Phe Ala Gly Gln Ser Gln Ala Gly Asp Asn Gly
             20                  25

<210> SEQ ID NO 12
<211> LENGTH: 57
<212> TYPE: DNA
<213> ORGANISM: Drosophila melanogaster
<220> FEATURE:
<221> NAME/KEY: CDS
<222> LOCATION: (1)..(57)

<400> SEQUENCE: 12 atg ttc aag ttt gtc atg atc tgc gca gtt ttg ggc ctg gcg gtg gcc         48
Met Phe Lys Phe Val Met Ile Cys Ala Val Leu Gly Leu Ala Val Ala
 1               5                  10                  15 gat aat ggc                                                              57
Asp Asn Gly <210> SEQ ID NO 13
<211> LENGTH: 19
<212> TYPE: PRT
<213> ORGANISM: Drosophila melanogaster

<400> SEQUENCE: 13

Met Phe Lys Phe Val Met Ile Cys Ala Val Leu Gly Leu Ala Val Ala
 1               5                  10                  15

Asp Asn Gly

<210> SEQ ID NO 14
<211> LENGTH: 126
<212> TYPE: DNA
<213> ORGANISM: Artificial Sequence
```

```
<220> FEATURE:
<223> OTHER INFORMATION: Description of Artificial Sequence:modified
      signal coding sequence for mite toxin protein

<400> SEQUENCE: 14
atgaaaattt gtacattttt tattctttta ttcaaaatga acttgttttt tttatttatt      60
attccaacaa ttttagcagt taaacctttt aggtctttta ataatatttc cttgattgat     120
aatggc                                                               126

<210> SEQ ID NO 15
<211> LENGTH: 42
<212> TYPE: PRT
<213> ORGANISM: Artificial Sequence
<220> FEATURE:
<223> OTHER INFORMATION: Description of Artificial Sequence:product of
      modified mite toxin signal peptide coding sequence fused to start
      of mite toxin protein

<400> SEQUENCE: 15

Met Lys Ile Cys Thr Phe Phe Ile Leu Leu Phe Lys Met Asn Leu Phe
  1               5                  10                  15

Phe Leu Phe Ile Ile Pro Thr Ile Leu Ala Val Lys Pro Phe Arg Ser
             20                  25                  30

Phe Asn Asn Ile Ser Leu Ile Asp Asn Gly
         35                  40

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: At position 10, n is inosine and at position
      21, n is a, g, c or t.

<400> SEQUENCE: 16
gcggatccan ygtgswgtwy ntkggmgg                                         28

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:peptide from
      AcNPV ecdysteroid UDP-glucosyl transferase protein

<400> SEQUENCE: 17

Ser Val Gln Tyr Leu Gly Gly
  1               5

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: At position 23, n is a or g or c or t.

<400> SEQUENCE: 18
gcgaattcgg mabvmhcacc akngg                                            25
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:peptide
      sequence characteristic of baculovirus ecdysteroid UDP glucosyl
      transferase proteins.

<400> SEQUENCE: 19

Pro Met Val Cys Leu Pro
  1               5

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
tcgacctcag ggcagcttaa ggcctgcagg                                       30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
tcgacctgca ggccttaagc tgccctgagg                                       30

<210> SEQ ID NO 22
<211> LENGTH: 395
<212> TYPE: DNA
<213> ORGANISM: Helicoverpa zea nuclear polyhedrosis virus

<400> SEQUENCE: 22
cgataacaac tttaaagtaa ccatattatg gaacacttga ccgcacaccc aaatagaatg       60
acaaagaatg ttttcatcgt ttcgtcgccc acacaattca aacataacgt tatctttaaa     120
gataacaaat gatgacatat attaaattat ggtgcaatat acatgacaca aacaacttac     180
gtcatcgtaa ccttgaatta aaatgtaaaa acaatttgtg atatcgttaa ttctaggaag     240
ttgggcacaa acaacttacg tcatcgtaac cttaggtcaa atcgttaatt ctaggaagtt     300
gtgcacaaac aacttacgtc atacatgtta ttaatcattt gcggtgcaat cgtcatcgga     360
tcaaacgatt tcggttaaat ttcgacactg gtgtg                                395

<210> SEQ ID NO 23
<211> LENGTH: 2025
<212> TYPE: DNA
<213> ORGANISM: Helicoverpa zea nuclear polyhedrosis virus
<220> FEATURE:
<221> NAME/KEY: CDS
<222> LOCATION: (320)..(1867)

<400> SEQUENCE: 23
tcgacagagt tatattattt attaatgtgt tgctgttgtt gcgtatgaca tcataggtat       60
tagtactgtc attgctaaat atagacatga aataattatc ttcgttgagg ttatcacgaa     120
cactagtagt catcgtgacg atagatatct gtaatacaca catcaaagta aacatgttta     180
```

```
                                                            -continued cttaaacagt aactgaataa taatttcaac atacgcacgc cactataaga tgcagcatcc      240
cgtccgttgg tcatctttcg ataaacgctc tgacccataa acggacgtgc gctaattttt      300
ttttattgct aaattcaaa atg tac aaa caa ata ata act atg tta ttg ttg      352
                      Met Tyr Lys Gln Ile Ile Thr Met Leu Leu Leu
                       1               5                      10 gtg ttg ttt ctg tcg gtt ctg gat gga gcg cgt atc ctg tgc gtt ttt       400
Val Leu Phe Leu Ser Val Leu Asp Gly Ala Arg Ile Leu Cys Val Phe
            15                  20                  25 cct gtt cct tcg tac agt cat cat gca gtg ttc gaa gct tac acc aat       448
Pro Val Pro Ser Tyr Ser His His Ala Val Phe Glu Ala Tyr Thr Asn
        30                  35                  40 gct cta gcg tcg cgt ggc cat aca ata gtc aga att aca ccg ttt ccc       496
Ala Leu Ala Ser Arg Gly His Thr Ile Val Arg Ile Thr Pro Phe Pro
    45                  50                  55 act aag aaa aac gat tca tcc aac gtg aca gat gtc gac gtt agc ttg       544
Thr Lys Lys Asn Asp Ser Ser Asn Val Thr Asp Val Asp Val Ser Leu
 60                 65                  70                  75 tcg aaa gat tat ttt aaa agt ctt gtg gac cga tct aga ctg ttc aag       592
Ser Lys Asp Tyr Phe Lys Ser Leu Val Asp Arg Ser Arg Leu Phe Lys
                80                  85                  90 aaa cga ggc gtt att tcg gaa acg tcc agc gtg acc gct cgc aat tac       640
Lys Arg Gly Val Ile Ser Glu Thr Ser Ser Val Thr Ala Arg Asn Tyr
             95                 100                 105 atc agt cta gta cac atg ttg att gat caa ttc tct gtg gag agt gta       688
Ile Ser Leu Val His Met Leu Ile Asp Gln Phe Ser Val Glu Ser Val
         110                 115                 120 cga caa ttg atc gaa tcc aac aat gtt ttc gat ttg ttg gtg acc gaa       736
Arg Gln Leu Ile Glu Ser Asn Asn Val Phe Asp Leu Leu Val Thr Glu
     125                 130                 135 gcc ttt cta gat tat cct ctg gtg ttt tcg cat ttg ttt ggc gat gtg       784
Ala Phe Leu Asp Tyr Pro Leu Val Phe Ser His Leu Phe Gly Asp Val
 140                 145                 150                 155 cct gtc ata caa att tcg tcg ggt cac gct ttg gcc gaa aat ttt gag       832
Pro Val Ile Gln Ile Ser Ser Gly His Ala Leu Ala Glu Asn Phe Glu
                 160                 165                 170 aca atg gga gcc gtg agc cga cat ccc att tac tat cca aat ttg tgg       880
Thr Met Gly Ala Val Ser Arg His Pro Ile Tyr Tyr Pro Asn Leu Trp
             175                 180                 185 cgc aac aaa ttt caa aat tta aac gtt tgg gag ata ata acg gaa atc       928
Arg Asn Lys Phe Gln Asn Leu Asn Val Trp Glu Ile Ile Thr Glu Ile
         190                 195                 200 tat aca gaa ctg gtg ctg tac ttg gaa ttt gct cgt tta gcc gac gaa       976
Tyr Thr Glu Leu Val Leu Tyr Leu Glu Phe Ala Arg Leu Ala Asp Glu
 205                 210                 215 caa act aaa atg ctt cgc cat caa ttc gga cca aac acg ccc agc gtg      1024
Gln Thr Lys Met Leu Arg His Gln Phe Gly Pro Asn Thr Pro Ser Val
220                 225                 230                 235 gaa gaa ctg cga caa cgc gtt caa tta ttg ttt gtg aat acg cat ccg      1072
Glu Glu Leu Arg Gln Arg Val Gln Leu Leu Phe Val Asn Thr His Pro
                240                 245                 250 ctg ttt gat aat aac aga cca gta ccg ccg agt gta caa tat ttg gga      1120
Leu Phe Asp Asn Asn Arg Pro Val Pro Pro Ser Val Gln Tyr Leu Gly
            255                 260                 265 agt cta cat ctt gat cga aac aat gat gtc gac gaa cag caa acg atg      1168
Ser Leu His Leu Asp Arg Asn Asn Asp Val Asp Glu Gln Gln Thr Met
        270                 275                 280 gac tat aat ttg atg caa ttt tta aat aat tct aca aac ggt gtg gtg      1216
Asp Tyr Asn Leu Met Gln Phe Leu Asn Asn Ser Thr Asn Gly Val Val
    285                 290                 295
```

-continued

```
tac gtg agc ttc ggt acg tct ata cga gtt tca gac atg gac gac gaa      1264
Tyr Val Ser Phe Gly Thr Ser Ile Arg Val Ser Asp Met Asp Asp Glu
300                 305                 310                 315 ttt ctg ttt gaa ttt ata aca gct ttc aag caa tta ccc tat aat ata      1312
Phe Leu Phe Glu Phe Ile Thr Ala Phe Lys Gln Leu Pro Tyr Asn Ile
            320                 325                 330 ttg tgg aag acc gat gga atg ccc atg gaa cac gta ctg cct aaa aat      1360
Leu Trp Lys Thr Asp Gly Met Pro Met Glu His Val Leu Pro Lys Asn
335                 340                 345 gtg ttg aca caa act tgg ctg ccg caa cac cat gta ttg aaa cac agc      1408
Val Leu Thr Gln Thr Trp Leu Pro Gln His His Val Leu Lys His Ser
        350                 355                 360 aat gta gtt gct ttt gtt act caa ggc gga atg cag tca acg gac gaa      1456
Asn Val Val Ala Phe Val Thr Gln Gly Gly Met Gln Ser Thr Asp Glu
365                 370                 375 gcc atc gac gct tgt gta cca cta atc gga atc ccg ttt atg ggc gac      1504
Ala Ile Asp Ala Cys Val Pro Leu Ile Gly Ile Pro Phe Met Gly Asp
380                 385                 390                 395 caa gca tac aat acc aat aaa tac gaa gaa ctc gga atc gga cgc aac      1552
Gln Ala Tyr Asn Thr Asn Lys Tyr Glu Glu Leu Gly Ile Gly Arg Asn
            400                 405                 410 ctc gat ccc gta acg ctc aca agt cat att ttg gtg tct gcc gtt tta      1600
Leu Asp Pro Val Thr Leu Thr Ser His Ile Leu Val Ser Ala Val Leu
        415                 420                 425 gat gtg acc gtc aac aac aag agt cgc tac aca gat aat att aaa gca      1648
Asp Val Thr Val Asn Asn Lys Ser Arg Tyr Thr Asp Asn Ile Lys Ala
430                 435                 440 ttg aat cgt tcc act aat tat cga aca cgg aaa cct atg gaa aag gcc      1696
Leu Asn Arg Ser Thr Asn Tyr Arg Thr Arg Lys Pro Met Glu Lys Ala
445                 450                 455 atc tgg tac aca gaa cat gta att gat aat ggt aaa aat ccc att tta      1744
Ile Trp Tyr Thr Glu His Val Ile Asp Asn Gly Lys Asn Pro Ile Leu
460                 465                 470                 475 aaa acg aag gcc gcc aac gta tcg tat agc aaa tat tat atg agt gat      1792
Lys Thr Lys Ala Ala Asn Val Ser Tyr Ser Lys Tyr Tyr Met Ser Asp
            480                 485                 490 atc atc gtt cct gtt ata acg ttt ttg gta atg act cat ttg ggt cag      1840
Ile Ile Val Pro Val Ile Thr Phe Leu Val Met Thr His Leu Gly Gln
        495                 500                 505 gct att cgg cgg ttg gtt gtt att taa tactgtatga caatgtacac            1887
Ala Ile Arg Arg Leu Val Val Ile
            510                 515 atgtgttaat aaaaaaggca ttactaatat ttagattgtt tcaaattatt tacgcatgac    1947
tacccgtctc ctattgcgca gctacgctag ctttaaatac agccgatggc gtagtaaagt    2007
tcatttaaat atctaaat                                                  2025

<210> SEQ ID NO 24
<211> LENGTH: 515
<212> TYPE: PRT
<213> ORGANISM: Helicoverpa zea nuclear polyhedrosis virus

<400> SEQUENCE: 24

Met Tyr Lys Gln Ile Ile Thr Met Leu Leu Leu Val Leu Phe Leu Ser
1               5                   10                  15

Val Leu Asp Gly Ala Arg Ile Leu Cys Val Phe Pro Val Pro Ser Tyr
            20                  25                  30

Ser His His Ala Val Phe Glu Ala Tyr Thr Asn Ala Leu Ala Ser Arg
        35                  40                  45
```

-continued

```
Gly His Thr Ile Val Arg Ile Thr Pro Phe Pro Thr Lys Lys Asn Asp
 50                  55                  60

Ser Ser Asn Val Thr Asp Val Asp Val Ser Leu Ser Lys Asp Tyr Phe
 65                  70                  75                  80

Lys Ser Leu Val Asp Arg Ser Arg Leu Phe Lys Lys Arg Gly Val Ile
                     85                  90                  95

Ser Glu Thr Ser Ser Val Thr Ala Arg Asn Tyr Ile Ser Leu Val His
                100                 105                 110

Met Leu Ile Asp Gln Phe Ser Val Glu Ser Val Arg Gln Leu Ile Glu
                115                 120                 125

Ser Asn Val Phe Asp Leu Leu Val Thr Glu Ala Phe Leu Asp Tyr
    130                 135                 140

Pro Leu Val Phe Ser His Leu Phe Gly Asp Val Pro Val Ile Gln Ile
145                 150                 155                 160

Ser Ser Gly His Ala Leu Ala Glu Asn Phe Glu Thr Met Gly Ala Val
                165                 170                 175

Ser Arg His Pro Ile Tyr Tyr Pro Asn Leu Trp Arg Asn Lys Phe Gln
                180                 185                 190

Asn Leu Asn Val Trp Glu Ile Ile Thr Glu Ile Tyr Thr Glu Leu Val
                195                 200                 205

Leu Tyr Leu Glu Phe Ala Arg Leu Ala Asp Glu Gln Thr Lys Met Leu
    210                 215                 220

Arg His Gln Phe Gly Pro Asn Thr Pro Ser Val Glu Glu Leu Arg Gln
225                 230                 235                 240

Arg Val Gln Leu Leu Phe Val Asn Thr His Pro Leu Phe Asp Asn Asn
                245                 250                 255

Arg Pro Val Pro Pro Ser Val Gln Tyr Leu Gly Ser Leu His Leu Asp
                260                 265                 270

Arg Asn Asn Asp Val Asp Glu Gln Gln Thr Met Asp Tyr Asn Leu Met
                275                 280                 285

Gln Phe Leu Asn Asn Ser Thr Asn Gly Val Val Tyr Val Ser Phe Gly
    290                 295                 300

Thr Ser Ile Arg Val Ser Asp Met Asp Asp Glu Phe Leu Phe Glu Phe
305                 310                 315                 320

Ile Thr Ala Phe Lys Gln Leu Pro Tyr Asn Ile Leu Trp Lys Thr Asp
                325                 330                 335

Gly Met Pro Met Glu His Val Leu Pro Lys Asn Val Leu Thr Gln Thr
                340                 345                 350

Trp Leu Pro Gln His His Val Leu Lys His Ser Asn Val Val Ala Phe
                355                 360                 365

Val Thr Gln Gly Gly Met Gln Ser Thr Asp Glu Ala Ile Asp Ala Cys
    370                 375                 380

Val Pro Leu Ile Gly Ile Pro Phe Met Gly Asp Gln Ala Tyr Asn Thr
385                 390                 395                 400

Asn Lys Tyr Glu Glu Leu Gly Ile Gly Arg Asn Leu Asp Pro Val Thr
                405                 410                 415

Leu Thr Ser His Ile Leu Val Ser Ala Val Leu Asp Val Thr Val Asn
                420                 425                 430

Asn Lys Ser Arg Tyr Thr Asp Asn Ile Lys Ala Leu Asn Arg Ser Thr
                435                 440                 445

Asn Tyr Arg Thr Arg Lys Pro Met Glu Lys Ala Ile Trp Tyr Thr Glu
    450                 455                 460
```

```
His Val Ile Asp Asn Gly Lys Asn Pro Ile Leu Lys Thr Lys Ala Ala
465                 470                 475                 480

Asn Val Ser Tyr Ser Lys Tyr Tyr Met Ser Asp Ile Ile Val Pro Val
            485                 490                 495

Ile Thr Phe Leu Val Met Thr His Leu Gly Gln Ala Ile Arg Arg Leu
            500                 505                 510

Val Val Ile
        515

<210> SEQ ID NO 25
<211> LENGTH: 506
<212> TYPE: PRT
<213> ORGANISM: Autographa californica nucleopolyhedrovirus

<400> SEQUENCE: 25

Met Thr Ile Leu Cys Trp Leu Ala Leu Leu Ser Thr Leu Thr Ala Val
1               5                   10                  15

Asn Ala Ala Asn Ile Leu Ala Val Phe Pro Thr Pro Ala Tyr Ser His
                20                  25                  30

His Ile Val Tyr Lys Val Tyr Ile Glu Ala Leu Ala Glu Lys Cys His
            35                  40                  45

Asn Val Thr Val Lys Pro Lys Leu Phe Ala Tyr Ser Thr Lys Thr
        50                  55                  60

Tyr Cys Gly Asn Ile Thr Glu Ile Asn Ala Asp Met Ser Val Glu Gln
65                  70                  75                  80

Tyr Lys Lys Leu Val Ala Asn Ser Ala Met Phe Arg Lys Arg Gly Val
                85                  90                  95

Val Ser Asp Thr Asp Thr Val Thr Ala Ala Asn Tyr Leu Gly Leu Ile
            100                 105                 110

Glu Met Phe Lys Asp Gln Phe Asp Asn Ile Asn Val Arg Asn Leu Ile
            115                 120                 125

Ala Asn Asn Gln Thr Phe Asp Leu Val Val Glu Ala Phe Ala Asp
130                 135                 140

Tyr Ala Leu Val Phe Gly His Leu Tyr Asp Pro Ala Pro Val Ile Gln
145                 150                 155                 160

Ile Ala Pro Gly Tyr Gly Leu Ala Glu Asn Phe Asp Thr Val Gly Ala
                165                 170                 175

Val Ala Arg His Pro Val His His Pro Asn Ile Trp Arg Ser Asn Phe
            180                 185                 190

Asp Asp Thr Glu Ala Asn Val Met Thr Glu Met Arg Leu Tyr Lys Glu
            195                 200                 205

Phe Lys Ile Leu Ala Asn Met Ser Asn Ala Leu Leu Lys Gln Gln Phe
210                 215                 220

Gly Pro Asn Thr Pro Thr Ile Glu Lys Leu Arg Asn Lys Val Gln Leu
225                 230                 235                 240

Leu Leu Leu Asn Leu His Pro Ile Phe Asp Asn Asn Arg Pro Val Pro
                245                 250                 255

Pro Ser Val Gln Tyr Leu Gly Gly Ile His Leu Val Lys Ser Ala
            260                 265                 270

Pro Leu Thr Lys Leu Ser Pro Val Ile Asn Ala Gln Met Asn Lys Ser
            275                 280                 285

Lys Ser Gly Thr Ile Tyr Val Ser Phe Gly Ser Ser Ile Asp Thr Lys
            290                 295                 300

Ser Phe Ala Asn Glu Phe Leu Tyr Met Leu Ile Asn Thr Phe Lys Thr
305                 310                 315                 320
```

-continued

```
Leu Asp Asn Tyr Thr Ile Leu Trp Lys Ile Asp Asp Glu Val Val Lys
                325                 330                 335

Asn Ile Thr Leu Pro Ala Asn Val Ile Thr Gln Asn Trp Phe Asn Gln
            340                 345                 350

Arg Ala Val Leu Arg His Lys Lys Met Ala Ala Phe Ile Thr Gln Gly
        355                 360                 365

Gly Leu Gln Ser Ser Asp Glu Ala Leu Glu Ala Gly Ile Pro Met Val
    370                 375                 380

Cys Leu Pro Met Met Gly Asp Gln Phe Tyr His Ala His Lys Leu Gln
385                 390                 395                 400

Gln Leu Gly Val Ala Arg Ala Leu Asp Thr Val Thr Val Ser Ser Asp
                405                 410                 415

Gln Leu Leu Val Ala Ile Asn Asp Val Leu Phe Asn Ala Pro Thr Tyr
            420                 425                 430

Lys Lys His Met Ala Glu Leu Tyr Ala Leu Ile Asn His Asp Lys Ala
        435                 440                 445

Thr Phe Pro Pro Leu Asp Lys Ala Ile Lys Phe Thr Glu Arg Val Ile
    450                 455                 460

Arg Tyr Arg His Asp Ile Ser Arg Gln Leu Tyr Ser Leu Lys Thr Thr
465                 470                 475                 480

Ala Ala Asn Val Pro Tyr Ser Asn Tyr Tyr Met Tyr Lys Ser Val Phe
                485                 490                 495

Ser Ile Val Met Asn His Leu Thr His Phe
            500                 505

<210> SEQ ID NO 26
<211> LENGTH: 506
<212> TYPE: PRT
<213> ORGANISM: Bombyx mori nuclear polyhedrosis virus

<400> SEQUENCE: 26

Met Thr Ile Leu Cys Trp Leu Ala Leu Leu Ser Thr Leu Thr Ala Val
1               5                   10                  15

Asn Ala Val Asn Ile Leu Ala Val Phe Pro Thr Pro Ala Tyr Ser His
            20                  25                  30

His Ile Val Tyr Lys Val Tyr Ile Glu Ala Leu Ala Glu Lys Cys His
        35                  40                  45

Asn Val Thr Val Val Lys Pro Lys Leu Phe Ala Tyr Ser Thr Lys Thr
    50                  55                  60

Tyr Cys Gly Asn Ile Thr Glu Val Asn Ser Asp Met Ser Val Lys Gln
65                  70                  75                  80

Tyr Lys Lys Leu Val Thr Asn Ser Ala Met Phe Arg Lys Arg Gly Val
                85                  90                  95

Val Ser Asp Thr Asp Thr Val Thr Ala Ala Asn Tyr Leu Gly Leu Ile
            100                 105                 110

Glu Met Phe Lys Asp Gln Phe Asp Asn Ile Asn Val Arg Asn Leu Ile
        115                 120                 125

Ala Asn Asn Gln Thr Phe Asp Leu Val Val Glu Ala Phe Ala Asp
    130                 135                 140

Tyr Ala Leu Val Phe Gly His Leu Tyr Asp Pro Ala Pro Val Ile Gln
145                 150                 155                 160

Ile Ala Pro Gly Tyr Gly Leu Ala Glu Asn Phe Asp Thr Val Gly Ala
                165                 170                 175

Val Ala Arg His Pro Val His His Pro Asn Ile Trp Arg Asn Asn Phe
            180                 185                 190
```

-continued

Asp Asp Thr Lys Ala Asn Leu Met Thr Glu Met Arg Leu Tyr Lys Glu
        195                 200                 205

Phe Lys Ile Leu Ala Asn Met Ser Asn Ala Leu Leu Lys Gln Gln Phe
        210                 215                 220

Gly Pro Asp Thr Pro Thr Ile Glu Glu Leu Arg Asn Lys Val Gln Leu
225                 230                 235                 240

Leu Leu Leu Asn Leu His Pro Ile Phe Asp Asn Asn Arg Pro Val Ser
        245                 250                 255

Pro Ser Val Gln Tyr Leu Gly Gly Ile His Leu Val Lys Ser Ala
        260                 265                 270

Pro Leu Thr Lys Leu Ser Pro Val Ile Asp Ala Lys Met Asn Lys Ser
        275                 280                 285

Lys Ser Gly Ala Ile Tyr Val Ser Phe Gly Ser Ser Ile Asp Thr Lys
        290                 295                 300

Ser Phe Ala Asn Glu Phe Phe Tyr Met Leu Ile Asn Thr Phe Lys Ala
305                 310                 315                 320

Leu Asp Asn Tyr Thr Ile Leu Trp Lys Ile Asp Asp Glu Val Val Lys
        325                 330                 335

Asn Ile Thr Leu Pro Ala Asn Val Ile Thr Gln Asn Trp Phe Asn Gln
        340                 345                 350

Arg Ala Val Leu Arg His Lys Lys Met Ala Ala Phe Ile Thr Gln Gly
        355                 360                 365

Gly Leu Gln Ser Ser Asp Glu Ala Leu Glu Ala Gly Ile Pro Met Val
        370                 375                 380

Cys Leu Pro Met Met Gly Asp Gln Phe Tyr His Ala His Lys Leu Gln
385                 390                 395                 400

Gln Leu Gly Val Ala Arg Ala Leu Asp Thr Val Thr Val Ser Ser Asp
        405                 410                 415

Gln Leu Leu Leu Ala Ile Asn Asp Val Leu Phe Asn Ala Ser Thr Tyr
        420                 425                 430

Lys Lys His Met Ala Glu Leu Tyr Ala Leu Ile Asn Asn Asp Lys Ala
        435                 440                 445

Thr Phe Pro Pro Leu Asp Lys Ala Ile Lys Phe Thr Glu Arg Val Ile
        450                 455                 460

Arg Tyr Arg His Asp Ile Ser Arg Arg Leu Tyr Ser Leu Lys Thr Thr
465                 470                 475                 480

Ala Ala Asn Val Pro Tyr Ser Asn Tyr Tyr Met Tyr Lys Ser Val Leu
        485                 490                 495

Ser Ile Val Met Asn His Ile Ala His Phe
            500                 505

<210> SEQ ID NO 27
<211> LENGTH: 491
<212> TYPE: PRT
<213> ORGANISM: Choristoneura fumiferana nucleopolyhedrovirus

<400> SEQUENCE: 27

Met Ala Ser Leu Leu Ile Ala Leu Thr Leu Leu Ala Ala Asp Ala Gln
1                 5                   10                  15

Thr Ala Asn Ile Leu Ala Val Leu Pro Thr Pro Ala Tyr Ser His His
            20                  25                  30

Ala Val Tyr Lys Ala Tyr Val His Ala Leu Ala Lys Asn Cys His Asn
            35                  40                  45

Val Thr Ala Val Lys Pro Arg Leu Leu Asp Tyr Ala Leu Leu Asn Glu
        50                  55                  60

-continued

```
Cys Gly Arg Ile Glu Gln Ile Asp Ala Asp Met Ser Leu Glu Gln Tyr
 65                  70                  75                  80

Gln Lys Leu Met Ala Gly Ser Gly Ala Phe Arg Lys Arg Gly Val Val
                 85                  90                  95

Ala Asp Glu Thr Thr Val Thr Ala Asp Asn Tyr Met Ser Leu Ile Glu
                100                 105                 110

Met Phe Lys Asp Gln Phe Asp Asn Ala Asn Val Arg His Phe Leu Ala
            115                 120                 125

Ser Asn Arg Thr Phe Asp Ala Val Val Glu Ala Ser Ala Asp Tyr
        130                 135                 140

Glu Leu Val Phe Gly His Leu Phe Arg Pro Ala Thr Val Ile Gln Ile
145                 150                 155                 160

Ala Pro Gly Tyr Gly Leu Ala Glu Asn Phe Asp Ala Ala Gly Ala Val
                165                 170                 175

Ala Arg His Pro Val His Tyr Pro Asn Ile Trp Arg Ser Ser Phe Ser
            180                 185                 190

Gly Glu Ala Ala Gly Ala Leu Ser Glu Trp Arg Leu Leu Asn Glu Phe
        195                 200                 205

Glu Leu Leu Ala Ser Gln Arg Ser Asn Glu Leu Leu Lys Gln Gln Phe
210                 215                 220

Gly Leu Asp Thr Pro Thr Ile Arg Gln Leu Arg Asp Asn Val Gln Leu
225                 230                 235                 240

Leu Leu Leu Asn Leu His Pro Val Tyr Asp Asn Asn Arg Pro Val Pro
                245                 250                 255

Pro Ser Val Gln Tyr Leu Gly Gly Leu His Leu Ser Gln Ala Pro
            260                 265                 270

Ser His Lys Leu Thr Ala Ala Leu Glu Arg Arg Leu Asn Glu Ser Val
        275                 280                 285

Asp Gly Ala Ile Tyr Val Ser Phe Gly Ser Ser Ile Asp Thr Asn Ser
290                 295                 300

Ile His Ala Glu Phe Ile Gln Met Leu Leu Glu Ser Phe Val Gln Leu
305                 310                 315                 320

Asn Asn Tyr Thr Val Leu Trp Lys Val Asp Asp Thr Val Pro Ala Ser
                325                 330                 335

Val Lys Leu Pro Ser Asn Val Val Thr Gln Lys Trp Phe Asp Gln Arg
            340                 345                 350

Ala Val Leu His His Lys Lys Val Ala Phe Val Met Gln Ala Gly
        355                 360                 365

Leu Gln Ser Ser Asp Glu Ala Leu Glu Ser Arg Val Pro Met Val Cys
370                 375                 380

Leu Pro Met Met Gly Asp Gln Phe His His Ala Arg Lys Leu Gln Gln
385                 390                 395                 400

Phe Gly Val Ala Arg Thr Leu Asp Thr Ala Val Val Ser Ala Ala Gln
                405                 410                 415

Leu Thr Leu Ala Ile Gly Glu Val Ile Ala Asp Ala Glu Ala Tyr Arg
            420                 425                 430

Ala Arg Ile Asp Asp Leu Arg Ala Val Leu Glu His Asp Ala Ala Pro
        435                 440                 445

Ala Glu Lys Ala Val Lys Phe Thr Glu Arg Val Ile Ile Phe Lys His
450                 455                 460
```

```
Asp Met Thr Arg Pro Ala Arg Thr Leu Lys Thr Thr Ser Ala Asn Ile
465                 470                 475                 480

Ala Tyr Ser Asp Tyr Phe Leu Arg Phe Pro Leu
                485                 490

<210> SEQ ID NO 28
<211> LENGTH: 493
<212> TYPE: PRT
<213> ORGANISM: Cf defective nucleopolyhedrosis virus

<400> SEQUENCE: 28

Met Ile Phe Ile Leu Leu Thr Thr Leu Leu Ala Val Gly Gly Ala Gln
  1               5                  10                  15

Thr Ala Asn Ile Leu Ala Val Leu Pro Thr Pro Ala Tyr Ser His His
                 20                  25                  30

Leu Val Tyr Gln Ala Tyr Val Gln Ala Leu Ala Asp Lys Cys His Asn
             35                  40                  45

Val Thr Val Val Lys Pro Gln Leu Leu Asp Tyr Ala Ala Ala Asn Lys
 50                  55                  60

Gln Arg Cys Gly Arg Ile Glu Gln Ile Asp Ala Asp Met Ser Ser Gln
 65                  70                  75                  80

Gln Tyr Lys Lys Leu Val Ala Ser Ser Gly Ala Phe Arg Lys Arg Gly
                 85                  90                  95

Val Val Ser Asp Glu Thr Thr Val Thr Ala Glu Asn Tyr Met Gly Leu
            100                 105                 110

Val Glu Met Phe Arg Asp Gln Phe Asp Asn Ala His Val Arg Ser Phe
        115                 120                 125

Leu Ala Thr Asn Arg Thr Phe Asp Val Val Val Glu Ala Phe Ala
130                 135                 140

Asp Tyr Ala Leu Val Phe Gly His Leu Phe Arg Pro Ala Pro Val Ile
145                 150                 155                 160

Gln Ile Ala Pro Gly Tyr Gly Leu Ala Glu Asn Phe Asp Ala Val Gly
                165                 170                 175

Ala Val Gly Arg His Pro Val His Tyr Pro Asn Ile Trp Arg Ser Ser
            180                 185                 190

Ser Ile Gly Asn Ala Asp Gly Ala Leu Ile Glu Trp Arg Leu Tyr Asn
        195                 200                 205

Glu Phe Glu Leu Leu Ala Arg Arg Ser Asp Ala Leu Leu Lys Leu Gln
210                 215                 220

Phe Gly Pro Asn Thr Pro Thr Ile Arg Gln Leu Arg Asn Asn Val Gln
225                 230                 235                 240

Leu Leu Leu Leu Asn Leu His Pro Val Tyr Asp Asn Asn Arg Pro Val
                245                 250                 255

Pro Pro Ser Val Gln Tyr Leu Gly Gly Gly Leu His Leu Thr Leu Glu
            260                 265                 270

Pro Pro Gln Arg Leu Asp Ile Glu Leu Glu Lys Arg Leu Asn Ala Ser
        275                 280                 285

Val Asn Gly Thr Val Tyr Val Ser Phe Gly Ser Ser Ile Asp Thr Asn
290                 295                 300

Ser Ile His Ala Glu Phe Leu Glu Met Leu Leu Asp Thr Phe Ala Lys
305                 310                 315                 320

Leu Asp Asn Arg Thr Val Leu Trp Lys Val Asp Asp Ala Val Ala Lys
                325                 330                 335

Ser Val Val Leu Pro Arg Asn Val Ile Ala Gln Lys Trp Phe Asn Gln
            340                 345                 350
```

```
Arg Ala Val Leu Asn His Arg Asn Val Ala Phe Val Thr Gln Gly
            355                 360                 365

Gly Leu Gln Ser Ser Asp Glu Ala Leu His Ala Arg Val Pro Met Val
        370                 375                 380

Cys Leu Pro Met Met Gly Asp Gln Phe His His Ser Ala Lys Leu Glu
385                 390                 395                 400

Gln Phe Gly Val Ala Arg Ala Leu Asn Thr Val Thr Val Ser Ala Ala
            405                 410                 415

Gln Leu Ala Leu Ala Val Gly Asp Val Ile Ala Ile Arg Leu Ala Tyr
            420                 425                 430

Gln Leu Arg Met Thr Asn Leu Leu Asn Val Val Ala Phe Asp Glu Ala
            435                 440                 445

Thr Pro Ala Asp Lys Ala Ile Lys Phe Thr Glu Arg Val Ile Arg Glu
        450                 455                 460

Gly His Asp Ile Thr Arg Ser Glu Cys Ser Leu Lys Ser Pro Ser Ala
465                 470                 475                 480

Asn Thr Asp Tyr Ser Asp Tyr Phe Val Arg Phe Pro Leu
            485                 490

<210> SEQ ID NO 29
<211> LENGTH: 488
<212> TYPE: PRT
<213> ORGANISM: Lymantria dispar nucleopolyhedrovirus

<400> SEQUENCE: 29

Met Thr Ala Tyr Leu Ile Val Phe Cys Leu Cys Cys Trp Ser Ala Ala
 1               5                  10                  15

Arg Ser Ala Asn Ile Leu Ala Tyr Phe Pro Thr Pro Ser Tyr Ser His
            20                  25                  30

Gln Leu Val Phe Arg Ala Tyr Val Glu Leu Leu Ala Glu Arg Gly His
        35                  40                  45

Ala Val Thr Val Ile Arg Pro Leu Thr Arg Val Asp Phe Asn Arg Asn
 50                  55                  60

Ala Gly Asn Leu Thr Thr Ile Asp Leu Asp Gly Asp Gly Leu Leu Leu
 65                  70                  75                  80

Leu Met Lys Ala Ser Thr Thr His Arg Lys Arg Gly Ile Val Ala Asp
                85                  90                  95

Thr Asp Thr Val Thr Ala Asp Asn Tyr Glu Ala Leu Val Arg Met Val
            100                 105                 110

Asp Arg Gln Ile His Ser Glu Pro Phe Gln Arg His Leu Lys Ser Ala
        115                 120                 125

Arg Arg Gly Tyr Asp Leu Leu Val Val Glu Ala Phe Val Asp Tyr Ala
130                 135                 140

Leu Ile Ala Ser His Leu Phe Gly Asp Val Pro Val Val Gln Ile Ser
145                 150                 155                 160

Ser Gly His Ala Thr Ala Glu Asn Phe Glu Thr Met Gly Ala Thr Ser
                165                 170                 175

Arg His Pro Arg Tyr Tyr Pro Asn Leu Trp Arg Phe Asn Phe Gly Pro
            180                 185                 190

Leu Ser Val Trp Asp Gly Val Arg Glu Leu Tyr Thr Glu Leu Arg Leu
        195                 200                 205

Gln Arg Glu Phe Gly Leu Leu Ala Asp Arg Gln Asp Ala Leu Leu Lys
    210                 215                 220

Arg Arg Phe Gly Pro Glu Ala Pro Gly Leu Arg Glu Leu Arg Ser Arg
225                 230                 235                 240
```

-continued

```
Val Arg Leu Leu Phe Val Asn Val His Ser Val Phe Asp Asn Asn Arg
                245                 250                 255

Pro Val Pro Pro Ser Val Gln Tyr Leu Gly Gly Leu His Leu His Asp
            260                 265                 270

Arg Arg Ala Glu Pro Leu Ser Glu Ala Val Ala Arg Phe Leu Asp Glu
        275                 280                 285

Ser Arg Arg Gly Val Val Tyr Val Ser Phe Gly Ser Gly Leu Ala Thr
    290                 295                 300

Glu Asp Met Asp Ala Asp Met Ala Ala Leu Leu Asp Ala Phe Lys
305                 310                 315                 320

Met Met Pro Tyr Asp Val Leu Trp Lys His Asp Gly Arg Val Asp Gly
                325                 330                 335

Leu Thr Ile Pro Ala Asn Val Phe Val Gln Lys Trp Phe Ala Gln Phe
            340                 345                 350

Glu Val Leu Gln His Lys Asn Val Lys Ala Phe Val Thr Gln Ala Gly
        355                 360                 365

Val Gln Ser Thr Asp Glu Ala Val Glu Asn Leu Val Pro Leu Val Gly
    370                 375                 380

Val Pro Leu Met Gly Asp Gln Ala Phe Asn Ala His Arg Tyr Val Glu
385                 390                 395                 400

Leu Gly Ile Gly Val Ala Leu Asp Ala Thr Arg Leu Thr Ala Ala Asp
                405                 410                 415

Leu Ala Arg Ala Val Glu Gln Val Thr Ser Asp Arg Ala Tyr Arg Glu
            420                 425                 430

Asn Leu Glu Arg Leu Arg Arg Leu Leu Arg His Gln Cys Ala Ser Pro
        435                 440                 445

Thr His Lys Ala Val Trp Tyr Thr Glu His Ala Leu Arg Arg Asp Gly
    450                 455                 460

Asp Ala Leu Lys Thr Lys Ala Ala Asn Val Asp Tyr Ala Glu Tyr Cys
465                 470                 475                 480

Met Ser Thr Cys Trp Arg Pro Cys
                485
```

<210> SEQ ID NO 30
<211> LENGTH: 488
<212> TYPE: PRT
<213> ORGANISM: Mamestra brassicae nuclear polyhedrosis virus

<400> SEQUENCE: 30

```
Met Thr Ala Tyr Leu

```
Arg Arg Gly Tyr Asp Leu Leu Val Val Glu Ala Phe Val Asp Tyr Ala
        130                 135                 140

Leu Ile Ala Ser His Leu Phe Gly Asp Val Pro Val Val Gln Ile Ser
145                 150                 155                 160

Ser Gly His Ala Thr Ala Glu Asn Phe Glu Thr Met Gly Ala Thr Ser
                165                 170                 175

Arg His Pro Arg Tyr Tyr Pro Asn Leu Trp Arg Phe Asn Phe Gly Pro
            180                 185                 190

Leu Ser Val Trp Asp Gly Val Arg Glu Leu Tyr Thr Glu Leu Arg Leu
                195                 200                 205

Gln Arg Glu Phe Gly Leu Leu Ala Asp Arg Gln Asp Ala Leu Leu Lys
        210                 215                 220

Arg Arg Phe Gly Pro Glu Ala Pro Gly Leu Arg Glu Leu Arg Ser Arg
225                 230                 235                 240

Val Arg Leu Leu Phe Val Asn Val His Ser Val Phe Asp Asn Asn Arg
                245                 250                 255

Pro Val Pro Pro Ser Val Gln Tyr Leu Gly Gly Leu His Leu His Asp
            260                 265                 270

Arg Arg Ala Glu Pro Leu Ser Glu Ala Val Ala Arg Phe Leu Asp Glu
        275                 280                 285

Ser Arg Arg Gly Val Val Tyr Val Ser Phe Gly Ser Gly Leu Ala Thr
    290                 295                 300

Glu Asp Met Asp Ala Asp Met Ala Ala Leu Leu Asp Ala Phe Lys
305                 310                 315                 320

Met Met Pro Tyr Asp Val Leu Trp Lys His Asp Gly Arg Val Asp Gly
                325                 330                 335

Leu Thr Ile Pro Ala Asn Val Phe Gln Lys Trp Phe Ala Gln Phe
            340                 345                 350

Glu Val Leu Gln His Lys Asn Val Lys Ala Phe Val Thr Gln Ala Gly
        355                 360                 365

Val Gln Ser Thr Asp Glu Ala Val Glu Asn Leu Val Pro Leu Val Gly
    370                 375                 380

Val Pro Leu Met Gly Asp Gln Ala Phe Asn Ala His Arg Tyr Val Glu
385                 390                 395                 400

Leu Gly Ile Gly Val Ala Leu Asp Ala Thr Arg Leu Thr Ala Ala Asp
                405                 410                 415

Leu Ala Arg Ala Val Glu Gln Val Thr Ser Asp Arg Ala Tyr Arg Glu
            420                 425                 430

Asn Leu Glu Arg Leu Arg Arg Leu Leu Arg His Gln Cys Ala Ser Pro
        435                 440                 445

Thr His Lys Ala Val Trp Tyr Thr Glu His Ala Leu Arg Arg Asp Gly
    450                 455                 460

Asp Ala Leu Lys Thr Lys Ala Ala Asn Val Asp Tyr Ala Glu Tyr Cys
465                 470                 475                 480

Met Ser Thr Cys Trp Arg Pro Cys
                485
```

<210> SEQ ID NO 31
<211> LENGTH: 489
<212> TYPE: PRT
<213> ORGANISM: Orgyia pseudotsugata nuclear polyhedrosis virus

<400> SEQUENCE: 31

```
Met Val Phe Leu Ile Ile Ala Leu Thr Leu Leu Ala Thr Gly Ala Arg
 1               5                  10                  15
```

-continued

```
Ala Ala Ser Ile Leu Ala Val Leu Pro Thr Pro Ala Tyr Ser His His
         20                  25                  30
Val Val Tyr Arg Ala Tyr Val His Ala Leu Val Lys Asn Cys His Asn
         35                  40                  45
Val Thr Val Ile Lys Pro Gln Leu Leu Asp Tyr Ala Val Gln Asp Glu
         50                  55                  60
Cys Gly Arg Val Glu Gln Ile Asp Ala Asp Met Ser Ala Gln Gln Tyr
 65                  70                  75                  80
Lys Lys Leu Val Ala Ser Ser Gly Val Phe Arg Lys Arg Gly Val Val
             85                   90                  95
Ala Asp Glu Thr Thr Val Thr Ala Asp Asn Tyr Met Gly Leu Ile Glu
             100                 105                 110
Met Phe Lys Asp Gln Phe Asp Asn Ala Asn Val Arg Arg Phe Leu Ser
         115                 120                 125
Thr Asn Arg Thr Phe Asp Ala Val Val Glu Ala Phe Ala Asp Tyr
         130                 135                 140
Ala Leu Val Phe Gly His Leu Phe Arg Pro Ala Pro Val Ile Gln Ile
145                 150                 155                 160
Ala Pro Gly Tyr Gly Leu Ala Glu Asn Phe Glu Arg Arg Arg Ala Val
             165                 170                 175
Ala Arg His Pro Leu His Tyr Pro Thr Phe Gly Ala Ala Ala Leu Thr
             180                 185                 190
Arg Arg Gly Gly Ala Leu Ser Glu Trp Arg Leu Leu Asn Glu Phe Glu
         195                 200                 205
Leu Leu Ala Arg Arg Ser Asp Glu Leu Leu Lys Gln Gln Phe Gly Lys
         210                 215                 220
Ser Thr Pro Thr Ile Arg Gln Leu Arg Asp Asn Val Gln Leu Leu Leu
225                 230                 235                 240
Leu Asn Leu His Pro Val Tyr Asp Asn Asn Arg Pro Val Pro Pro Ser
             245                 250                 255
Val Gln Tyr Leu Gly Gly Gly Leu His Leu Ala Gln Ala Leu Pro Gln
             260                 265                 270
Arg Leu Asp Ala Pro Leu Glu Arg Arg Leu Asn Glu Ser Val Asp Gly
         275                 280                 285
Ala Val Tyr Val Ser Phe Gly Ser Gly Ile Asp Thr Asn Ser Ile His
         290                 295                 300
Ala Glu Phe Leu Gln Met Leu Leu Asp Thr Phe Ala Asn Leu Asn Asn
305                 310                 315                 320
Tyr Thr Val Leu Trp Lys Val Asp Asp Ala Val Ala Ala Ser Val Ala
             325                 330                 335
Leu Pro Arg Asn Val Leu Ala Gln Lys Trp Phe Ser Gln Thr Ala Val
             340                 345                 350
Leu Arg His Lys Asn Val Val Ala Phe Val Thr Gln Ala Gly Leu Gln
         355                 360                 365
Ser Ser Asp Glu Ala Leu Gln Ala Arg Val Pro Met Val Cys Leu Pro
         370                 375                 380
Met Met Gly Asp Gln Phe His His Ala Arg Lys Leu Gln Gln Phe Gly
385                 390                 395                 400
Val Ala Arg Ala Leu Asp Thr Ala Ala Val Ser Ala Pro Gln Leu Gln
             405                 410                 415
Leu Ala Ile Arg Glu Val Ile Ala Asp Gly Glu Ala Tyr Arg Ala Arg
             420                 425                 430
```

```
Ile Asp Lys Leu Arg Ala Val Val Glu His Asp Ala Ala Pro Asp Glu
        435                 440                 445

Lys Ala Val Lys Phe Thr Glu Arg Val Ile Lys Phe Asn Asn Asp Val
        450                 455                 460

Asn Trp Pro Ala Arg Ser Leu Lys Thr Thr Ala Ala Asn Met Ala Tyr
465                 470                 475                 480

Ser Asp Tyr Phe Val Arg Phe Pro Leu
                485

<210> SEQ ID NO 32
<211> LENGTH: 515
<212> TYPE: PRT
<213> ORGANISM: Spodoptera littoralis nuclear polyhedrosis virus

<400> SEQUENCE: 32

Met Lys Met Ile Ile Leu Val Val Ser Leu His Val Leu Arg Asn Ser
 1               5                  10                  15

Ala Ala Val Arg Val Leu Cys Met Phe Pro Thr Pro Ser Tyr Ser His
                20                  25                  30

Gln Thr Val Phe Asp Val Tyr Val Asn Ala Leu Leu Arg Arg Gly His
            35                  40                  45

Ser Leu Val Val Ile Ser Pro Lys Ile His Asn His Asn His Gly His
        50                  55                  60

Arg His His Arg His Glu Asn Leu Thr Glu Ile Asp Val Gly Ser Val
65                  70                  75                  80

Thr Asn Asn Phe Phe Lys Arg Leu Leu Gln Asp Ser Lys Val Ser Arg
                85                  90                  95

Lys Arg Gly Ile Val Ser Asp Ser Ser Thr Val Thr Arg Val Asn Tyr
            100                 105                 110

Leu Gly Leu Ala Arg Met Ile Ser Ala Gln Phe Glu His Glu Gln Val
        115                 120                 125

Lys Arg Leu Leu Arg Ser Asn Gln Thr Phe Asp Val Ile Val Ile Glu
    130                 135                 140

Ala Phe Val Ser Tyr Pro Leu Ile Leu Ser Tyr Phe Phe Lys Asp Thr
145                 150                 155                 160

Pro Val Ile Gln Ile Ser Ser Gly His Gly Thr Ala Glu Asn Phe Glu
                165                 170                 175

Thr Met Gly Ala Val Ala Arg His Pro Val Tyr Tyr Pro Asn Met Trp
            180                 185                 190

Arg Asp Arg Phe Lys Gly Leu Ser Val Trp Gln Thr Val Arg Gln Val
        195                 200                 205

Phe Thr Glu Ile Arg Leu Tyr Met Glu Phe Ser Gln Leu Asp Ala Asp
    210                 215                 220

Gln Ser Ala Met Met Lys Arg Gln Phe Gly Ser Lys Val Pro Asp Val
225                 230                 235                 240

Asp Ala Leu Arg Lys Asn Val His Met Met Phe Val Asn Thr His Pro
                245                 250                 255

Val Phe Asp Thr Asn Arg Pro Val Pro Ser Asn Val Gln Tyr Leu Gly
            260                 265                 270

Gly Ile His Ile Asp Pro Ala Val Thr Ser Val Ala Asp Glu Ile Asp
        275                 280                 285

Asn Asp Leu Ala Glu Phe Leu Glu Asn Ser Thr Met Gly Val Val Tyr
    290                 295                 300

Val Ser Leu Gly Ser Ser Val Arg Ala Ser Asp Met Asp Ser Asn Met
305                 310                 315                 320
```

```
Leu Asn Val Phe Val Glu Thr Phe Arg Ser Ile Pro Tyr Arg Val Leu
                325                 330                 335

Trp Lys Val Asp Lys Ser Asp Lys Ile Phe Asp Asn Ile Pro Ser Asn
                340                 345                 350

Val Leu Ile Gln Arg Trp Phe Pro Gln Arg Arg Val Leu Lys His Arg
                355                 360                 365

Asn Val Lys Val Phe Ile Thr Gln Gly Gly Val Gln Ser Thr Asp Glu
                370                 375                 380

Ala Ile Asp Ala Gly Val Pro Met Phe Gly Val Pro Ile Met Gly Asp
385                 390                 395                 400

Gln Phe Tyr Asn Val Tyr Met Tyr Glu Thr Tyr Gly Ile Gly Arg Gly
                405                 410                 415

Val Asp Thr Leu Thr Val Asp Ala Arg Gln Leu Thr Glu Ile Val Met
                420                 425                 430

Asp Val Ala Asp Asn Glu Lys Tyr Lys Asn Gly Thr Leu Trp Leu Arg
                435                 440                 445

Asp Ala Ile Met Asp Gln Pro Met Arg Pro Leu Glu Lys Ala Val Trp
                450                 455                 460

Tyr Thr Glu His Val Ala Arg Arg Lys Gly Ala Lys Lys His Leu Gly
465                 470                 475                 480

Thr Arg Ala Ala Asn Val Thr Tyr Ser Lys Tyr Ala Met Phe Asp Leu
                485                 490                 495

Ile Leu Pro Met Leu Ile Thr Ile Phe Ser Thr Tyr Leu Gln Lys Ile
                500                 505                 510

Leu Ser Ile
        515

<210> SEQ ID NO 33
<211> LENGTH: 460
<212> TYPE: PRT
<213> ORGANISM: Lacanobia oleracea granulovirus

<400> SEQUENCE: 33

Met Phe Ile Ser Ile Leu Leu Ala Leu Ala Val Glu Arg Ile Leu
  1               5                  10                 15

Cys Ala Asn Ile Leu Cys Val Phe Pro Thr Pro Ala Tyr Ser His Gln
                 20                  25                 30

Ser Val Phe Ser Ala Tyr Ile Asp Lys Leu Ser Trp Ala Gly His Asn
                35                  40                  45

Val Thr Val Ile Thr Pro Met Pro Arg Ala Val Asp His Val His Gln
     50                  55                  60

Val Val Ser Ser Leu Ser Val His Tyr Phe Asn Asn Leu Ile Lys Asn
65                  70                  75                  80

Ser Thr Met Ile Lys Lys Arg Gly Val Val Ala Asp Glu Thr Thr Val
                85                  90                  95

Thr Lys Glu Asn Tyr Met Gly Leu Ile Asn Leu Val Ala His Glu Ile
                100                 105                 110

Lys Ser Pro Asn Val Thr Arg Leu Leu Arg Asn Lys Gly Asn Lys Phe
                115                 120                 125

Asp Leu Ile Val Cys Glu Ala Tyr Val Ser Tyr Ile Leu Val Phe Gly
                130                 135                 140

Ala Ile Tyr Asp Ala Pro Val Ile Gln Phe Ser Ser Gly Tyr Ala Ile
145                 150                 155                 160

Pro Glu Asn Phe Glu Thr Val Gly Gly Glu Val Ala Arg Asn His Ile
                165                 170                 175
```

-continued

```
Lys His Pro Asn Ile Trp Arg Ser Asp Phe Ser Lys Ser Asn Phe Glu
            180                 185                 190

Gln Leu Met Thr Glu Asn Tyr Leu Lys Asn Glu Trp Ala Leu Leu Glu
        195                 200                 205

Lys Glu Gln Glu Asn Met Leu Lys Arg Asp Phe Gly Tyr His His Asp
    210                 215                 220

Met Cys Gln Leu Lys Ser Arg Val Leu Met Leu Phe Ile Asn Val Pro
225                 230                 235                 240

Ala Val Phe Asp Asn Asn Arg Asp Val Ser Asn Asn Ile Gln Tyr Leu
            245                 250                 255

Gly Gly Ile His Leu Lys Lys Pro Arg Thr Val Arg Asp Ser Arg Leu
            260                 265                 270

Leu Ser Phe Met Glu Lys His His Ile Ile Val Tyr Ala Ser Phe Gly
        275                 280                 285

Ser Gly Ile Asp Val Leu Asn Met Asp Ala Asn Leu Ile Ala Glu Phe
    290                 295                 300

Val Arg Val Phe Asn Ser Ile Pro Tyr Ala Val Leu Trp Lys Val Asp
305                 310                 315                 320

Ser Ser Ile His Leu Lys His Asn Ile Ser Ser Asn Val His Thr Gln
            325                 330                 335

Ser Trp Phe Pro Gln Arg Asp Val Leu Asn His Pro His Ile Lys Val
            340                 345                 350

Phe Ile Thr Gln Gly Gly Val Gln Ser Thr Asp Glu Ala Val Asn Ser
        355                 360                 365

Gly Val Pro Met Ile Gly Ile Pro Ile Met Gly Asp Gln Phe Tyr Asn
        370                 375                 380

Val Arg Arg Tyr Thr Glu Leu Gly Ile Gly Glu Lys Val Asn Ile Leu
385                 390                 395                 400

Arg Leu Glu Glu Glu Gly Leu Asp Arg Lys Ile Lys Asn Leu Val His
            405                 410                 415

Asn Lys Ser Tyr Glu Leu Asn Ile Lys Arg Leu Asn Leu Phe Ile Ser
            420                 425                 430

Asp Thr Pro Val Lys Pro Leu Arg Lys Ala Leu Trp Phe Thr Asn Tyr
        435                 440                 445

Val Leu Arg Asn Lys Asp Ala Ile Asp Lys Phe Lys
    450                 455                 460
```

BIOLOGICAL INSECT CONTROL AGENTS EXPRESSING INSECT-SPECIFIC TOXIN GENES, METHODS AND COMPOSITIONS

CROSS-REFERENCE TO RELATED APPLICATIONS

This application is a Continuation-in-Part of U.S. patent application Ser. No. 08/720,606, filed Oct. 1, 1996, now abandoned.

ACKNOWLEDGEMENT OF GOVERNMENT FUNDING not applicable

TECHNICAL FIELD OF THE INVENTION

The present invention relates to methods and compositions for improved biological control of insect pests. More particularly, the present invention relates to the efficient expression of insect-specific toxins coding sequences in baculoviruses for use as biological insect control agents.

BACKGROUND OF THE INVENTION

Interest in the biological control of insect pests has arisen as a result of disadvantages of conventional chemical pesticides. Chemical pesticides generally affect beneficial as well as nonbeneficial species, and insect pests tend to acquire resistance to such chemicals. Furthermore, chemical residues pose environmental hazards and possible health concerns. Biological control presents an alternative means of pest control which can reduce dependence on chemical pesticides.

Baculoviruses are a large group of evolutionarily related viruses which infect only arthropods [Miller, L. K. (1981) in *Genetic Engineering in the Plant Sciences*, N. Panopoulous, (ed.), Praeger Publ., New York, pp. 203–224; Carstens, (1980) *Trends in Biochemical Science* 52:107–110; Harrap and Payne (1979) in *Advances in Virus Research*, Vol. 25, Lawfer et al. (eds.), Academic Press, New York, pp. 273–355, Granados, R. R. and Federici, B. A. eds. (1986) *The Biology of Baculoviruses*, Vol. 1, *Biological Properties and Molecular Biology*, CRC Press Inc., Boca Raton, Fla.). Some baculoviruses only infect insects which are pests of commercially important agricultural and forestry crops. Other baculoviruses are known which specifically infect other insect pests, e.g., mosquitoes and fleas. Such baculoviruses are potentially valuable as biological control agents. A potential advantage of baculoviruses as biological pesticides is their host specificity. Because individual baculovirus strains usually only infect one or a few species of insects, they pose little or no risk to man or the environment, and can be used without adversely affecting beneficial insect species.

Baculovirus subgroups include nuclear polyhedrosis viruses, now called nucleopolyhedroviruses (NPVs) and granulosis viruses, now called granuloviruses (GV). In the occluded forms of baculoviruses, the virions (enveloped nucleocapsids) are embedded in a crystalline protein matrix. This structure, referred to as an occlusion body, is the form found extraorganismally in nature, and it is generally responsible for spreading the infection between insects. The characteristic feature of the NPVs is that many virions are embedded in each occlusion body, which is relatively large (up to 5 micrometers). Occlusion bodies of SNPVs (single nucleopolyhedrosis viruses) are smaller and contain a single virion with multiple nucleocapsids each. Multiple nucleopolyedrosis viruses (MNPVS) have multiple nucleocapsids per virion and multiple virions per occlusion body. Granulosis viruses (GVs) have a single virion with one nucleocapsid per occlusion body. The crystalline protein matrix of the occlusion bodies of these forms is primarily composed of a single 25 to 33 kDa polypeptide which is known as polyhedrin or granulin. Gröner et al. in *The Biology of Baculoviruses*, Vol. 1, supra, which is incorporated by reference herein, in Chap. 9, Tables 2 and 7 provides an extensive list of NPV hosts and GV hosts.

In nature, infection is initiated when an insect ingests food contaminated with baculovirus particles, typically in the form of occlusion bodies. The occlusion bodies dissociate under the alkaline conditions of the insect midgut, releasing the virions which then invade epithelial cells lining the gut. Pre-occlusion bodies are also infective (WO 97/08297, published Mar. 6, 1997). Within a host cell, the baculovirus migrates to the nucleus where replication takes place. Initially, specific viral proteins are produced within the infected cell via the transcription and translation of so-called "early genes." Among other functions, these proteins are required for the replication of the viral DNA, which begins 4 to 6 hours after the virus enters the cell. Viral DNA replication proceeds up to about 24 hours post-infection (pi). From about 8 to 24 hours pi, infected cells express "late genes" at high levels. These include components of the nucleocapsid which surround the viral DNA during the formation of progeny virus particles. Production of progeny virus particles begins around 12 hours pi. Initially, progeny virus migrate to the cell membrane where they acquire an envelope as they bud out from the surface of the cell. The nonoccluded virus particles can then infect other cells within the insect. Polyhedrin synthesis begins approximately 18 hours after infection and increases to very high levels by 24 to 48 hours pi. At about 24 hrs pi, there is a decrease in the rate of nonoccluded virus production, and most progeny virus particles are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects. [Reviewed in *The Biology of Baculoviruses*, Vol. I and II, Granados and Federici (eds.), CRC Press, Boca Raton, Fla., 1986].

Baculoviruses which are derivatives of AcMNPV and are useful as expression vectors have been described in U.S. Pat. No. 5,244,805 (Miller, issued Sep. 14, 1993); Rankin et al. (1988) *Gene* 70:39–49; Ooi et al. (1989) *J. Mol. Biol.* 210:721–736, Thiem and Miller (1990) *Gene* 91:87–95. Particularly strong late and very late promoters include the modified polyhedrin promoter LSXIV, the hybrid Cap/Polh promoter and the synthetic promoter Syn. However, there is a need for baculoviruses which cause insects to cease feeding earlier than prior art baculoviruses so that crop damage is minimized.

Baculoviruses with improved insecticidal properties have been described. For example, AcMNPV in which the egt (ecdysone glucosyl transferase) gene has been inactivated causes earlier cessation of feeding and earlier larvae death as compared to larvae infected with wild-type AcMNPV [See, e.g., U.S. Pat. No. 5,352,451 (Miller et al., issued Oct. 4, 1994].

Pyemotes tritici, the straw-itch mite, is one of thirteen known species of mites in the genus Pyemotes, all of which are predatory and which possess venoms causing mild to extreme toxicity in target insects. The thirteen known species can be divided into two morphological groups which also differ in host preference, methods of dispersal and toxicity to their target prey, and in the effects of their toxins on insects and man. The *scolyti* and *ventricosus* groups are summarized in Table 1. Most members of the *ventricosus* group have extremely insect-toxic venoms. The mite venoms do not appear to be specific for particular insects, since the venoms are toxic to a wide variety of insect host and nonhost species. However, the *P. tritici* toxins do not appear to be toxic to mammals.

Insect-specific toxins in the venom of *P. tritici*, have been purified and characterized [Tomalski et al. (1988) *Toxicon* 26:127–132; Tomalski et al. (1989) *Toxicon* 27:1151–1167]. These toxins are produced in female mites and injected into insect prey as components of the venom, resulting in paralysis of the prey, which allows the feeding female mite to become fully gravid, thus ensuring adequate nutrients for reproduction. The toxin designated TxP-I has been purified to apparent homogeneity; it has an apparent molecular weight of 27,000, as determined by SDS-polyacrylamide gel electrophoresis. Two other components were resolved which exhibit molecular weights of 28,000 and 29,000; these two components comprise TXP-II. Based on peptide mapping and immunoblot experiments, it was concluded that the protein components of TxP-I and TxP-II are isoproteins [Tomalski et al. (1989) supra]. DNA sequences encoding *P. tritici* toxin proteins have been isolated and characterized, and expressed in AcMNPV. See, e.g., U.S. Pat. No. 5,266,317, which is incorporated by reference herein in its entirety.

Insect-specific neurotoxins have also been found in the venoms of other arthropods including, but not limited to, scorpions, wasps and spiders [Zlotkin (1985) in *Comprehensive Insect Physiology, Biochemistry and Pharmacology*, I. Kerkut and L. I. Gilbert (eds.) Pergamon Press, Oxford, U.K., pp. 499–546]. Several insect-specific toxins (and corresponding coding sequences) from scorpions and other insect predators have also been described [See, e.g., EP 505 207 (published Sep. 23, 1992, Cayley et al.); Maeda et al. (1991) *Virology* 184:777–780; McCutchen et al. (1991) *Bio/Technology* 9:848–852; Stewart et al. (1991) *Nature* 352:85–88]. Merryweather et al. (1990) *J. Gen. Virology* 71:1535–1544 reported the construction of baculovirus containing the *Bacillus thuringiensis* subsp. *kurstaki* HD-73 delta endotoxin expressed the control of the polyhedrin promoter.

BRIEF DESCRIPTION OF THE FIGURES

FIGS. 1A–1E presents nucleotide and amino acid sequences of signal sequences tested with the itch mite toxin coding sequences. The signal sequences shown correspond to tox34 (FIG. 1A; nucleotides 12–137 of SEQ ID NO:1 and amino acids −39 to +3 of SEQ ID NO:2)),, sarcotoxin IA gene of *S. peregrina* (FIG. 1B; SEQ ID NO:10 and SEQ ID NO:11), the cuticle gene of *D. melanogaster* (FIG. 1C; SEQ ID NO:12 and SEQ ID NO:13), tox21A from *P. tritici* (FIG. 1D; nucleotides 119–199 of SEQ ID NO:3 fused to nucleotides 129–137 of SEQ ID NO:1 and amino acids 1 to 27 of SEQ ID NO:4 fused to amino acids 1–3 of SEQ ID NO:2) and a modified tox34 signal sequence (FIG. 1E; SEQ ID NO:14 and SEQ ID NO:15). The amino acid sequence of each signal peptide is highlighted by a shaded box below its corresponding nucleotide sequence. The mature N-terminus of tox34 is indicated by the amino acid residues in an open box. In the case of the sarcotoxin IA gene signal (FIG. 1B) a glycine residue was introduced onto the mature end of Tox34. Half arrows indicate the location and direction of PCR primers used to generate tox34 with the tox21A signal sequence (FIG. 1D). A shaded box in the nucleotide sequence of A shows the location of a complementary TAAG sequence which was mutated at the base pair marked by an asterisk in FIG. 1E.

FIGS. 4A–4B illustrate the effects of different promoters on Tox34 expression and secretion in TN-368 cells. Cell lysates (FIG. 4A) or supernatants (FIG. 4B) from TN-368 cells infected with the indicated viruses were harvested at the indicated times post infection. Proteins were separated by SDS-PAGE, blotted onto a membrane and probed with antibody directed against Tox34. Tox34 and its precursor (pTox34) form are indicated on the right.

FIG. 9A is a diagram of the HindIII restriction map of HzSNPV indicating the position of the IE-1 and polh genes [Cowan et al. (1994) *J. Gen. Virol.* 75:3211–3218]. FIG. 9B provides the nucleotide sequence of the 5' end of a 2.1 kB ClaI fragment of HindIII-C which contains the Bsu36I site(SEQ ID NO:22).

FIGS. 10A–10B provide the nucleotide sequence of HzS-NPV egt gene and the deduced amino acid sequence. The predicted translation start and stop codons and a potential polyadenylation site are in bold type. The SalI sites within the EGT coding sequences are indicated by double underlining. See also SEQ ID NOS: 23 AND 24.

FIG. 11B presents aligned amino acid sequences of baculovirus ecdysteroid UDP glucosyl transferases. The EGT sequences analyzed include those of (SEQ ID NO:24) HzNPV (SEQ ID NO:24) AcMNPV (SEQ ID NO:25) [O'Reilly and Miller (1990) *J. Virol.* 64:1321–1328]; *Buzura suppressaria* NPV, BsSNPV [Hu et al. (1997) *Virus Res.* 47:91–97]; *Bombyx mori* NPV, BmNPV (SEQ ID NO:26) [Genbank Accession No. L33180]; *Choristoneura fumiferana* NPV, CfMNPV (SEQ ID NO:27) and its associated defective virus, CfDEF (SEQ ID NO:28) [Barrett et al. (1995) *J. Gen. Virol.* 76:2447–2456]; *Lymantria dispar* NPV, LdMNPV (SEQ ID NO:29) [Riegel et al. (1994) *J. Gen. Virol.* 75:829–838]; *Mamestra brassicae* NPV, MbMNPV (SEQ ID NO:30) [Clarke et al. (1996) *J. Gen. Virol.* 77:2865–2871]; *Orgyia pseudotsugata* NPV, OPMNPV (SEQ ID NO:31) [Ahrens et al. (1997) *Virology* 229:381–399; Genbank Accession No. U75930]; *S. littoralis* NPV, SlMNPV (SEQ ID NO:32) [Faktor et al. (1995) *Virus Genes* 11:47–52] and *Lacanobia oleracea* GV, LOGV (SEQ ID NO:33) [Genbank Accession No. Y08294].

SUMMARY OF THE INVENTION

Figure 2A:
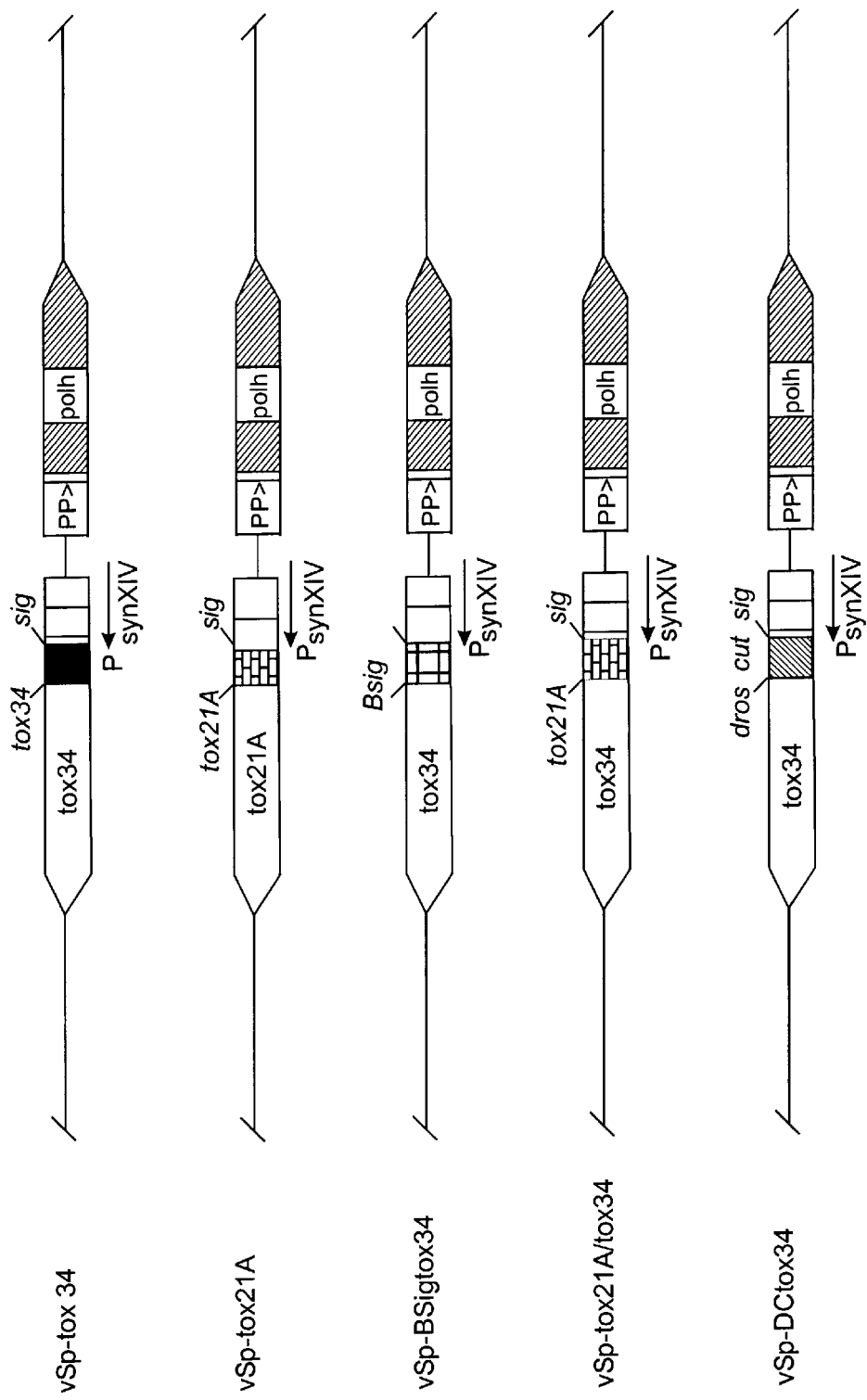
FIGS. 2A–2C presents schematic diagrams showing the polyhedrin gene region of baculovirus recombinants expressing tox34 with alternate signal sequences (FIG. 2A); under control of different promoters (FIG. 2B); and with a modified native tox34 signal sequence (FIG. 2C). The name of each virus is shown on the left. All recombinant viruses contain the toxin gene inserted into the AcMNPV genome upstream of and in the opposite orientation to the polyhedrin gene (polh) and its promoter (PP). The signal sequence (labeled above) and promoter used to drive toxin expression (labeled below with arrow) are shown for each recombinant.

It is an object of the present invention to provide baculoviruses which have been genetically engineered to contain and express insect-specific toxin genes under the control of promoters which allow the expression of the toxin coding sequence such that there is sufficient expression of the toxin sequence at a time earlier than enabled by prior art viruses, with the result that infected insects stop feeding and die sooner than with infection by prior art viruses. As specifically exemplified, the toxin genes expressed are those from insect-parasitic mites such as those of the genus Pyemotes, particularly those from *ventricosus* group of the Pyemotes. In a specific embodiment the insect-specific paralytic neurotoxin coding sequence is Tox34 derived from *Pyemotes tritici*; this coding sequence is provided in SEQ ID NO:1; a second specific embodiment of an insect paralytic neurotoxin coding sequence is termed Tox21a herein (SEQ ID NO:3; amino acid sequence, SEQ ID NO:4), also from *Pyemotes tritici*. It will be understood in the art that other insect-specific paralytic neurotoxin coding sequences from mites can be isolated and identified by nucleotide sequence homology, as determined in hybridization experiments [See, e.g., Hames and Higgins (1985) *Nucleic Acid Hybridization*, IRL Press, Washington, D.C.] employing sequence information provided herein. Insect-specific paralytic toxin coding sequences from insect-predacious mites which have at least 70% nucleotide sequence homology to the coding sequence in SEQ ID NO:1 and which encode toxins with substantially similar biology activity in insects are within the scope of the present invention.

As disclosed herein, the recombinant HzSNPV in which the itch mite toxin coding sequence is expressed under the regulatory control of the AcMNPV 6.9K promoter or a heat shock promoter, preferably from an insect heat shock gene or gene family such as hsp70, hsp83, hsp22 or hsp23. A preferred heat shock promoter is the *Drosophila melanogaster* hsp70promoter. The baculoviruses in which an insect-specific toxin gene is expressed under the control of a promoter such as the *D. melanogaster* hsp70promoter or the AcMNPV 6.9K promoter (or a DA26 promoter) are improved over prior art baculoviruses as insect control agents. These recombinant HzSNPV derivatives cause insect paralysis and death sooner than those constructs in which a mite toxin coding sequence is expressed under the control of very late promoters such as the polyhedrin promoter.

Genetically engineered baculoviruses for insect control other than the exemplified AcMNPV and HzSNPV can be produced using the teachings of the present Specification taken with what is well known to the art. Toxins other than those encoded by the tox34 and tox21a coding sequences can be inserted under the regulatory control of a heat shock promoter, preferably the hsp70promoter or 6.9K or a DA26 promoter as disclosed herein to produce killing properties when compared with baculoviruses in which the toxin coding sequences are inserted under the regulatory control of late or very late promoters.

The invention also includes a recombinant DNA molecule comprising a coding sequence for an insect-specific paralytic neurotoxin wherein said encoded insect-specific paralytic neurotoxin is expressed under the regulatory control of a heat shock promoter, preferably from an animal, more preferably from an insect, especially the Drosophila hsp70 promoter or the AcMNPV 6.9K promoter. A DA26 promoter can also be used. In particular, the hsp70 promoter is highly expressed in insect cells from a wide variety of species. Thus, genetically engineered baculoviruses expressing an insect-specific toxin under the regulatory control of this promoter are surprisingly improved in the time at which paralysis occurs and in terms of the insect species in which such a genetically engineered baculovirus is effective as an insect control agent. Particularly preferred embodiments of such a genetically modified baculovirus are those AcMNPV and HzSNPV derivatives which are occluded; preoccluded viruses are also useful in insect toxic compositions and methods for control of insect pests using same. For any example of a nonoccluded nuclear polyhedrosis or granulosis virus derivative, the skilled artisan understands how to construct an analogous occluded virus without the expense of undue experimentation.

Since there is significant homology among some genes of different baculoviruses, the skilled artisan will also understand how to insert the toxin gene, fused to an appropriate promoter, into the genomes of other baculoviruses in similar nonessential locations.

Accordingly, the invention includes a baculovirus which has been genetically modified to contain and express a gene encoding an insect-specific toxin, preferably a paralytic neurotoxin, under the regulatory control of a promoter which allows strong gene expression at a time relatively early after infection, especially as compared with other promoters such as that of the polyhedrin gene.

As specifically exemplified, the invention also provides a baculovirus which has been genetically modified to contain and express a coding sequence for an insect-specific paralytic neurotoxin of a mite of the genus Pyemotes, specifically from a mite of the species *Pyemotes tritici*. A specifically exemplified toxin coding sequence has a nucleotide sequence as given in SEQ ID NO:1 from an aspartate encoded at about nucleotide 120 to a cysteine encoded at about nucleotide 873. An alternative coding sequence for an insect-specific neurotoxin of an insect-predacious mite is that as shown in SEQ ID NO:3, from an aspartate encoded at about nucleotide 120 to a cysteine encoded at about nucleotide 873. Also within the scope of the present invention are mite toxin coding sequences having at least about 70% nucleotide sequence identity to the exemplified coding sequences as provided in SEQ ID NO:1 and SEQ ID NO:3.

As exemplified, the baculovirus derivative is an NPV baculovirus, specifically, an AcMNPV derivative or an HzSNPV derivative.

Another object of the invention is an insect-toxic composition comprising an insect-toxic amount of a baculovirus, genetically engineered to express an insect-specific paralytic neurotoxin at a level that results in a toxic effect on a targeted insect, and an agriculturally or otherwise environmentally acceptable carrier. Such compositions can be employed for protection of plants from insect pests. Preferred control agents are those which express an insect-specific paralytic neurotoxin gene from an insect-parasitic mite, and particularly those mites of the genus Pyemotes. It is preferred that the baculovirus particles are present in the occluded or preocculuded form. As specifically exemplified, the baculovirus derivative is an AcMNPV derivative or an HzSNPV derivative, and the recombinant baculovirus expresses an insect-specific toxin at an insect-toxic or insect-paralyzing level at a time sooner than that enabled by prior art viruses.

It is a further object of the invention to provide a method for the biological control of an insect pest comprising the step of applying an insect-toxic composition which contains an insect-toxic amount of a baculovirus which has been genetically engineered to express an insect-selective toxin gene such as an insect-specific paralytic neurotoxin gene from an insect-parasitic mite in an effective amount at a time earlier than enabled by prior art viruses. Such an insect-toxic composition is applied in the vicinity of a targeted insect, an insect habitat or to an area, plant or environment that is to be protected from the insect pest. The amount of said baculovirus derivative in said composition and the level of expression of said toxin coding sequence the baculovirus are such that said composition produces a toxic effect in a targeted insect, resulting in a reduction or, more preferably, a cessation of feeding. Preferred baculovirus derivatives include AcMNPV derivatives and HzSNPV derivatives. The occluded forms of genetically altered nuclear polyhedrosis viruses are most useful in the present invention. The skilled artisan understands that the genetically altered virus expressing the insect toxin may itself be capable of occlusion or that occlusion may be achieved by other means, e.g., by coinfection with an occlusion-positive virus. Useful promoters for toxin coding sequence expression include the heat shock promoters, preferably those from the animal kingdom, more preferably from an insect, and desirably from the hsp70, hsp83, hsp22 and hsp23 gene families, e.g., a *D. melanogaster* hsp70 promoter. Particularly preferred for use in the control of insect-specific toxin gene expression are those heat shock promoters which are relatively strongly constitutively expressed. However, a number of heat shock promoter sequences are well known and available to the art. Preferably, the insect toxin coding sequence is expressed under the regulatory control of the *Drosophila melanogaster* hsp70 promoter or the AcMNPV 6.9K promoter. The invention includes a method for the control of insect pests comprising the step of applying an insect-toxic amount of the insecticidal composition of the present invention to a habitat of said insect pests, for example, to plants.

Similarly, it is an object to provide baculoviruses which are genetically altered to express an insect-specific paralytic neurotoxin coding sequence, which are effective against insect pests other than those which attack or are harmful to plants. Such an agent can be incorporated into insect-toxic, insect-paralytic, or insecticidal compositions along with environmentally acceptable carriers as understood in the art, and can be used in a method to control a target insect pest susceptible to the particular baculovirus employed. For example, there are baculoviruses known to specifically infect each of mosquitoes and fleas. See, Beard et al. (1989) *J. Invertebrate Path.* 54:128–131 and Federici (1980) *Virology* 100:1–9. The target insect guides the ordinary skilled artisan in the selection of the particular baculovirus modified to express paralytic toxin.

Especially preferred in the recombinant baculoviruses, insecticidal compositions and methods of the present invention are those baculoviruses in which an insect-specific neurotoxin coding sequence is expressed and in which an ecdysteroid UDP-glycosyl transferase gene has been inactivated.

DETAILED DESCRIPTION OF THE INVENTION

A biological insect control agent is an agent effective in the control of insect pests. As used herein, insect control agents include baculoviruses which have been genetically modified to express an insect-specific toxin, preferably an insect-specific paralytic neurotoxin, in a way that leads to a cessation of feeding, insect paralysis or insect death at a time sooner than prior art baculoviruses due to the use of promoters which promote higher levels of toxin gene expression and at a time earlier than with previously described baculoviruses.

Control can refer to limitation of feeding behavior or to killing of an insect pest. A biological insect control agent of the present invention has an insect-toxic effect that is attributable at least in part to the expression of an insect-specific toxin coding sequence. An insect-toxic effect relates to any adverse effect on a targeted insect and is observable as paralysis and/or killing of that insect or as a change in normal behavior of the targeted insect such as in feeding behavior, righting response or other stereotypic behaviors. This toxic effect occurs due to early and efficient expression of such a toxin coding sequence.

Insect-predacious mites are those mites which feed on insects. Many of such mites inject venom into the insect hosts on which they feed. Such venom contains insect-specific paralytic neurotoxins to immobilize the host insects. Mites expressing insect-specific paralytic toxin genes include those within the *ventricosus* group including *P. anobii*, *P. beckeri*, *P. emerginatus*, *P. schwerdtfegeri*, *P. tuberculatus*, *P. tritici*, *P. ventricosus* and *P. zwoelferi*.

An insect-specific paralytic neurotoxin is a polypeptide which causes paralysis of a sensitive insect larva or adult, but has no significant toxic effect on other organisms. The paralytic effect may initially be observed as an effect on mobility or other behaviors of the insect, including feeding behavior. Insect-specific neurotoxins are those which adversely affect insects, and have negligible effects on higher animals, especially mammals. The insect-specific paralytic neurotoxin of this invention is specifically exemplified by Tox34 and Tox21a, and/or the TxP-I and TxP-II proteins produced by P. tritici. The deduced amino acid sequences for two representative insect-specific paralytic proteins are presented in SEQ ID NO:2 and SEQ ID NO:4. A toxin that is functionally equivalent to the neurotoxins of this invention effects a similar muscle contractile paralysis in insects as is caused by Tox34 and Tox21a. It is well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, Chapter 22, pages 345–352, incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Additional functional equivalents of insect-specific paralytic neurotoxins as defined herein include polypeptides with portions of amino acid sequences with substantial identity to Tox34 or Tox21a or polypeptides which themselves are a portion of a full length TXP-I protein or which have the amino acid sequence of a Tox34 or Tox21a protein into which an insertion has been made, and which retain the biological activity, in these examples, contractile muscle paralysis.

Insect-specific paralytic neurotoxin genes may be found in insect-predacious mites, including but not limited to those listed in Table 1, particularly those within the ventricosus group, or in other insect parasites or predators. Genes homologous to the tox34 and tox21a genes of the present invention may be identified in mites or other sources by nucleic acid hybridization to sequences disclosed in the present invention or by cross-reaction of toxin molecules with antibody specific for the toxins of the present invention or by any other means known to the art, including the use of PCR technology carried out using oligonucleotides corresponding to conserved or unambiguous regions of the toxin gene(s) exemplified herein. In principle, any insect-specific paralytic neurotoxin gene may be identified and that gene expressed in a baculovirus vector. Biological activity of the expressed protein can be readily determined and similarly, the efficacy of such a genetically modified vector can be assessed using the teachings of the present invention in combination with techniques well known to the art.

Other known insect-specific toxins include those from scorpions and spiders [see, e.g., Bougis et al. (1988) in *Proc. World Congress on Animal Natural Toxins*, pp. 94–101; EP 417,906; and EP 507,207]. Functional equivalents of published coding sequences and recombinant baculoviruses can be generated by the skilled artisan using techniques and information well-known to the art, e.g., in a manner similar to that described hereinabove for the mite toxins.

A recombinant DNA molecule, as used herein, does not occur in nature, and it is one which has been produced either by natural processes using known methods and directed by man to produce a desired result or artificially produced from parts derived from heterologous sources, which parts may be naturally occurring or chemically synthesized molecules, and wherein those parts have been joined by ligation or other means known to the art.

Genetically modified to contain and express an insect-specific toxin gene, such as an insect-specific paralytic neurotoxin gene, means that nucleotide sequences encoding such a protein and directing its synthesis are introduced into a baculovirus genome so that the modified baculoviruses can produce that neurotoxin protein. Any means known to the art may be used to insert the expressible neurotoxin gene into a particular baculovirus.

In the present invention, promoter and/or promoter-associated sequences direct gene expression, i.e., control transcription and translation of a nucleotide sequence encoding an insect-specific toxin in the infected target insect. Particularly preferred promoters are heat shock promoters such as those from the hsp70, hsp83, hsp22 and hsp23 gene families, especially the *Drosophila melanogaster* hsp70 promoter, and the AcMNPV (or other baculovirus) 6.9K promoter. Alternatively a baculovirus DA26 promoter can be used.

It will be understood that the goals of a skilled artisan will determine the choice of particular regulatory sequences and/or promoters. For example, with baculovirus promoters, if high levels of expression are required, then an especially strong promoter, expressed at a very early time after infection and in a wide variety of insect cells, is appropriate. This is consistent with the goal of limiting the feeding of an insect larva to the shortest possible time (or to extend the effective host range of the insect virus).

An NPV baculovirus isolated from *Autographa californica* (Lepidoptera: Noctuidae), specifically AcMNPV, is exemplified in the present disclosure. The terms AcMNPV and AcNPV are synonymous. The infectivity of most NPVs is reported to be restricted to members of the genus, family or order of the original host. AcMNPV baculoviruses replicate in several families of Lepidoptera, but their infectivity is reported to be limited to that order. A second specifically exemplified baculovirus modified to achieve improved efficacy as an insecticide, is HzSNPV, which was isolated from the cotton bollworm, *Helicoverpa zea*. HzSNPV infects and kills most species of Helicoverpa (Heliothis). In the mid 1970s, HzSNPV was registered and commercially produced as a pesticide (Elcar™) by Sandoz Corp. to control infestations of the cotton bollworm [Ignoffo, C. M. (1981) Living Microbial insecticides. In: *Essays in Applied Microbiology* (eds. J. R. Norris and M. H. Richmond) John Wiley & Sons, New York, pp. 2–31]. This product, however, did not compete successfully with the newly introduced pyrethroid pesticides. The poor field performance of Elcar™ was due, in part, to the slow rate that the virus killed the insect pest compared to contact chemical pesticides; the delay between virus application and insect death can result in significant crop damage [reviewed by Miller, L. K. (1995) *J. Invertebr. Pathol.* 65:211–216].

The art understands how to insert an expressible gene into a viral genome at a site which does not interfere with viral replicative functions. Similarly, the skilled artisan can select a promoter with desired strength and temporal expression to drive the expression of an insect-specific toxin gene in a desired baculovirus vector. The target insect dictates the virus selected, and the particular virus to be engineered will guide the skilled artisan in the selection of an appropriate promoter.

A number of promoters have been used to control the expression heterologous coding sequences in recombinant baculovirus systems. The three classes of viral promoters for viruses such as AcMNPV are early, late and very late promoters [see, e.g., Morris and Miller (1992) *J. Virol.* 35 66:7397–7405]. Early promoters include the ETL promoter of AcMNPV, which has been described in U.S. Patent No. 5,266,317, the DA26 promoter and the IE0, IE1 and IEN promoters [O'Reilly et al. (1990) *J. Gen. Virol.* 71:1029–1037; Carson et al. (1991) *J. Virol.* 65:945–951; Kovacs et al. (1991) *J. Virol.* 65:5281–5288. Late AcMNPV promoters include 6.9K, the capsid (vp39) promoter [Hill-Perkins and Possee (1990) *J. Gen. Virol.* 71:971–976; Thiem and Miller (1989) *J. Virol.* 63:2008–2018]. Very late promoters include the polyhedrin and a synthetic promoter [U.S. Pat. No. 5,244,805, L. Miller, issued 1993] and the modified polyhedrin promoter LSXIV [Ooi et al. (1989) *J. Molec. Biol.* 210:721–736; U.S. Pat. No. 5,244,805 (L. Miller, issued 1993]. Very late baculovirus promoters, as exemplified in AcMNPV, include the polyhedrin and p10 promoters [Kelly and Lescott (1981) *Microbiologica* 4:35–57; Miller, L. K. (1988) *Ann. Rev. Microbiol.* 42:172–199; Bonning et al. (1994) *J. Gen. Microbiol.* 75:1551–1556]. See also Thiem and Miller (1990) *Gene* 91:87–94 for further discussion of late and very late gene expression. See also *The Baculoviruses*, ed., L. K. Miller, Plenum Press, New York, 1997.

A heat shock promoter with a significant level of constitutive expression of a downstream, operably linked coding sequence is exemplified by hsp70 promoters, in particular, the *D. melanogaster hsp*70 promoter [See, e.g., Toerek and Karch (1980) *Nucl. Acids Res.* 8:3105–3123]. This promoter has been used for the expression of heterologous coding sequences in recombinant baculovirus vectors with varying degrees of success [Morris and Miller (1992) supra].

For a general discussion of heat shock genes, their promoters and heterologous expression driven by them, see, e.g., Nover, L. (1987) *Enzym. Microb. Technol.* 9:130–144; Amin et al. (1988) *Mol. Cell. Biol.* 8:3761–3760, and references cited in said references, all of which are incorporated by reference herein in their entireties. It is a general property of hsp70, in Drosophila and in other organisms that there is a relatively high constitutive level of downstream gene expression. hsp70 promoter and promoter-associated sequences from a variety of insect, animal, plant and yeast sources are well known in the art.

In the context of the present application, a recombinant DNA molecule is produced via human intervention, and it contains nucleotide sequences which in nature are not covalently joined or associated. Chemical synthesis or in vitro enzyme ligation can effect the joining, or recombination can be accomplished where the input sequences are introduced into a single cell in the laboratory and predicted resulting progeny are analyzed and purified.

As used herein, an insect control agent is a composition or the active ingredient of a composition which has an adverse affect on insect pests. Feeding by insects is reduced in response to the genetically engineered baculoviruses of the present invention as a result of the expressed toxin, and death of the insect follows. An insect control agent of this invention preferably is an insect virus genetically engineered to express a heterologous gene encoding an insect-specific toxin. Specific examples of such toxin proteins include, but are not limited to, Tox34 and Tox21a, with the amino acid sequences disclosed in SEQ ID NO:2 and SEQ ID NO:4, respectively, as well as known scorpion and spider toxins.

Figure 8:
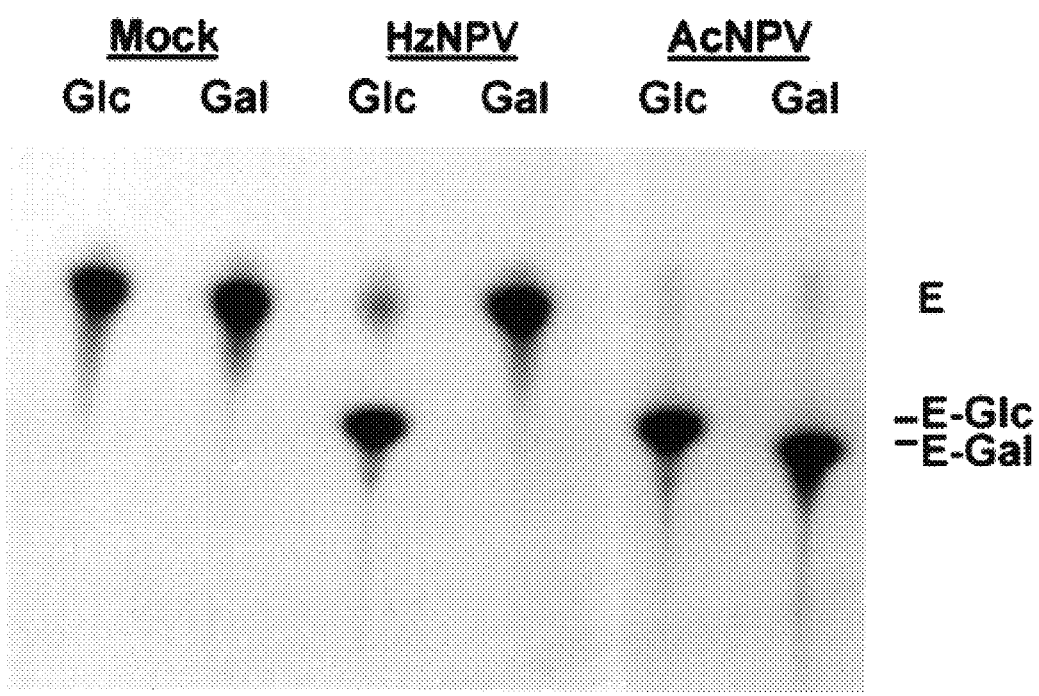
FIG. 8 shows the results for an assay of EGT activity in the culture supernatants removed from infected Hz cells. Cells were either mock infected or infected with HzSNPV or AcNPV. UDP-glucose (Glc) or UDP-galactose (Gal) were used as substrates. The products of the reactions were separated from the substrates by thin layer chromatography. The position of the [$^3$H] ecdysone substrate is indicated (E) on the right as are the positions of the ecdysone-glucose (E-Glc) or ecdysone-galactose (E-Gal) products.

To determine if HzSNPV possessed and expressed an egt gene, the presence of EGT activity in supernatants from uninfected and infected HzUNDK cells was determined by enzymatic assays using [$^3$H] ecdysone and UDP-glucose or UDP-galactose as substrates. Using UDP-glucose as a substrate, the supernatants from ACMNPV- and HzSNPV-infected cells converted ecdysone to a product of altered polarity which was previously identified as an ecdysone-glucose conjugate (FIG. 8). This EGT activity was not observed in uninfected HzUNDK cells, indicating that HzSNPV induced an EGT activity during infection and possessed an egt gene. When UDP-galactose was used as a substrate, the EGT activity in AcMNPV-infected cell extracts was able to form an ecdysone-galactose conjugate, but HzSNPV-infected cells were unable to use UDP-galactose as a substrate (FIG. 8), indicating a difference in the substrate specificities of the AcMNPV and HzSNPV EGTs [O'Reilly et al. (1992) *Insect Biochem. Molec. Biol.* 22:313–3201.

Figure 11A:
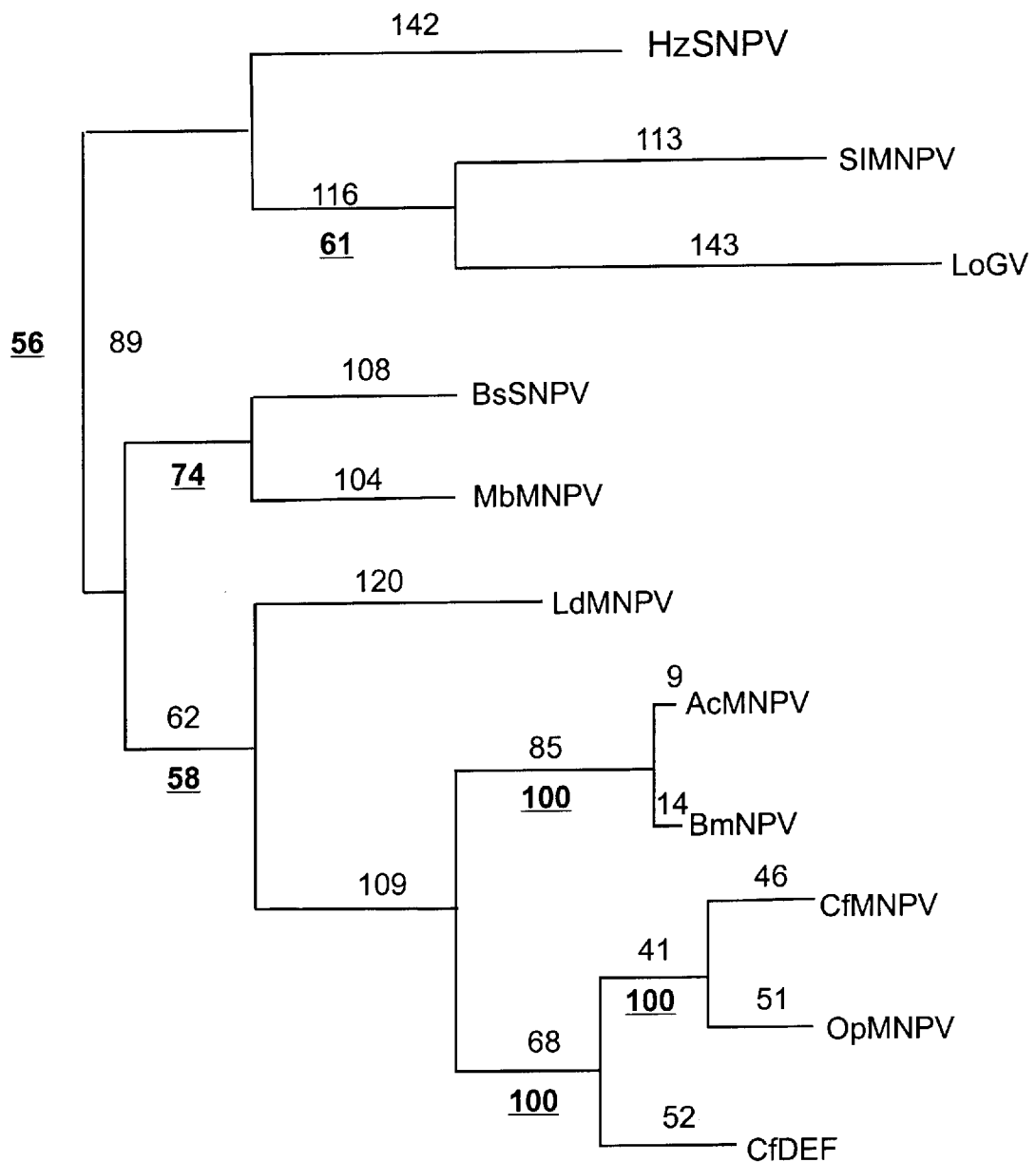
FIG. 11A is a phylogenetic tree of baculovirus ecdysteroid glycosyl transferases for which sequence information is available. The single most parsimonious tree with length of 1538 and a consistency index of 0.81 was constructed using the Branch and Bound Search program of Paup 3.1 [Swofford, D. L. (1993) Phylogenetic analysis using parsimony. Version 3.1, computer program distributed by the Illinois Natural History Survey, Champaign, Ill.]. Numbers above the lines are the number of changes between the node and virus, while the underlined numbers below the lines indicate the frequency of that cluster after bootstrap analysis with 100 replicates.

Restriction digests of the Elcar isolate of HzSNPV were identical to those isolates previously described bv Knell and Summers (1984) *J. Gen. Virol.* 65:445–450 and Cowan et al. (1994) *J. Gen. Virol.* 75:3211–3218. A set of overlapping cosmids representing the entire HzSNPV genome was isolated and characterized. The basic physical map of the HzSNPV genome was confirmed and further refined (FIG. 9A). The genes in the polyhedrin gene (polh) region, e.g. the IE1 gene, are known to be in reverse order to that of the conventional AcMNPV map [Cowan et al. (1994) supra]. Using the ACMNPV egt gene as a hybridization probe on Southern blots failed to give a strong hybridization signal under the conditions used. As an alternate approach to mapping the egt gene, cosmid plasmid clones corresponding to regions flanking the polh gene were screened by PCR using degenerate oligonucleotide primers which were constructed based on consensus sequences from conserved regions of the egt gene. PCR amplification using an HzSNPV cosmid which spanned HindIII-J through -E fragments and a plasmid clone containing the HindIII-C fragment as templates generated a PCR product of the size expected for the egt gene. One of the PCR products was cloned and sequenced and found to contain a portion of the egt gene. The sequences generated were used to prepare oligonucleotide primers which allowed the sequencing of the entire HzSNPV egt gene. The egt gene was located entirely within the EcoRI Q fragment (FIG. 9A) and is transcribed from the same strand as the polh and IE1 genes. The DNA sequence of HzSNPV egt is presented in FIGS. 10A–10B; see also SEQ ID NOs: 23 and 24. The percent sequence identity and similarity of HzSNPV EGT with other known EGTs are presented in Table 7, and FIG. 11 presents a phylogenetic tree based on amino acid sequence comparisons of several baculoviral egt genes.

The HzSNPV genome was found to have no Sse8387I sites and a single Bsu36I site which was located within the HindIII-C fragment (FIG. 9A). The sequence surrounding this restriction site was determined (FIG. 9B). The region contained no open reading frames (ORFS) of 50 codons or more and exhibited no homology with other known viral genes by computer analysis. This site was eliminated from the virus genome by restriction digestion, filling-in the 3 bp cohesive ends, and religation. The infectivity and virulence of the resulting virus lacking the Bsu36I site, HzSNPV (Bsu36I'), was determined by measuring the $LC_{50}$s and ET$_{50}$s, respectively, in *H. zea* neonates. Duplicate LC$_{50}$ assays (Tables 6 and 7) showed that the elimination of the Bsu36I site had little or no effect on the infectivity of the virus, and duplicate ET$_{50}$ assays (Tables 8 and 9) showed that the virulence of the modified virus was also essentially unaltered. The Bsu36I' virus was then used for the construction of all subsequent virus constructions since the ability to insert genes into the viral genome by direct cloning offers a rapid and useful means of constructing viral recombinants [Ernst et al. (1994) *Nucl. Acids Res.* 22:2855–2856; Lu and Miller (1996) *Biotechniques* 21:63–68] and insertion of Bsu36I and Sse8387I sites into the egt region of the Bsu36I' virus simplifies direct cloning into this region.

The next step in genetically engineering HzSNPV was to insert a marker gene, the *E. coli* GUS gene, into the egt gene of HzSNPV and screen for viruses which produced a blue color in the presence of the GUS indicator, X-Gluc (see Example 4). This virus was then used as a parental virus to construct additional HzSNPV recombinants using the presence of white plaques as a screen for double-crossover recombinants in allelic replacement.

Figure 7:
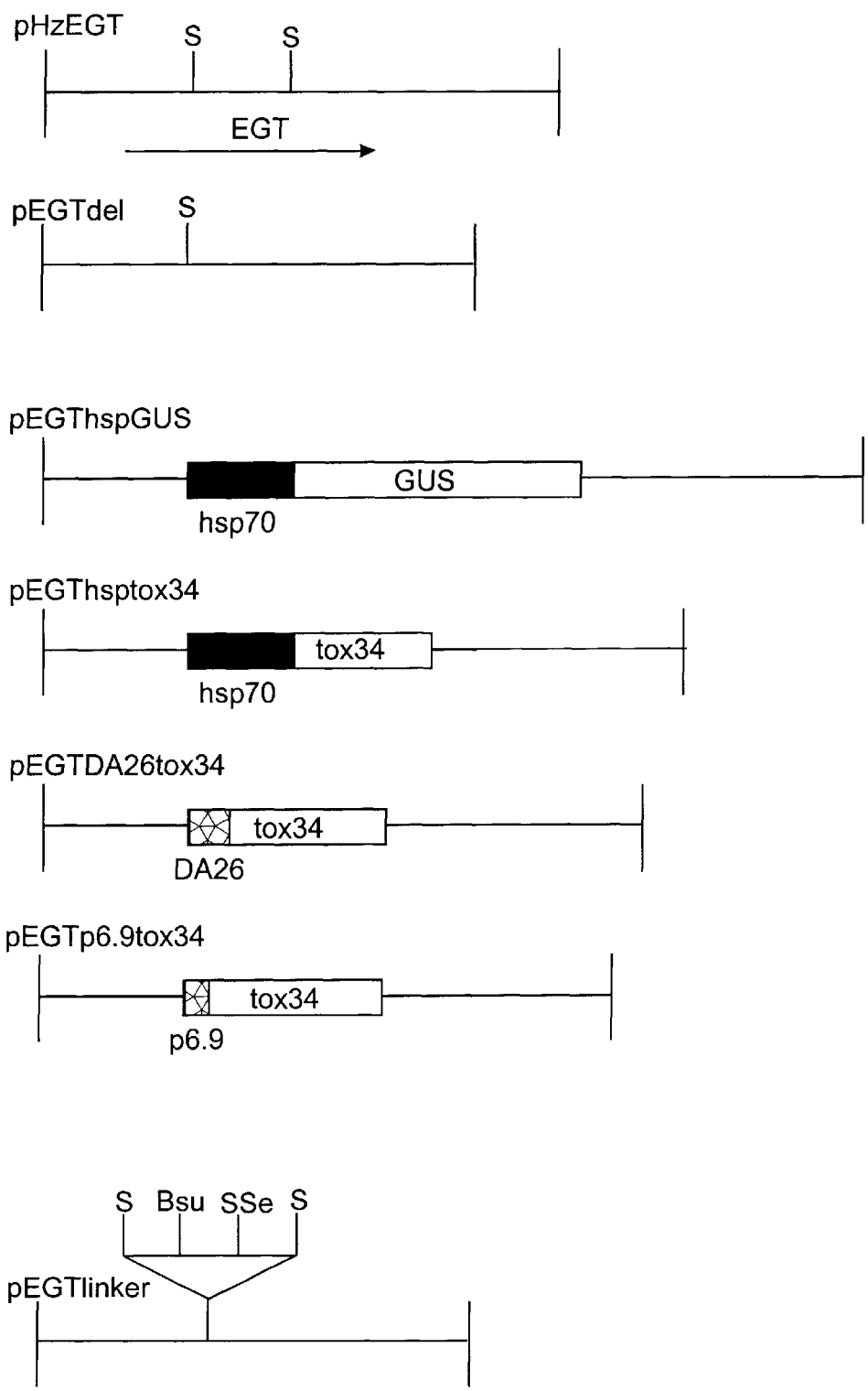
FIG. 7 is a diagram showing the plasmid transfer vectors used to construct recombinant HzSNPV viruses. Plasmid pHzEGT contains a complete egt gene while all others contain deletions and/or insertions in the egt gene. Viral sequences were inserted at the EcoRI site of pbluescript KS on the left while the junction at the right is a fusion of a viral SalI site and the vector XhoI site. Restriction sites indicated with the viral DNA inserts are SalI (S) , Bsu36I (Bsu) and Sse8387-T (Sse). Promoters (hsp70, DA26 or p6.9) are shown by shaded or dark boxes while the foreign gene insert (GUS or tox34) are indicated by open boxes.

An egt deletion virus, three tox34-expressing recombinant viruses and an egt deletion virus containing Bsu36I and Sse8387I sites within the egt locus were constructed by allelic replacement using the appropriate transfer plasmids (see FIG. 7). Each of the tox34-expressing recombinants contained a different promoter: the *D. melanogaster* hsp70 promoter, the early AcMNPV DA26 (ORF 16) viral promoter or the late AcMNPV p6.9 gene (ORF 100) promoter. The infectivities and virulence of these toxin-expressing viruses were compared to HzSNPV, HzSNPV (Bsu36I') and egt deletion mutant (HzEGTdel) virus in *H. zea* neonates (Tables 8–11). The LC$_{50}$s were found to be similar, if not identical, for all the viruses tested. All viruses containing tox34 had significantly lower ET$_{50}$s, indicating that all three promoters used were functional in *H. zea* larvae and that toxin gene expression reduced the ET$_{50}$s substantially. The recombinant expressing tox34 under the control of the viral DA26 promoter exhibited a lower ET$_{50}$ than the recombinant containing the tox34 gene under the control of the Drosophila hsp70 promoter in this species. The AcMNPV p6.9 promoter also consistently performed better than the hsp70 promoter and was similar to, although possibly slightly less effective than, the AcMNPV DA26 promoter. The vEGTDA26tox34 virus decreased the ET$_{50}$ to less than 40 h, 40% less than wt HzSNPV. The ET$_{50}$s for HzEGTdel was not lower than those for HzSNPV wt and HzSNPV (Bsu36I').

The HzSNPV egt gene is located between 93.1 and 94.5 m.u. of the HzSNPV map and is predicted to encode a 515 amino acid polypeptide with less than 50% sequence identity with other known baculovirus EGTs. Like other baculovirus egt gene products [O'Reilly et al. (1992) *Insect Biochem. Molec. Biol.* 22:313–320], it is predicted to have a cleavable signal sequence at its amino-terminus and lacks a C-terminal transmembrane domain. The HzSNPV EGT has the seven amino acids which are found to be absolutely conserved among all EGTs and UDP-glycosyltransferases [O'Reilly, D. R. (1995) *Insect. Biochem. Molec. Biol.* 25:541–550]. Domain II of EGTs [O'Reilly (1995) supra] from amino acid residues 254–267, is the most conserved region among all baculovirus EGTs including the HzSNPV EGT. In contrast to the AcMNPV EGT [O'Reilly et al. (1992) *Insect Biochem. Molec. Biol.* 22:313–320], the HzSNPV EGT is unable to use UDP-galactose as a substrate. The site for UDP-sugar binding is predicted to lie within domains III and IV of the EGT polypeptides (O'Reilly (1995) supra]. HzSNPV EGT shares the most sequence identity to the MbNPV EGT (70%) and the most similarity to SlNPV (Table 7; see also FIG. 11A for phylogenetic tree).

Although deletion of the AcMNPV egt gene reduced the LT$_{50}$ of this virus in two different species [O'Reilly and Miller (1991) *BioTechnology* 9:1086–1089], a similar reduction in the rate of mortality was not observed for the HzSNPV egt deletion mutant in *H. zea* neonate larvae. Because wild-type HzSNPV acts more quickly than wild-type AcNPV in its respective host, the effect of egt (e.g. 15% reduction in LT$_{50}$) appears too subtle to be observed in this species or in this larval instar. Expression of egt is known to block the molting of the host insect [O'Reilly and Miller (1991) supra] and also prevents the degeneration of the malpighian tubules during the infection process [Flipsen et al. (1995) *J. Virol.* 69:4529–4532].

Promoter-dependent effects on tox34 expression and larval paralysis have been previously reported in AcMNPV [Tomalski and Miller (1992) *BioTechnology* 10:545–549; Lu et al. (1996) *BioTechniques* 21:63–68]. Both the Drosophila hsp70 and viral p6.9 promoters were considerably more effective than the polh promoter in reducing the ET$_{50}$ of AcMNPV in both *T. ni* and *S. frugiperda*, and the relative effectiveness of the p6.9 and hsp70 promoters was species-dependent [Lu et al. (1996) *Biol. Control.* 7:320–332]. The DA26 promoter, however, was less effective in reducing the ET$_{50}$ of AcMNPV in these two species than the polh, p6.9 or hsp70 promoters. We compared the effects of placing tox34 under the control of Drosophila hsp70, AcMNPV DA26, or AcMNPV p6.9 promoters within the context of the HzSNPV genome in *H. zea* neonates and found that all toxin-expressing recombinant viruses had a reduced effective time to paralysis/mortality relative to wt HzSNPV. The most effective viral promoter was AcMNPV DA26 although it was only slightly more effective than the AcMNPV p6.9 promoter. The *D. melanogaster* hsp70 promoter was somewhat less effective under these conditions than either the hsp70 or DA26 promoters. Both early and late AcMNPV promoters were effective in the context of the HzSNPV genome. Without wishing to be bound by theory, it is predicted that the equivalent HzSNPV promoters are as or more effective than the AcMNPV promoters.

We have successfully improved the properties of HzSNPV as a pesticide through genetic engineering technology to provide the first recombinant HzSNPV. With an ET$_{50}$ of less than 40 hrs, the HzDA26tox34 recombinant is the fastest acting baculovirus reported to date. Genetically engineered HzSNPV derivatives are also useful as gene expression vectors.

The mature form of the Tox34 protein secreted from insect cells infected with recombinant AcMNPV expressing tox34 [Tomalski and Miller (1991) *Nature* 352:82–85] is thought to be the same form as that produced by mites. TxP-I is synthesized as a precursor protein of 291 amino acids; the first 39 amino acids are a signal sequence absent from the mature secreted product. Since mature Tox34 is a secreted protein that must interact with the secretory pathway of infected insect cells, we investigated the influence of different signal peptides on expression and secretion of Tox34. Secretion of some heterologous proteins from baculovirus-infected cells appears to be affected by the nature of the signal sequence [Tessier et al. (1991) *Gene* 98:177–183; O'Reilly et al. (1995) *Insect Biochem. Mol. Biol.* 25:475–485].

Figure 2B:
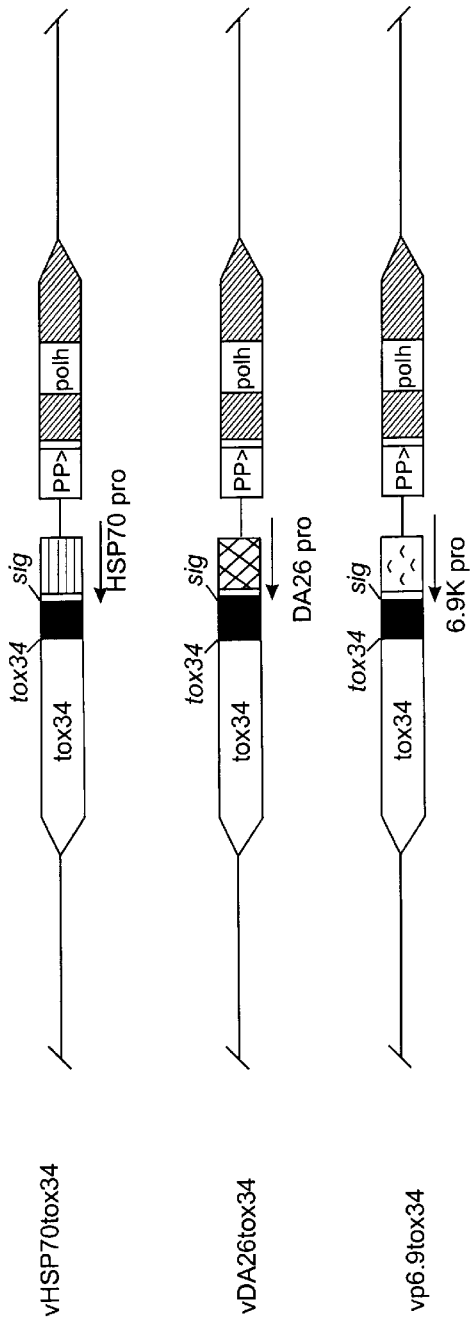
Figure 2C:
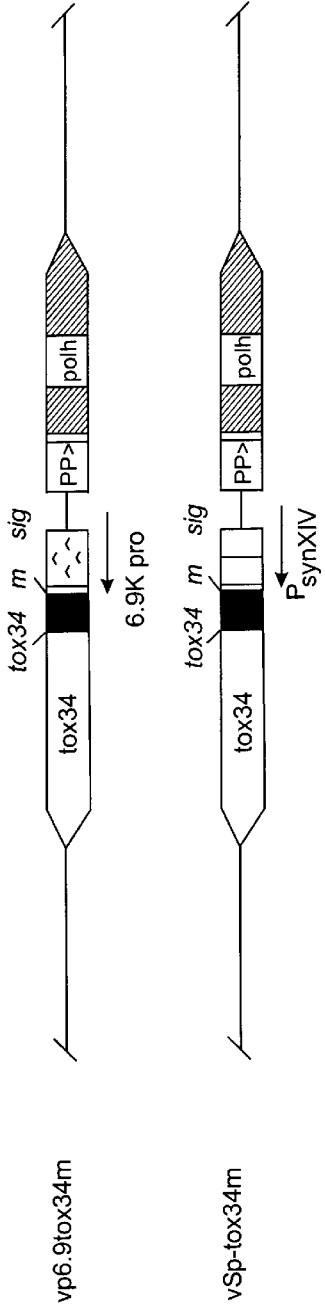
Figure 3:
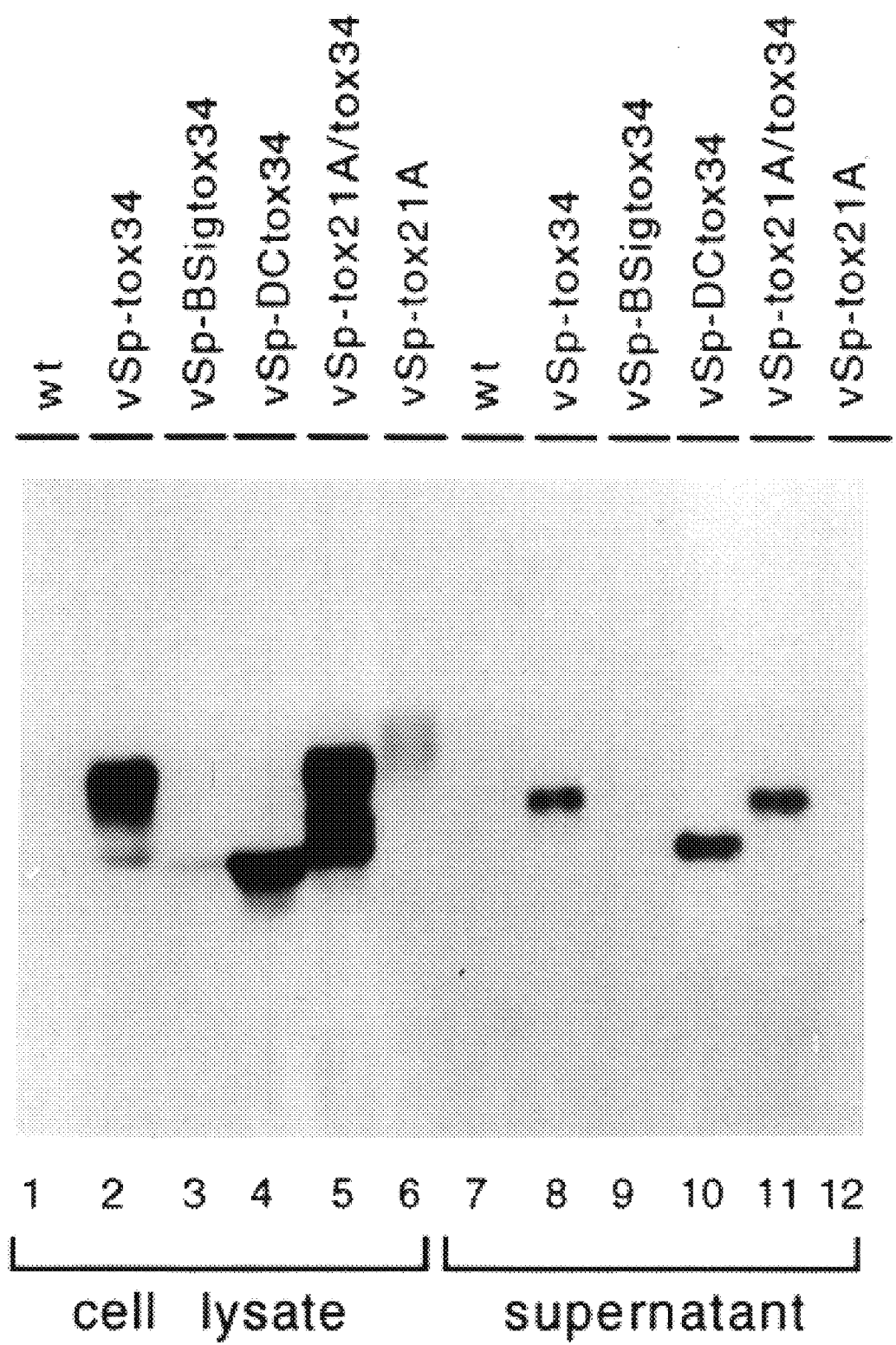
FIG. 3 illustrates the effect of different insect signal sequences on expression and secretion of Tox34 in SF-21 cells. Cell lysates (lanes 1 to 6) or supernatants (lanes 7 to 12) from SF-21 cells infected with the indicated viruses were harvested at 48 h post infection (p.i.) and the proteins were separated by SDS-PAGE and visualized by immunoblotting.
Figure 5:
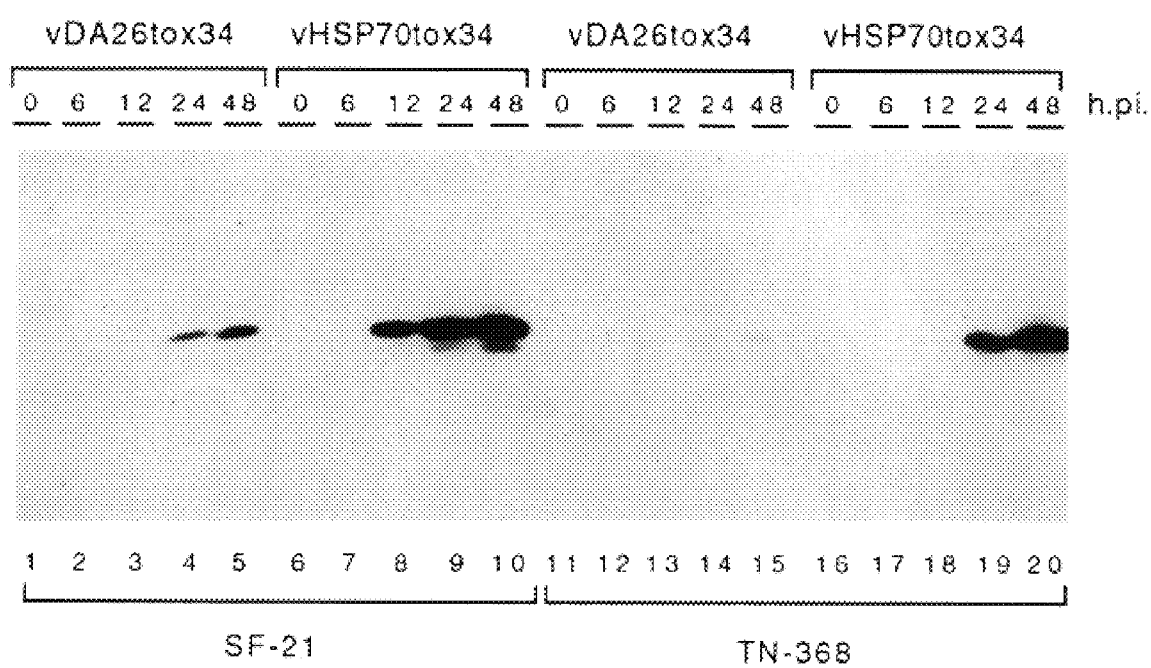
FIG. 5 provides a comparison of the secreted levels of Tox34 from vDA26tox34- or vHSP70tox34-infected SF-21 or TN-368 cells. SF-21 (lanes 1 to 10) or TN-368 (lanes 11 to 20) cells were infected with vDA26tox34 or vHSP70tox34, and supernatants were collected at the indicated times p.i. Proteins in the supernatant fractions were concentrated, separated by SDS-PAGE and blotted onto a membrane. Tox34 was detected using an antibody specific for purified Tox34.
Figure 6A:
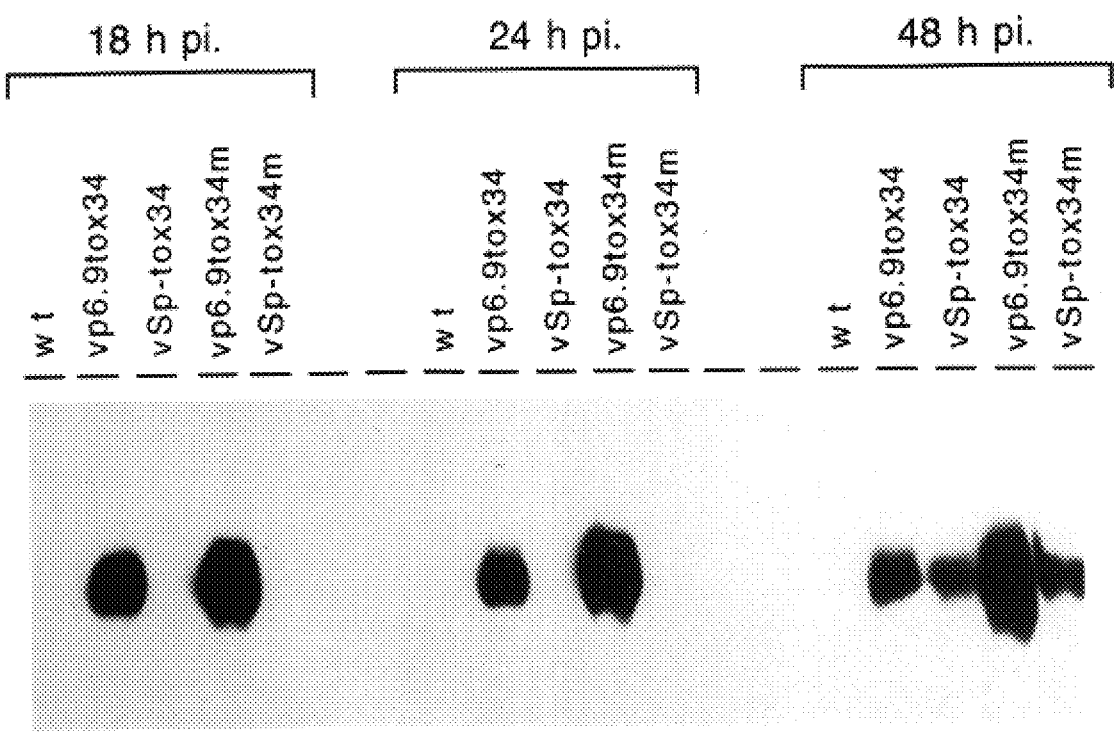
FIGS. 6A–6B illustrates the effects of the complementary TAAG sequence in the native tox34 signal sequence on expression and secretion of the Tox34 protein. Proteins in cell lysates (FIG. 6A) or supernatants (FIG. 6B) from TN-368 cells infected with the indicated viruses at 18, 24 and 48 h p.i. were separated by SDS-PAGE, transferred onto membranes, and probed with anti-Tox34 antibody.
Figure 6B:
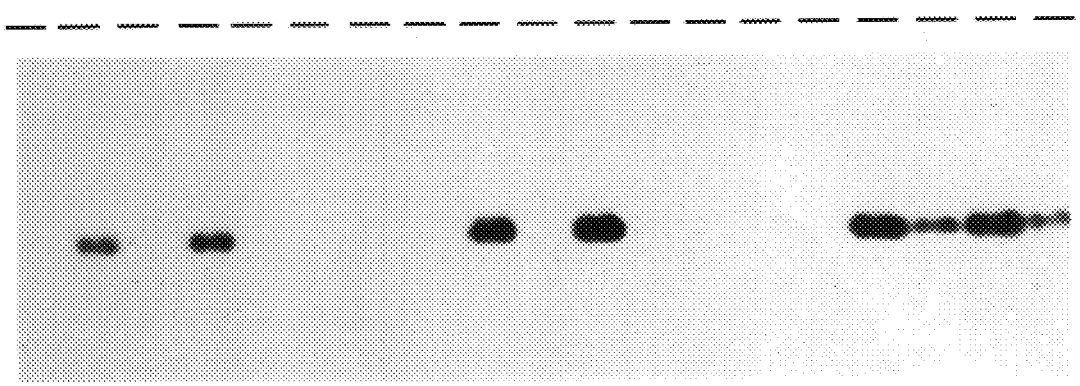

Three different signal sequences derived from the sarcotoxin IA gene of *Sarcophaga peregrina* (flesh fly), the cuticle gene of *D. melanogaster*, and a homolog of tox34 (tox21A) were substituted for the native tox34 signal sequence (see FIGS. 1A–1E) and placed under control of the modified polyhedrin promoter $P_{synXIV}$ in AcMNPV (FIG. 2A–2C). The levels of Tox34 expressed in recombinant virus-infected SF-21 cells and secreted into the tissue culture media at 48 h pi were compared by Western blot analysis using polyclonal antibody specific for Tox34 (FIG. 3). Intracellular levels of toxin produced at 48 h p.i. varied (FIG. 3, lanes 1–6). Expression from vSp-BSigtox34 produced less intracellular toxin protein (FIG. 3, compare lanes 2 and 3) while vSp-DCtox34 and vSp-tox34 infected-cells produced similar amounts of intracellular toxin (FIG. 3, compare lanes 2 and 4). In contrast, intracellular levels of toxin in vSp-tox21A/tox34 infected cells were approximately 3-fold higher than in vSP-tox34 infected cells (FIG. 3, lanes 2 and 5). No Tox34 was detected in wild-type AcMNPV infected cells (FIG. 3, lane 1). The 15-fold reduction of intracellular toxin in vSp-tox21A infected cells relative to vSp-tox34 (FIG. 3, lane 6) probably reflects inefficient recognition of Tox21A by the Tox34 antibody. Toxin produced in and secreted from cells infected with vSp-BSigtox34 and vSp-DCtox34 appear to be about 5 kDa smaller than Tox34. Without wishing to be bound by any particular theory, this is believed to represent differences in the site or efficiency of cleavage governed by the alternate signal sequences. The N-terminal sequence of TXP-I is known [Tomalski et al. (1989) *Toxicon* 27:1151–1167]; the N-terminal sequence of mature recombinant Tox34 has not be empirically determined.

The heterogeneity in sizes of intracellular Tox34 in vSp-tox21A/tox34 infected cells has been observed previously [Tomalski and Miller (1991) *Nature* 352:82–85; Tomalski and Miller (1992) *Bio/Technology* 10:545–549] and probably represents precursors of the mature Tox34 protein. The ratio of the precursor to the mature forms of Tox34 increases with time p.i. [Tomalski and Miller (1992) supra], likely reflecting the fact that the cell's secretory pathway becomes functionally compromised during the later phases of infection [Jarvis et al. (1993) *J. Biol. Chem.* 268:16754–16762]. Because there are 3-fold higher levels of toxin expressed in cells infected with vsp-tox21A/tox34 than with vSp-tox34, the presence of these heterogenous products suggests that the former is expressed at higher levels than the latter and/or that the tox21A signal sequence is not efficiently processed. Both scenarios can lead to an accumulation of unprocessed forms of Tox34 in vSp-tox21A/tox34 infected cells.

None of the changes to the signal sequence of tox34 ultimately increased the amount of secreted toxin. The amount of Tox34 secreted by vSp-tox34, vSp-DCtox34, and vSp-tox21/tox34 infected cells at 48 h p.i. was similar (FIG. 3, lanes 8, 10, 11) while Tox34 was undetectable in the supernatant fractions of vSp-BSigtox34 and vSp-tox21A infected cells (FIG. 3, lanes 9 and 12). Again, and without wishing to be bound by any particular theory, the apparent absence of Tox21A is believed to be due to poor reactivity with the Tox34 antibody. The low levels of secreted toxin from vSp-BSigtox34 infected cells is believed due to translational or post-translational problems since the levels of the toxin transcripts appear to be similar. The additional glycine residue added to the N-terminal sequence of the mature toxin may be responsible for this effect.

Neonate *T. ni* larvae were infected per os with occluded virus from each recombinant virus to evaluate the effect of changing the signal sequence of tox34 on the $LC_{50}$ (concentration of occluded virus required to kill 50% of the test insects) and the $ET_{50}$ (time required to paralyze or kill 50% of the test insects) of each recombinant virus (Table 2).

No significant differences in the $LC_{50}$ for the different viruses were observed; thus, the expression of tox34 does not compromise ability to initiate infection relative to wild-type. In all cases, per os infection of *T.ni* larvae by tox34 expressing viruses resulted in paralysis. vSp-tox34 and vSp-DCtox34 infected larvae were paralyzed approximately 50% faster than wild-type AcMNPV, vSp-tox21A and vSp-tox21A/tox34 about 35% faster than wild-type, and vSp-BSigtox34 about 25% faster. The $ET_{50}$ of vSp-tox34 is in close agreement with previously published results [Tomalski and Miller (1992) supra]; however, the $ET_{50}$ of vSp-tox21A is approximately 15 h longer than what was reported for the same construct by Tomalski et al. (1993) *Toxicon* 31:319–326.

The $ET_{50}$ values for vSp-tox34 and vSp-DCtox34 correlate well with the levels of toxin detected in the supernatants of infected cells; however, the $ET_{50}$ of vSp-tox21A/tox34 was longer than vSp-tox34 and vSp-DCtox34 even though similar levels of toxin were secreted. This suggests that not all of the secreted toxin from vSp-tox21A/Tox34 infected cells is biologically active. Although no toxin was found in the supernatant from vSp-BSigtox34 infected cells, neonate *T. ni* larvae infected per os with vSp-BSigtox34 exhibited paralysis, indicating that the threshold level of toxin required for paralysis of *T. ni* neonates is low or that some insect tissues are more efficient in producing active toxin from this construct. Fourth instar *T. ni* injected hemocoelically with $2.0 \times 10^5$ pfu of vSp-BSigtox34 exhibited paralysis after 48 h. In general, the level of toxin secreted into culture supernatant was predictive of virus performance in vivo.

S1 nuclease analysis was performed to determine whether the low level of toxin produced by vSp-BSigtox34 infected cells was at the level of transcription or translation. A 648 bp or a 668 bp HindIII-NdeI probe, uniquely end-labeled at the NdeI site, was used in S1 nuclease protection assays with total RNA isolated from vSp-BSigtox34 or vSp-tox34 infected cells at 0, 6, 12, 24 and 36 h p.i. Protected probe corresponding to transcriptional initiation within the TAAG motif of the $P_{synXIV}$ promoter was observed as early as 12 h p.i., and continued to increase through 36 h p.i., with RNA prepared from both vSp-BSigtox34- and vSp-tox34-infected cells. The amount of protected probe at each time point was similar between the two viruses, indicating that the low level of toxin produced in vSp-BSigtox34 infected cells was not due to reduced transcription.

Interestingly, another transcriptional start site was mapped to a TAAG sequence on the complementary strand within the native tox34 signal sequence which was not present in RNA isolated from vSp-BSigtox34 infected cells. Primer extension analysis confirmed that this additional start site corresponded to the reverse TAAG motif. Similar interference from duplex RNA in S1 nuclease and primer extension analysis has been described [Ooi and Miller (1991) *J. Gen. Virol.* 72:527–534; Lu and Carstens (1992) *Virology* 190:201–209]. This result had potential relevance to tox34 expression since the formation of duplex RNA at the 5' end of tox34 mRNA can inhibit its translation, thereby decreasing Tox34 levels.

vSp-tox34 infection of neonate *T. ni* larvae (tox34 expressed under the transcriptional control of the hybrid very late promoter, $P_{synSIV}$) resulted in paralysis of larvae about 45k faster than wild-type. Therefore, it was of interest to evaluate the effect of promoters for potentially earlier expression of tox34 in infected cells as a means to further decrease the $ET_{50}$ of tox34-expressing recombinants, four recombinant viruses expressing tox34 under control of the D. melanogaster HSP70 promoter (vHSP70tox34), the early AcMNPV DA26 gene promoter (vDA26tox34), the late AcMNPV 6.9K DNA binding protein gene promoter (vp6.9tox34), and the very late $P_{synXIV}$ promoter (vSp-tox34) were constructed (see FIG. 2A and the Examples). vETL-tox34, in which the *P. tritici* Tox34 toxin coding sequence is expressed under the control of the early ETL promoter [Tomalski and Miller (1992) *Bio/Technology* 10:545–549] was not as desirable as the vp6.9tox34 or the vHSP70tox34 as an insect control agent.

Analyses of time courses of tox34 expression in TN-368 cells infected with these four viruses and wild-type AcMNPV illustrated the relative levels and timing of tox34 expression in these cells. Western blot analysis using antibody against Tox34 detected Tox34 in the supernatants and in cell lysates of virus-infected cells at 0, 6, 12, 24 and 48 h p.i. (FIGS. 4A–4B). No Tox34 was detected in wild-type AcMNPV-infected cells throughout the time course of infection in either the cell lysate or supernatant fractions (FIGS. 4A and 4B, lanes 1 to 5). Surprisingly, Tox34 was not found in the lysates from vHSP70tox34-infected cells, and it was first observed in the supernatant at 24 h p.i., with increased levels found by 48 h p.i. (FIG. 4B, lanes 9 and 10). This lack of accumulation in the cellular fraction suggests that Tox34 is efficiently secreted from the infected cell. The levels of Tox34 in vDA26tox34-infected cells were too low to detect in either intracellular or extracellular fractions (FIGS. 4A and 4B, lanes 11 to 15). vp6.9tox34-infected cells showed the highest expression of Tox34 of all promoters tested, and substantial levels of Tox34 were detected in both fractions at both 24 and 48 h p.i. (FIGS. 4A and 4B, lanes 19 and 20). Expression of Tox34 in vp6.9tox34-infected cells was at least 24 h earlier than tox34 under very late promoter control, where Tox34 was not detected until 48 h p.i. (FIGS. 1A and 4B, compare lanes 19 and 24, and lanes 20 and 25). The two immunoreactive species found in vp6.9tox34- and vSp-tox34-infected cell lysates represent mature Tox34 and its unprocessed, precursor form.

The response of neonate *S. frugiperda* (Table 3) or *T. ni* larvae (Table 4) to infection by virus expression of tox34 under the control of different promoters was studied to determine whether the time to paralysis was affected by the promoter and whether there were species-specific differences. In both species the $LC_{50}$s of all four recombinants were similar to the $LC_{50}$ of wild-type AcMNPV. The higher $LC_{50}$ values for wild-type AcMNPV in *S. frugiperda* (about 200 fold) relative to *T. ni* neonates have been previously documented [Clem et al. (1994) *J. Virol.* 75:1551–1556]. In *T. ni* larvae, vp6.9tox34 performed best, reducing time to paralysis by about 60% compared to wild-type, and vp6.9tox34 outperformed vSp-tox34 by 20%. A similar $ET_{50}$ was found for vp6.9tox34 in *S. frugiperda* larvae, but in this case vHSP70tox34 performed as well, if not better. An additional species-specific difference in $ET_{50}$ was found with vDA26tox34, which was more effective in *S. frugiperda* larvae than *T. ni* larvae by about 10 h. These results indicate that there are differences in the relative strengths of these two "early" promoters in the two insect species.

To determine if a promoter-specific effect was detectable in cell culture, time course studies of tox34 expression in vHSP70tox34- and vDA26tox34-infected SF-21 and TN-368 cells were performed (FIG. 5). Because levels of Tox34 secreted from vHSP70tox34 and vDA26tox34 were low to undetectable (FIGS. 4A and 4B), proteins in the supernatant fraction were precipitated with 20% trichloroacetic acid (TCA) prior to separating the proteins by SDS-PAGE and detecting Tox34 by immunoblot analysis. Comparison of the relative levels of Tox34 secreted by each cell line revealed that the HSP70 promoter was significantly stronger than the DA26 gene promoter in both cell lines (FIG. 5, compare lanes 1–5 with lanes 11–15, and lanes 6–10 with lanes 16–20). A comparison of each promoter in the two cell lines showed that detectable levels of Tox34 from both the DA26 and HSP70 promoters appear at least 24 h earlier in SF-21 than in TN-368 cells. Longer exposures of this blot detected Tox34 as early as 6 and 12 h p.i. in the supernatants of vHSP70-tox34-infected SF-21 and TN-368 cells, respectively. This analysis of the level and timing of tox34 expression with vHSP70tox34 and vDA26tox34 in the two cell lines at the protein level corresponds well with the relative time to paralysis in neonate bioassays (Tables 4 and 5).

S1 nuclease analysis revealed that a transcriptional start site was located on the complementary strand within the native tox34 signal sequence. Transcripts initiating from this site could potentially form duplex RNA with tox34 transcripts in infected cells to interfere with the translation of tox34.

Oligonucleotide site-directed mutagenesis was performed on pSp-tox34 and pSp-p6.9tox34 to change the CTTAA motif to a CTTGA motif (See FIG. 1E) within the tox34 signal coding sequence without altering the amino acid sequence of the signal peptide. The effect of this altered signal peptide coding sequence was tested using recombinant virus expressing the modified tox34 gene (tox34m) under 6.9K (vp6.9tox34m) or $P_{synXIV}$ (vSp-tox34m) promoter control. Cell lysates and supernatants were examined for Tox34 or Tox34m expression from 18 to 48 h p.i. (FIGS. 6A and 6B). In vSp-tox34- and vSp-tox34m-infected cells, Tox34 was detected in both fractions at 48 h p.i. Expression of Tox34 or Tox34m from the 6.9K promoter was observed at 18 h p.i. The relative levels of intracellular Tox34 were approximately 2 to 3 fold higher in cells infected with vp6.9tox34m than with vp6.9tox34, indicating that removal of the reverse TAAG motif increased the intracellular levels of Tox34 protein. This difference was not observed in vSp-tox34 and vSp-tox34m infected cells. Without wishing to be bound by theory, it is believed that the complementary TAAG motif acts as a late rather than a very late promoter during infection, and consequently, RNA initiating from this promoter primarily effects translation from tox34 expressed from the late 6.9K promoter. No differences in the extracellular levels of Tox34 were observed between vp6.9tox34 and vp6.9tox34m infected cells (FIG. 5B). It is possible that the level of Tox34 produced in vp6.9tox34-infected cells has overwhelmed the cell's secretory pathway so that even higher levels of precursor Tox34 produced in vp6.9tox34m infected cells do not affect the level of secreted Tox34.

vp6.9tox34m and vSp-tox34m were also used in per os infection of neonate *S. frugiperda* and *T. ni* larvae to determine whether there were any differences in the $LC_{50}$ and $ET_{50}$ of these recombinant viruses. No differences were observed in the $LC_{50}$s of each virus in either species relative to wild-type AcMNPV (Table 6). The $ET_{50}$ of vp6.9tox34m was moderately longer than vp6.9tox34 by 4.5 and 5.6 h in *S. frugiperda* and *T. ni* larvae, respectively, and was just outside the limits of standard error. vSp-tox34m performed better than vSp-tox34 in both species. Its effect seemed to be greater in *S. frugiperda* larvae, decreasing the time to paralysis by about 7 h.

None of the heterologous signal sequences tested increased the levels of secreted Tox34 in cell culture, and none improved the time to paralysis of *T. ni* infected with these viral recombinants. Promoter choice, however, did significantly influence the timing and level of secreted toxin in cell culture, and surprisingly, certain promoters dramatically improved the properties of the virus as a biopesticide.

The major effect of changing the signal sequence was to affect the intracellular levels of Tox34. The levels of toxin in vSp-tox21A/tox34 infected cells accumulated to a higher level than in vSp-tox34 infected cells at 48 h p.i., suggesting that the tox21A signal sequence was less efficient at directing the secretion of Tox34 than the native tox34 signal sequence. Very low amounts of toxin were detected in vSp-BSigtox34 infected cells even though similar levels of toxin transcripts were found in vSp-BSigtox34 and vSp-tox34 infected cells. The stability of Tox34 may be affected as a result of the change in the signal sequence or the N-terminal residue of the mature polypeptide. This signal sequence has been used successfully to promote the secretion of active prothoracicotropic hormone using the baculovirus expression system [O'Reilly et al. (1995) supra]. The addition of an extra glycine residue to the amino terminus of the mature Tox34 may have destabilized rather than stabilized Tox34.

Modification of the native tox34 signal sequence to remove the complementary TAAG motif did not increase the level of secreted Tox34 in cell culture, but it did significantly increase the levels of intracellular Tox34 and its precursors. This suggested that while removal of the TAAG sequence increased expression of Tox34 in the cell, processing and transport through the secretory pathway was the limiting step in obtaining increased extracellular toxin levels. A decrease in the $ET_{50}$ of vSp-tox34m relative to vSp-tox34 in *S. frugiperda* larvae was observed, suggesting that there was some in vivo effect of altering this reverse TAAG motif. These results suggest that it is advantageous to use this modified signal for those promoters (e.g. HSP70) which are expressed earlier and continue to be expressed late in infection but produce less toxin than the threshold level required for paralysis.

All of the toxin-expressing recombinant viruses (regardless of promoter) reduced the effective time to paralysis/mortality relative to wild-type AcMNPV. The most effective viral promoter in the two species tested was the late 6.9K DNA binding protein gene promoter of AcMNPV. Tox34 under 6.9K promoter control was expressed both earlier (at least 24 h) and at greater levels than tox34 under control of a hybrid promoter composed of both late and very late promoter elements [Tomalski and Miller (1992) supra]. Superior expression mediated by the 6.9K promoter over either the p10 or polyhedrin gene promoters has been previously reported with respect to the expression of juvenile hormone esterase and β-galactosidase [Bonning et al. (1994) *J. Gen Virol.* 75:1551–1556]. The earlier synthesis and secretion of Tox34 in vp6.9tox34 infected SF-21 cells reflects the performance of the recombinant virus in vivo.

Tox34 under control of the early DA26 promoter was the least effective in both species, a result also found with another early promoter (ETL) of AcMNPV [Tomalski and Miller (1992) supra]. The results indicate that although tox34 is expressed earlier in these cells, it is not initially expressed at the threshold level needed to paralyze larvae. The hsp70 promoter has been shown to be a relatively strong promoter when compared to early viral promoters [Morris and Miller (1992) *J. Virol.* 66:7397–7405] and this promoter was found to drive higher levels of tox34 expression than the DA26 promoter in both *T. ni* and *S. frugiperda*. Surprisingly, tox34 expressed under the control of the hsp70 promoter resulted in the shortest $ET_{50}$ in *S. frugiperda* larvae, even through overall levels of Tox34 secreted under the hsp70 promoter were substantially lower than tox34 expressed under 6.9K promoter control. This indicates that tox34 expression from a strong constitutive promoter can, in at least some cases, be more effective than expression from a strong late viral promoter. The differences observed for $ET_{50}$ values for vHSP70tox34 and vDA26tox34 in the two species suggests that the effectiveness of a particular promoter is host-dependent.

As discussed above, there is a longfelt need in the art for biological pesticides which are especially selective for target insect pests. Baculoviruses are being considered to fill this need, but most baculoviruses require from four to fourteen days to kill their insect hosts, and during this time the insects continue to feed and effect significant damage to crops and other vegetation. Genetic modifications of baculovirus genomes have resulted in certain improvements of baculoviruses as insect control agents by reducing the time to mortality in infected insects. The expression of insect predacious mite toxins which are specific for insects by recombinant baculoviruses has led to reduction of feeding time in infected insects; the present invention provides further improvement in such baculoviruses. Changes made to the signal sequence of the insect-specific toxin did not improve the level of secreted mite toxin, and in fact, the specific changes to the signal sequence tested resulted in an increase in the time to paralysis of infected insects. Surprisingly, however, promoter choice was a key factor in improving the time of expression, increasing the levels of toxin protein, and reducing the time to paralysis in a host-dependent manner. Without wishing to be bound by theory, it is proposed that the most effective promoter for driving toxin expression in most insect hosts is either an AcMNPV 6.9K promoter or a heat shock promoter, in particular, the Drosophila hsp70 promoter.

Insecticidal compositions suitable for applications to plants to control insect pests comprise an agriculturally suitable carrier and an insect control agent. Application of an insecticidal composition of this invention can protect plants from insect pests by reducing feeding by and killing of susceptible insects.

The skilled artisan knows how to choose an insect control agent, e.g., an insect virus, which is suitable for the control of a particular insect pest. It will be understood by those skilled in the art that the insect pests can be exposed to the insect control agent of the present invention by conventional methods including ingestion, inhalation or direct contact of the insect control agent.

A primary use of the genetically engineered baculoviruses of the present invention will be as components of agricultural compositions for applying to plants, plant environments or distributed in baits to effect the biological control of insect pests. It will also be possible to use the insect control agents of the present invention in the control of other insect pests with the appropriate choice of the particular organism genetically modified to express an insect-specific paralytic neurotoxin. For example, there are baculoviruses known to specifically infect each of mosquitoes, beetles and fleas, besides the common Lepidopterans. The target insect guides the skilled artisan in the selection of the insect control agent expressing the paralytic toxin, and the particular agent constrains the selection of an appropriate promoter sequence. Many variations of preparing such agriculturally suitable and/or environmentally acceptable compositions for insect control are known in the art.

The concentration of the genetically engineered baculovirus required to produce insecticidally effective compositions for the control of an insect pest depends on the type of organism and neurotoxin used and the formulation of the composition. The insecticidally effective concentration of the insect control agent within the composition can readily be determined experimentally, as understood by the skilled artisan. For example, the insecticidally effective concentration of a virus can be readily determined using bioassay techniques known to the art.

Agricultural compositions for control of insect pests of plants must be suitable for agricultural use and dispersal in fields. Similarly, compositions for the control of other insect pests must be environmentally acceptable. Generally, components of the composition must be non-phytotoxic and not detrimental to the integrity of the occluded virus. Foliar applications must not damage or injure plant leaves. In addition to appropriate solid or, more preferably, liquid carriers, agricultural compositions may include sticking and adhesive agents, emulsifying and wetting agents, but no components which deter insect feeding or any viral functions. It may also be desirable to add components which protect the insect control agent from UV inactivation or components which serve as adjuvants to increase the potency and/or virulence of an entomopathogen. Agricultural compositions for insect pest control may also include agents which stimulate insect feeding.

Reviews describing methods of application of biological insect control agents and methods and compositions agricultural application are available. See, for example, Couch and Ignoffo (1981) in *Microbial Control of Pests and Plant Disease* 1970–1980, Burges (ed.), chapter 34, pp. 621–634; Corke and Rishbeth, ibid, chapter 39, pp. 717–732; Brockwell (1980) in *Methods for Evaluating Nitrogen Fixation*, Bergersen (ed.) pp. 417–488; Burton (1982) in *Biological Nitrogen Fixation Technology for Tropical Agriculture*, Graham and Harris (eds.) pp. 105–114; and Roughley (1982) ibid, pp. 115–127; *The Biology of Baculoviruses*, Vol. II, supra, and references cited in the above. Wettable powder compositions incorporating baculoviruses for use in insect control are described in EP 697,170 (Ahmed, published Feb. 21, 1996) incorporated by reference herein.

Monoclonal or polyclonal antibodies, preferably monoclonal, specifically reacting with a toxin protein encoded by a particular coding sequence identified using the present methods may be made by methods known in the art. See, e.g., Harlow and Lane (1988) *Antibodies: A Laboratory Manual*, Cold Spring Harbor Laboratory Press, Plainview, N.Y. and Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in O'Reilly et al. (1992) *Baculovirus Expression Vectors: A Laboratory Manual*, W. H. Freeman, New York, N.Y.; Sambrook et al. (1989) *Molecular Cloning*, Second Edition, Cold Spring Harbor Laboratory Press, Plainview, N.Y.; Maniatis et al. (1982) *Molecular Cloning*, Cold Spring Harbor Laboratory Press, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. Each reference cited in the present application is incorporated by reference herein in its entirety.

This invention is illustrated by the following examples, which are not to be construed in any way as imposing limitations on the scope thereof. It is understood that resort can be made to various other embodiments, modifications, alternatives and equivalents of the procedures materials and techniques specifically described which, after reading the description herein, may suggest themselves to those skilled in the art without departing from the spirit of the present invention and/or the scope of the appended claims.

THE EXAMPLES

Example 1

Insect Cells and Viruses

All AcMNPV viruses are originally derived from AcMNPV L-1 [Lee and Miller (1978) *J. Virol.* 27:754], and are plaque-purified and propagated in *Spodoptera frugiperda* IPLB-SF-21 cells (Sf cells, *Spodoptera frugiperda* [Vaughn et al. (1977) *In Vitro* 13:213–217] or TN-368 cells (Tn) *Trichoplusia ni* cells [Hink, W. F. (1970) *Nature* 226:466–467] in TC-100 medium (GIBCO, Grand Island, N.Y.) supplemented with 10% fetal bovine serum and 0.26% tryptose broth at 27° C. as described previously [O'Reilly et al. (1992) *Baculovirus Expression Vectors: A Laboratory Manual*, W. H. Freeman, New York, N.Y.]. AcMNPV Viruses were titered using IPLB-SF-21 cells and the standard plaque assay as described by O'Reilly et al. (1992) supra. AcMNPV L1 served as the wild-type virus for comparative purposes.

Recombinant viruses vSptox34 and vHSP70tox34 contain the tox34 coding sequence expressed under the regulatory control of the synthetic hybrid viral promoter $P_{synXIV}$ [Wang et al. (1991) *Gene* 100:131–137] and the *Drosophila melanogaster* hsp70, respectively [Tomalski and Miller (1992) *Bio/Technology* 10545–549; McNitt et al. (1995) *Bio. Control* 5:267–278]. vHSP70tox34 was constructed starting with pEVptox34 digested with EcoRI and BglII to release a tox34 fragment (see U.S. Pat. No. 5,266,317) and plasmid pHSP70PLV1+CAT [Morris and Miller (1992) *J. Virol.* 66:7397–7405] which was digested with EcoRI and BglII to produce a vector fragment and a cat fragment, which is discarded. The vector fragment contains the *D. melanogaster* hsp70 promoter with sequence from about −500 to +231 [see Toeroek and Karch (1980) *Nucl. Acids Res.* 8:3105–3123]. Insertion of the Tox34 coding sequence in the proper orientation was confirmed by restriction endonuclease analysis (digests with XbaI, NdeI, and a double digest with EcoRI and BglII). The resulting transfer plasmid was cotransfected into SF21 cells with DNA of the virus vSynVl-gal, an AcMNPV derivative containing lacZI in place of pohl. Recombinant viruses were identified by their white, occulusion-positive phenotype on Xgal plates, and their genotype was confirmed by restriction endonuclease analysis. Recombinant virus vSp-tox21A expresses the tox21A coding sequence, a homolog of the tox34 coding sequence also isolated by cDNA cloning from *Pyemotes tritici* insect-predacious mites, under the regulatory control of the $P_{synXIV}$.

Hz 105/UND-K cells (HzUNDK), clonally isolated from IPLB-Hz 107S [Corsaro et al., (1989) *J. Virol Methods* 5:283–292], were provided by Dr. Malcolm Fraser (University of Notre Dame, Notre Dame, Ind.) and were maintained at 27° C. in TCIOO medium supplemented with 10% fetal bovine serum and 0.26% tryptose broth, as previously described [O'Reilly et al. (1992) *Baculovirus Expression Vectors: A. Laboratory Manual*, W. H. Freeman, new York, N.Y.]. A plaque-purified isolate of the Elcar™ strain of HzSNPV, provided by Dr. William Rice (USDA-ARS Rice Research Center, Crawley, La.), served as the parental wild type (wt) virus and was propagated in HzUNDK cells. HzSNPV viruses are readily available in the art.

Example 2

EGT Assays

HzUNDK cells ($2\times10^6$ per 60 mm dish) were infected with wt HzSNPV or AcMNPV at a multiplicity of infection of 10. After 48 h post-infection the infected cell culture supernatant was collected and transferase activity was assayed using 100 µl of supernatant with [$^3$H] ecdysone (Dupont, NEN Research Products) and UDP-galactose or UDP-glucose serving as the substrate [O'Reilly et al. (1992) *Insect Biochem. Molec. Biol.* 22:313–320]. Ecdysone was separated from ecdysone-sugar conjugates by thin layer chromatography on silica gel plates, and the radiolabel was detected by autoradiography.

Example 3

Identification and Sequencing of the HzSNPV egt Gene

A cosmid library of the HzSNPV genome was constructed using SuperCos (Stratagene, LaJolla, Calif.) as the vector. Selected cosmid and plasmid clones containing HzSNPV genomic fragments were screened by polymerase chain reaction (PCR) using two degenerate primers designed from two highly conserved regions of known UDP-glucosyltransferases. The sequence (where I is inosine, Y is C or T, S is G or C, K is G or T, M is A or C, W is A or T, H is A or C or T, B is G or T or C, V is G or C or A, and N is all four nucleotides) of the primers included a 5' terminal BAMHI or EcoRI site respectively: 5' GC GGA TCC AIY GTG SWG TWY NTK GGM GG 3' (SEQ ID NO: 16) [corresponding to SVQYLGG (SEQ ID NO: 17) in the AcMNPV EGT sequence] and 5' GC GAA TTC GGM ABV MHC ACC AKN GG 3' (SEQ ID NO: 18) [originally intended to correspond to PMVCLP (SEQ ID NO: 19) in many EGT sequences].

PCR amplification using an HzSNPV cosmid, which spanned the HindIII J through E fragments, and a plasmid clone containing the HindIII-C fragment as templates generated a PCR product of the size expected for the egt gene. The sequence of the PCR product confirmed that it was derived from the HzSNPV egt gene. The entire gene was then sequenced in both directions with the aid of synthetic oligonucleotide primers which provided sufficient overlap between contiguous sequences for confident alignments and unambiguous sequence information.

Nucleotide sequences of known egts available in GenBank were aligned using the Pileup and Boxshade programs. (See FIGS. 11B–11C) Amino acid sequences were compared using the Bestfit analysis (Genetics Computer Group, University of Wisconsin, Madison, Wis.). Phylogenetic relationships based on the sequence comparison are shown diagrammatically in FIG. 11A.

Example 4

Construction of HzSNPV Transfer Vectors and Recombinant HzSNPV Viruses

The egt gene was found to be located entirely within the EcoRI Q fragment. This fragment was cloned from HzSNPV into the EcoRI site of Bluescript II KS+ (Stratagene) and a 600 bp SalI/EcoRI fragment downstream of egt was removed to produce pHzEGT (FIG. 7). pHzEGT was digested with SalI which removed an internal segment of egt and the ends filled in by Klenow. The vector fragment was then ligated to a blunt-ended fragment containing the *E. coli* β-glucuronidase gene (GUS), under the control of the *D. melanogaster* hsp70 promoter, and Bsu36I and Sse8387I sites on either side of GUS to form pEGThspGUS. Additionally it was ligated to a DA26 promoted-, p6.9 promoted-, or a *D. melanogaster* HSP70 promoted-tox34 gene. The DA26 and p6.9 promoters were derived from AcMNPV [Lu et al. (1995) *Biol Control.* 7:320–332]. A plasmid with a deletion in egt was made from SalI-digested pHzEGT by ligation of the vector fragment. The resulting plasmid, pEGTdel, was used to generate a plasmid, pEGTlinker, with unique Bsu36I and Sse8387I sites within egt by digesting the plasmid DNA with SalI and ligating it to an oligonucleotide with SalI cohesive ends and unique Bsu361 and Sse8387I sites (FIG. 7). The oligonucleotide was constructed by annealing the following primers together (5' T CGA CCT CAG GGC AGC TTA AGG CCT GCA GG 3' (SEQ ID NO: 20) and 5' TCG ACC TGC AGG CCT TAA GCT GCC CTG AGG 3') (SEQ ID NO: 21).

HzSNPV was found to have a unique Bsu36I site which was located within the HindIII-C fragment. A 2.1 kb ClaI fragment containing the Bsu36I site was cloned from HindIII-C and the region surrounding the site was sequenced. The site was eliminated from the virus by digesting viral DNA with Bsu36I, filling in with Klenow polymerase and religating the DNA. The DNA was then digested with Bsu36I again and transfected into HzUNDK cells. Viruses emerging from these transfections were plaque-purified, amplified and tested for the loss of the Bsu36I site. Selected viruses lacking the Bsu36I site were then tested for their infectivity ($LC_{50}$) and virulence ($LT_{50}$) in *H.zea* neonates.

The Bsu36I⁻ virus, HzSNPV(Bsu36I⁻), was allelically recombined with pEGThspGUS to create an EGT deleted virus that yielded blue plaques in HzUNDK cells in the presence of X-gluc (5-bromo-4-chloro-3-indolyl β-D-glucuronide). Using this virus, HzSNPV(Bsu36I⁻)-EGThspGUS or more simply HzEGThspGUS, the following recombinant viruses were generated by allelic replacement [O'Reilly et al. (1992) *Baculovirus Expression Vectors: A Laboratory Manual*, W. H. Freeman, New York, N.Y.] using transfer plasmids HzEGTdel, HzEGTDA26tox34, HzEGTp6.9tox34, and HzEGTHSPtox34 (FIG. 7). To enhance recombination, viral DNA was linearized with Bsu36I before transfection of viral and plasmid DNA. Virus recombinants were screened for a white, occlusion positive, plaque phenotype. Viruses were further plaque purified and then amplified. Viral DNA was analyzed by restriction endonuclease analysis to confirm allelic replacement.

Example 5

Insect Bioassays with HzSNPV and its Derivatives

The $LC_{50}$ and $ET_{50}$ (mean time to effectively paralyze 50% of test larvae) of viruses were determined using neonate *H. zea.* Bioassays were conducted as droplet feeding assays according to the protocols developed by Hughes et al. (1986) *J. Invertebr. Pathol.* 48:189–192. Neonates were fed known concentrations of viral occlusion bodies (PIBs) suspended in 5% sucrose and 1 mg/ml FD&C blue #1 dye (Hilton Davis, Cincinnati, Ohio) by placing them in the center of a 60 mm plastic petri dish and providing them with 0.5 µl droplets of the PIB suspension pipetted on the bottom near the edge of the dish. Larvae that had ingested the PIBs within 30 mins, as determined by their blue color, were transferred to fresh diet (described as *S. frugiperda* diet in O'Reilly et al. (1992) *Baculovirus Expression Vectors: A Laboratory Manual*, W. H. Freeman, New York, N.Y.] and monitored approximately every six hours. Five virus concentrations with 30 insects per dose were tested for each virus. $ET_{50}s$ were determined by the Vistat 2.1 program [Hughes, P. R. (1990) *ViStat: Statistical package for the analysis of baculovirus bioassay data*, Boyce Thompson Institute, Cornell University, Ithaca, N.Y.] and $LC_{50}s$ were determined using Polo-PC [Robertson and Prieler (1992) Polo-PC. In *"Pesticide Bioassays with Arthropods."* CRC Press, Boca Raton, Fla.].

Example 6

Construction of recombinant viruses with alternate signal sequences

All recombinant viruses were constructed by allelic replacement using previously described methods [O'Reilly et al. (1992) supra]. Transfer plasmids were cotransfected into SF-21 cells with vSynVI⁻gal [Wang et al. (1991) supra] and recombinant viruses were selected based on a white occlusion-positive plaque phenotype. Each recombinant virus was verified using appropriate restriction endonuclease digestion analysis. All recombinant viruses contain tox34 inserted upstream of and in the opposite direction to the polyhedrin gene.

The virus, vSp-BSigtox34, containing tox34 fused in frame to the sarcotoxin IA gene signal sequence from the flesh fly *Sarcophaga peregrina* [O'Reilly et al. (1995) supra] was constructed as follows: Two oligonucleotide primers, tox34up and tox34down, corresponding to nucleotides 118 to 138 and complementary to nucleotides 862 to 876, respectively, of tox34 (SEQ ID NO:3) [Tomalski and Miller (1991) *Nature* 352:82–85] were used in a polymerase chain reaction (PCR) to amplify a 777 base pair fragment containing tox34 without its native signal sequence. The primer tox34up was designed to add an extra glycine residue to the N-terminus of the mature tox34 gene product (see FIGS. 1A and 1B): N-terminal glycine residues reportedly stabilize recombinant gene products [Bachmair et al. (1986) *Science* 34:179–186]. The PCR-amplified product was digested with HindIII and SmaI (recognition sites incorporated into the primers) and inserted in frame into plasmid pBSig [O'Reilly et al. (1995) supra] between the EcoRI site, blunt-ended with Mung Bean nuclease, and the HindIII site. The resulting construct, pBSigtox34, contains tox34 fused with the sarcotoxin IA signal sequence. The junction between the signal sequence and tox34 was confirmed by sequence analysis (FIG. 2B). In addition, the entire tox34 PCR product was sequenced to ensure that no mutations were introduced during PCR. The transfer vector, pSp-BSigtox34, was constructed by digesting pBSigtox34 with BamHI, filling in the ends with the large fragment of DNA polymerase I (Klenow) followed by digestion with BglII. A fragment containing BSigtox34 was gel-purified and inserted into pSp-tox34 between a blunt-ended EcoRI site and the BglII site placing BSigtox34 under control of the $P_{synXIV}$ promoter (FIG. 2A, vSp-BSigtox34).

Recombinant virus vSp-DCtox34 (FIG. 2A), containing tox34 fused with the Drosophila cuticle gene signal sequence (FIG. 1C) [Snyder et al. (1982) *Cell* 29:1027–1040] was constructed by digesting the plasmid pBSIGtox34SmaI with BamHI and SmaI and inserting a 24 base pair oligonucleotide containing Esp3I and BspMI sites. The plasmid pBSigtox34SmaI is a derivative of pBSigtox34 containing a SmaI site at the junction between the sarcotoxin IA signal sequence and tox34. The resulting plasmid, pEBtox34, contains two unique restriction sites (Esp3I and BspMI) upstream of the mature tox34 sequence in place of the sarcotoxin IA signal sequence. The oligonucleotide was designed so that digestion with Esp3I and BspMI and subsequent filling in of the ends with Klenow polymerase generates blunt ends into which any signal sequence can be inserted in-frame with tox34 in an optimal baculovirus late/very late AUG context [O'Reilly et al. (1992) supra]. Two complementary oligonucleotides containing the Drosophila cuticle signal sequence with an Esp3I site were annealed, digested with Esp3I, blunt-ended with Klenow, and inserted into the Esp3I and BspMI sites of pEBtox34 after the ends were filled in with Klenow. The resulting construct, pEBDCtox34, contains tox34 fused in-frame with the Drosophila cuticle signal sequence (FIG. 1C). The correct junction between the cuticle signal sequence and tox34 was verified by sequence analysis. The Drosophila cuticle signal sequence-tox34 gene fusion (DCtox34) was transferred into pSp-tox34 by digesting pEBDCtox34 with BamHI, filling in the ends with Klenow and digesting with BglII. The fragment containing DCtox34 was then cloned into pSp-tox34 digested with EcoRI, blunt ended, and digested with BglII, thus placing DCtox34 under control of the $P_{synXIV}$ promoter (FIG. 2A, vSp-DCtox34).

Recombinant virus vSp-tox21A/tox34 (FIG. 2A) containing a hybrid toxin gene composed of the mature tox34 gene fused with the tox21A signal sequence [Tomalski et al. (1993) supra] was constructed using the technique of gene splicing by overlap extension [Horton et al. (1989) *Gene* 77:61–68]. First, the tox21A signal sequence was amplified with primers "a" (SEQ ID NO:5) and "b" (SEQ ID NO:6) (FIG. 1D) using pBS-tox21A [Tomalski et al. (1993) supra] as a template. These primers correspond to the first 24 nucleotides of the tox21A signal sequence and are complementary to nucleotides 94 to 120 of tox34, respectively. The mature tox34 gene was PCR amplified using two primers, one complementary to primer "b" (FIG. 1A, primer "c", SEQ ID NO:7), and the second one complementary to nucleotides 862 to 876 [Tomalski and Miller (1991) supra] at the 3' end of tox34 that was previously used to amplify tox34 in vSp-BSigtox34 (tox34down, see above). The PCR products from these two independent amplifications were combined and further amplified using primer "a" and tox34down, which resulted in a single fragment containing tox34 with the tox21A signal sequence (tox21A/tox34). Tox21A/tox34 was digested with EcoRI and BglII (recognition sites incorporated into primers "a" and tox34up) and cloned into the corresponding sites in pSp-tox34 (see FIG. 2A).

Example 7

Construction of recombinant AcMNPV viruses with tox34 under control of different cellular and viral promoters vp6.9tox34 and vDA26tox34 (FIG. 2B) were generated using allelic replacement as described previously [O'Reilly et al. (1992) supra] using the transfer plasmids described below. p6.9tox34 was constructed by cloning a 933 bp EcoRI fragment containing tox34 from pSp-tox34 into p6.9hc between a BglII site and a KpnI site blunt-ended with T4 DNA polymerase. p6.9hc is a reporter plasmid containing the chloramphenicol acetyltransferase gene (cat) under control of the late 6.9K core DNA binding protein gene promoter of AcMNPV [Todd et al. (1996) *J. Virol.* 70:2307–2317]. The transfer vector, pSp-p6.9tox34, was constructed by cloning a 1.1 kb EcoRI/EcoRV fragment from p6.9tox34 containing tox34 under 6.9K promoter [Wilson et al. (1987) *J. Virol.* 61:661–666] control into pSp-tox34 digested with EcoRI and EcoRV (see FIG. 2B).

vDA26tox34 was constructed using two oligonucleotide primers corresponding to nucleotides −283 to −264 and complementary to −22 to −1 of the AUG of the early DA26 gene mRNA of AcMNPV [O'Reilly et al. (1990) *J. Gen. Virol.* 71:1029–1037]. The 290 bp PCR product was digested with EcoRV and BglII (recognition sites incorporated into the primers) and cloned between the EcoRV and BglII sites of PCAPCAT [Thiem and Miller (1990) supra] reported plasmid containing cat under control of the late capsid protein gene promoter of AcMNPV [Thiem and Miller (1989) *J. Virol.* 63:4489–4497]. The resulting construct, pDA26CAT, contains the DA26 gene promoter in place of capsid protein gene promoter. A 933 bp fragment containing tox34 was removed from pSp-tox34 by digestion with EcoRI, blunt-ended with Klenow, and cloned into pDA26CAT digested with BglII and KpnI and treated with T4 DNA polymerase. This construct was digested with EcoRI and EcoRV, and a 1.2 kb fragment containing tox34 under DA26 promoter control was inserted into the corresponding sites of pSp-p6.9tox34 resulting in the transfer vector pSp-DA26tox34 (see FIG. 2B)

Example 8

Construction of recombinant viruses without a reverse TAAG sequence in the native tox34 signal sequence Viruses vp6.9tox34m and vSp-tox34m (FIG. 2C), with a mutated reverse TAAG sequence in the native tox34 signal sequence (FIG. 1E), were generated by site-directed mutagenesis of transfer plasmids pSp-p6.9tox34 and pSp-tox34 using the Transformer Kit (Clontech, Palo Alto, Calif.) according to the manufacturer's protocol. Two primers, a selection primer 5'-GGG TCG ACA CAG CTG CAG CTC-3' (SEQ ID NO:8) which eliminates a BglII site in both parent plasmids, and a mutagenic primer 5'-GCC ATT ATC AAT CAA GGA AAT AT-3' (base change is underlined; SEQ ID NO:9), complementary to nucleotides 104 to 126 of tox34 [Tomalski and Miller (1991) supra], which eliminates the reverse TAAG sequence were used with the kit. Transfer plasmids, pSp-p6.9tox34m and pSp-tox34m, were sequenced to verify that the base change was present in the tox34 signal sequence.

Example 9

Time course of tox34 expression in insect cells

SF-21 or TN-368 cells ($1.0 \times 10^6$ cells per 35 mm plate) were infected with virus at a multiplicity of infection of 10 plaque forming units (pfu) per cell. At various times post-infection (p.i.) the tissue culture media were collected, and the cells were lysed in 2× electrophoresis sample buffer [O'Reilly et al. (1992) supra]. Proteins from cell lysates and extracellular fluids were analyzed by SDS-PAGE on 10% polyacrylamide gels, transblotted onto Millipore Immobilon polyvinylidene difluoride (PVDF) membranes (Millipore, Bedford, Mass.), and probed with a polyclonal antibody specific for Tox34 [McNitt et al. (1995) supra; Tomalski et al. (1989) supra]. Tox34 was visualized using the ECL Western blotting detection kit (Amersham Corp., Arlington Heights, Ill.) and quantitated using a Molecular Dynamics densitometer 300A (Sunnyvale, Calif.).

Example 10

RNA isolation and S1 nuclease analysis

Total RNA was isolated from vSp-BSigtox34 and vSp-tox34 infected SF-21 cells at various times p.i. by the guanidinium isothiocyanate method [Chirgwin et al. (1979) *Biochemistry* 24:5294–5299]. S1 nuclease analysis of tox34 transcripts in vSp-BSigtox34 or vSp-tox34 infected cells was performed using 25 μg of total RNA and either a 648 bp or a 668 bp NdeI-HindIII fragment uniquely end-labeled at the NdeI site. DNA-RNA hybridization was performed with 80% formamide-40 mM piperazine-N,N'-bis(2-ethanesulfonic acid) (PIPES)-0.4 M NaCl-1 mM EDTA at 30° C. overnight. S1 nuclease reactions were carried out as described in Sambrook et al. (1989) supra.

Example 11

Larval bioassays for AcMNPV and Recombinants

Polyhedral inclusion bodies (PIBs) were prepared by infecting fifth instar *Spodoptera frugiperda* larvae with $2.0 \times 10^5$ pfu of budded AcMNPV from each of the recombinant viruses. PIBs were isolated as previously described [Eldridge et al. (1992) *Biol. Control* 2:104–110]. The $LC_{50}$ (concentration of occluded viruses required to kill 50% of the test larvae) and the $ET_{50}$ (mean time to effectively paralyze or kill 50% of the test larvae) of toxin-expressing viruses and wild-type AcMNPV were determined using neonate *Trichoplusia ni* or *S. frugiperda* as previously described [Tomalski and Miller (1992) supra]. Six virus concentrations with 60 insects per dose were used to test each virus. $LC_{50}$ and $ET_{50}$ data were analyzed by Probit analysis [Daum, R. J. (1970) *Nature* 226:466–467] and ViStat 2.1 analysis [Hughes (1990) *ViStat: Statistical package for the analysis of baculovirus bioassay data*, Boyce Thompson Institute, Cornell University, Ithaca, N.Y.], respectively. All bioassays were performed at least twice and the results presented represent an average of the results.

Example 12

Recombinant AcMNPV Virus Construction pEV-Tox34 was constructed by inserting the EcoRI fragment containing the Tox34 coding sequence into EcoRI-cut pEVmodXIV, which supplied the powerful LSXIV promoter and sequences flanking the polyhedrin gene of AcMNPV. DNA of wild-type AcMNPV and pEV-Tox34 were cotransfected into insect cells as described in Miller et al. (1986) supra, and a recombinant virus was isolated and designated vEV-Tox34 after selection on the basis of its occlusion-negative phenotype and screening for the proper allelic replacement events by restriction endonuclease analysis and Southern hybridization.

Expression of the Tox34 gene in vEV-Tox34-infected insect cells was tested as follows. Sf21 cells were separately infected with AcMNPV and vEV-Tox34 as described in Lee et al. (1978) supra; Miller et al. (1986) supra, and the cell culture fluids from control (uninfected), AcMNPV and vEV-Tox34-infected cells were collected after 48 hrs of infection. Larvae of the wax moth *Galleria mellonella* were each injected with 5 microliter aliquots of culture fluids. Insect larvae injected with the culture fluid from vEV-Tox34-infected cells were paralyzed within 2 minutes whereas the insect larvae injected with fluid from wild-type AcMNPV-infected cells showed no paralytic response over an extended time period (several days). Paralyzed larvae were visually immobile, they lacked the righting response (the ability to turn themselves upright after turned onto their dorsal sides) and they failed to spin silk to line their burrows (a stereotypic behavior of wax moth larvae). Control larvae exhibited movement, the righting response and silk-spinning behavior. These results indicated that a neuroparalytic toxin was produced in the VEV-Tox34-infected cells, but not in cells infected with wild-type AcMNPV, via expression of the Tox34 cDNA coding sequence and that this toxin was secreted into the extracellular medium. The Tox34 gene product effects contractile muscle paralysis in the challenged insect larvae.

To test the ability of a baculovirus carrying the Tox34 gene to control insect larval feeding behavior during infection, insects were infected with vEV-Tox34 by injecting purified budded virus into the hemolymph of test larvae. *T. ni* larvae in about early fourth instar were injected with TC-100 medium (mock-infected) or medium containing budded virus particles from cell cultures infected with either wild-type AcMNPV or vEV-Tox34 ($4 \times 10^5$ plaque-forming units of virus per larva). Control larvae included those larvae injected with culture medium or with wild-type AcMNPV. Insects injected with VEV-Tox34 were paralyzed (immobilized and lacked righting response) by 36 hr after injection.

In the above-described virus construction, the Tox34 coding sequence is expressed under the regulatory control of the very late LSXIV baculovirus promoter [see also U.S. Pat. No. 5,244,805 (Miller) issued Sep. 19, 1993] which is not expressed until about 18 hrs pi in cells infected at a high multiplicity of infection (moi; i.e. 10 viruses/cell) or until 24–30 hrs pi in cells infected at a moi of 1. Thus, it was not unexpected that the paralytic effects of baculovirus-mediated Tox34 expression were not observed until about 36 hrs pi.

Transplacement plasmid phc-ETL-Tox34 was constructed with the Tox34 coding sequence expressed under the regulatory control of the ETL promoter of AcMNPV [described in Crawford et al. (1988) *J. Virol.* 62:2773–2778, incorporated by reference herein] The Tox34-containing EcoRI fragment was inserted into the EcoRI site of phc-dET, which was derived from phcwt [Rankin et al. (1988) supra] by replacing the polyhedrin promoter between the EcoRV site and the BglII site with the ETL promoter sequences extending from −6 (relative to the ETL translational initiation ATG at +1, +2, +3) to approximately 300 bp upstream of the ETL coding sequences. The transplacement plasmid and wild-type AcMNPV were cotransfected and appropriate nonoccluded recombinants were isolated and characterized.

TABLE 1

Toxicity and a Partial List of Host Preferences for Species of Mites in the Genus Pyemotes
TOXICITY

| | INSECTS | HUMANS | HOSTS |
|---|---|---|---|
| *ventricosus* group | | | |
| anobii | extreme | (?) | Curculionidae |
| | | | Scolytidae |
| | | | Buprestidae |
| | | | Anobiidae |
| beckeri | extreme | (?) | Lyctidae |
| | | | Scolytidae |
| emarginatus | mild | mild | Cecidomyiidae |
| schwerdtfegeri | extreme | mild | Anobiidae |
| | | | Buprestidae |
| tritici | extreme | extreme | Cucujidae |
| | | | Curculionidae |
| | | | Kalotermitidae |
| | | | Vespidae |
| tuberculatus | (?) | (?) | Anobiidae |
| ventricosus | extreme | extreme | Apoidea |
| | | | Chalcidoidea |
| zwoelferi | extreme | extreme | Cecidomyiidae |
| *scolyti* group | | | |
| dimorphus | mild | none | Scolytidae |
| dryas | mild | none | Scolytidae |
| giganticus | mild | none | Scolytidae |
| parviscolyti | mild | none | Scolytidae |
| scolyti | mild | none | Scolytidae |

Modified from Cross and Moser (1975) Ann. Entomol. Soc. Am. 68: 723–732

TABLE 2

Response of neonate *Trichoplusia ni* to infection by wt AcMNPV or recombinant baculoviruses expressing toxins with alternate signal sequences.

Dose response[1]

| | | 95% fiducial limits | | |
|---|---|---|---|---|
| virus | $LC_{50}$ (PIBs/ml) | upper | lower | slope |
| wt AcMNPV | $2.2 \times 10^4$ | $2.6 \times 10^4$ | $1.8 \times 10^4$ | 2.25 |
| 1vSp-tox34 | $2.0 \times 10^4$ | $2.3 \times 10^4$ | $1.6 \times 10^4$ | 2.13 |
| vSp-tox21A | $3.5 \times 10^4$ | $4.1 \times 10^4$ | $3.0 \times 10^4$ | 2.58 |
| vSp-BSigtox34 | $1.6 \times 10^4$ | $2.8 \times 10^4$ | $0.8 \times 10^4$ | 2.08 |
| vSp-tox21A/tox34 | $5.3 \times 10^4$ | $6.5 \times 10^4$ | $4.3 \times 10^4$ | 1.95 |
| vSp-DCtox34 | $2.6 \times 10^4$ | $3.1 \times 10^4$ | $2.2 \times 10^4$ | 2.34 |

Time response[2]

| virus | $ET_{50}$ ± s.e. (h) | slope |
|---|---|---|
| wt AcMNPV | 94.6 ± 1.6 | 14.8 |
| vSp-tox34 | 51.1 ± 0.9 | 13.2 |
| vSp-tox21A | 62.1 ± 0.9 | 18.8 |
| vSp-BSigtox34 | 70.0 ± 2.6 | 6.4 |
| vSp-tox21A/tox34 | 60.8 ± 2.0 | 8.1 |
| vSp-DCtox34 | 49.9 ± 1.0 | 12.5 |

[1] determined by probit analysis
[2] determined by ViStat 2.1 analysis at $LC_{95}$ dose

TABLE 3

Response of neonate Spodoptera frugiperda larvae to oral infection by wt AcMNPV and recombinants expressing tox34 under control of alternate promoters.

Dose response[1]

| virus | $LC_{50}$ (PIBs/ml) | 95% fiducial limits upper | lower | slope |
|---|---|---|---|---|
| wt AcMNPV | $1.3 \times 10^6$ | $1.7 \times 10^6$ | $1.0 \times 10^6$ | 1.43 |
| vHSP70tox34 | $1.6 \times 10^6$ | $1.8 \times 10^6$ | $1.0 \times 10^6$ | 1.49 |
| vDA26tox34 | $1.1 \times 10^6$ | $1.4 \times 10^6$ | $0.8 \times 10^6$ | 1.42 |
| vp6.9tox34 | $0.6 \times 10^6$ | $0.9 \times 10^6$ | $0.3 \times 10^6$ | 1.23 |
| vSp-tox34 | $0.8 \times 10^6$ | $1.0 \times 10^6$ | $0.5 \times 10^6$ | 1.31 |

Time response[2]

| virus | $ET_{50}$ ± s.e. (h) | slope |
|---|---|---|
| wt AcMNPV | 101.3 ± 2.5 | 9.9 |
| vHSP70tox34 | 41.8 ± 2.5 | 8.2 |
| vDA26tox34 | 61.8 ± 2.0 | 7.2 |
| vp6.9tox34 | 44.7 ± 1.7 | 7.4 |
| vSp-tox34 | 55.4 ± 2.0 | 7.0 |

[1]determined by probit analysis
[2]determined by ViStat 2.1 analysis at $LC_{95}$ dose

TABLE 4

Response of neonate Trichoplusia ni larvae to oral infection by wt AcMNPV and recombinants expressing tox34 under control of alternate promoters Dose response[1]

| virus | $LC_{50}$ (PIBs/ml) | 95% fiducial limits upper | lower | slope |
|---|---|---|---|---|
| wt AcMNPV | $5.4 \times 10^3$ | $7.2 \times 10^3$ | $3.5 \times 10^3$ | 1.80 |
| vHSP70tox34 | $4.5 \times 10^3$ | $9.5 \times 10^3$ | $1.0 \times 10^3$ | 1.90 |
| vDA26tox34 | $7.0 \times 10^3$ | $8.9 \times 10^3$ | $5.3 \times 10^3$ | 2.10 |
| vp6.9tox34 | $2.0 \times 10^3$ | $3.5 \times 10^3$ | $0.6 \times 10^3$ | 1.58 |
| vSp-tox34 | $1.6 \times 10^3$ | $2.8 \times 10^3$ | $0.5 \times 10^3$ | 1.58 |

Time response[2]

| virus | $ET_{50}$ ± s.e. (h) | slope |
|---|---|---|
| wt AcMNPV | 99.0 ± 2.0 | 13.9 |
| vHSP70tox34 | 53.8 ± 1.0 | 14.3 |
| vDA26tox34 | 71.2 ± 1.1 | 15.9 |
| vp6.9tox34 | 41.7 ± 1.4 | 12.3 |
| vSp-tox34 | 58.5 ± 1.4 | 12.7 |

[1]determined by probit analysis
[2]determined by ViStat analysis at $LC_{95}$ dose

TABLE 5

Response of neonate S. frugiperda larvae to oral infection by wt AcMNPV or recombinant virus expressing tox34 with or without a reverse TAAG sequence in the tox34 signal sequence.

Dose response[1]

| virus | $LC_{50}$ (PIBs/ml) | 95% fiducial limits upper | lower | slope |
|---|---|---|---|---|
| wt AcMNPV | $3.6 \times 10^5$ | $4.7 \times 10^5$ | $2.5 \times 10^5$ | 1.45 |
| vp6.9tox34 | $1.5 \times 10^5$ | $2.2 \times 10^5$ | $0.9 \times 10^5$ | 1.30 |
| vp6.9tox34m | $3.6 \times 10^5$ | $4.7 \times 10^5$ | $2.6 \times 10^5$ | 1.53 |
| vSp-tox34 | $2.8 \times 10^5$ | $7.1 \times 10^5$ | $1.5 \times 10^5$ | 1.34 |
| vSp-tox34m | $2.5 \times 10^5$ | $3.4 \times 10^5$ | $1.7 \times 10^5$ | 1.45 |

Time response[2]

| virus | $ET_{50}$ ± s.e. (h) | slope |
|---|---|---|
| wt AcMNPV | 103.0 ± 2.1 | 11.5 |
| vp6.9tox34 | 43.9 ± 1.6 | 8.9 |
| vp6.9tox34m | 48.4 ± 1.8 | 6.9 |
| vSp-tox34 | 54.9 ± 1.5 | 8.5 |
| vSp-tox34m | 47.9 ± 1.1 | 11.3 |

[1]determined by probit analysis
[2]determined by ViStat 2.1 analysis at $LC_{95}$ dose

TABLE 6

Response of neonate T. ni larvae to oral infection by wt AcMNPV or recombinant virus expressing tox34 with or without a reverse TAAG sequence in the tox34 signal sequence.

Dose response[1]

| virus | $LC_{50}$ (PIBs/ml) | 95% fiducial limits upper | lower | slope |
|---|---|---|---|---|
| wt AcMNPV | $9.2 \times 10^3$ | $4.6 \times 10^4$ | $1.4 \times 10^4$ | 1.37 |
| vp6.9tox34 | $3.6 \times 10^3$ | $6.0 \times 10^3$ | $1.1 \times 10^3$ | 1.64 |
| vp6.9tox34m | $1.1 \times 10^3$ | $1.5 \times 10^4$ | $7.7 \times 10^3$ | 1.40 |
| vSp-tox34 | $6.5 \times 10^3$ | $9.0 \times 10^3$ | $4.1 \times 10^3$ | 2.01 |
| vSp-tox34m | $6.3 \times 10^3$ | $8.1 \times 10^3$ | $4.4 \times 10^3$ | 2.46 |

Time response[2]

| virus | $ET_{50}$ ± s.e. (h) | slope |
|---|---|---|
| wt AcMNPV | 100.5 ± 2.3 | 11.5 |
| vp6.9tox34 | 41.5 ± 1.6 | 8.2 |
| vp6.9tox34m | 46.7 ± 1.5 | 8.8 |
| vSp-tox34 | 59.2 ± 1.5 | 12.7 |
| vSp-tox34m | 55.9 ± 1.2 | 14.8 |

[1]determined by probit analysis
[2]determined by ViStat 2.1 analysis at $LC_{95}$ dose

TABLE 7

Length, percent similarity and identity of know EGT amino acid sequences to HzSNPV EGT

| Virus | Length | Similarity | Identity |
|---|---|---|---|
| MbNPV | 528 | 70.0 | 49.8 |
| LdNPV | 488 | 65.9 | 49.6 |
| SlNPV | 515 | 70.8 | 49.1 |
| AcNPV | 506 | 67.6 | 46.2 |
| BmNPV | 507 | 67.6 | 46.2 |
| CfNPV | 491 | 61.4 | 42.4 |
| CfDEF | 493 | 63.9 | 45.2 |
| OpNPV* | 293 | 62.2 | 44.1 |
| LoGV | 460 | 65.1 | 43.4 |

*Partial sequence of 293 amino acids

TABLE 8

Dose-mortality response of neonate *Heliocoverpa zea* larvae infected per os with wild-type HzSNPV and various recombinants. Bioassay #1.

| Virus | LC50 (PIB/ml) | 95% Fiducial Limit lower | 95% Fiducial Limit upper | Slope | Hetero-geneity |
|---|---|---|---|---|---|
| HzSNPV Elkar | $1.1 \times 10^3$ | $0.6 \times 10^2$ | $2.7 \times 10^3$ | $1.2 \pm 0.3$ | 0.6 |
| HzSNPV (BSU361-) | $1.7 \times 10^3$ | $1.1 \times 10^3$ | $2.5 \times 10^3$ | $2.1 \pm 0.4$ | 1.0 |
| HzEGTdel | $2.2 \times 10^3$ | $0.6 \times 10^3$ | $4.4 \times 10^3$ | $1.6 \pm 0.3$ | 1.0 |
| HzEGTp6 · 9tox34 | $0.8 \times 10^3$ | $0.2 \times 10^3$ | $1.6 \times 10^3$ | $1.1 \pm 0.2$ | 0.6 |
| HzEGThsptox-34 | $1.2 \times 10^3$ | $0.4 \times 10^3$ | $2.1 \times 10^3$ | $1.2 \pm 0.2$ | 0.9 |
| HzEGTDA26 tox34 | $0.7 \times 10^3$ | $0.9 \times 10^3$ | $1.3 \times 10^3$ | $1.1 \pm 0.3$ | 0.3 |

TABLE 9

Dose-mortality response of neonate *Heliocoverpa zea* larvae infected per os with wild-type HzSNPV and various recombinants. Bioassay #2.

| Virus | LC50 (PIB/ml) | 95% Fiducial Limit lower | 95% Fiducial Limit upper | Slope | Hetero-geneity |
|---|---|---|---|---|---|
| HzSNPV Elkar | $1.4 \times 10^3$ | $0.9 \times 10^3$ | $1.9 \times 10^3$ | $2.2 \pm 0.5$ | 0.04 |
| HzSNPV (BSU361-) | $1.3 \times 10^3$ | $0.6 \times 10^3$ | $2.0 \times 10^3$ | $1.3 \pm 0.4$ | 0.9 |
| HzEGTde1 | $1.7 \times 10^3$ | $0.8 \times 10^3$ | $2.7 \times 10^3$ | $1.2 \pm 0.2$ | 0.6 |
| HzEGTp6.9tox34 | $1.6 \times 10^3$ | $1.1 \times 10^3$ | $2.5 \times 10^3$ | $1.7 \pm 0.3$ | 0.6 |
| HzEGThsptox34 | $2.3 \times 10^3$ | $1.2 \times 10^3$ | $5.0 \times 10^3$ | $1.9 \pm 0.3$ | 1.2 |
| HzEGTDA26tox34 | $2.1 \times 10^3$ | $1.1 \times 10^3$ | $4.9 \times 10^3$ | $1.9 \pm 0.3$ | 1.1 |

TABLE 10

Time-mortality response of neonate *Heliocoverpa zea* larvae infected per os with wild-type HzSNPV and various recombinant viruses. Bioassay #1.

| Virus | LC50 ET50 ± SE | LC50 Slope ± SE | LC95 ET50 ± SE | LC95 Slope ± SE |
|---|---|---|---|---|
| HzSNPV Elkar | $64.2 \pm 2.8$ | $8.9 \pm 1.9$ | $63.4 \pm 1.8$ | $12.0 \pm 2.0$ |
| HzSNPV (BSU361-) | $61.1 \pm 2.7$ | $10.3 \pm 2.4$ | $64.0 \pm 1.3$ | $16.0 \pm 2.8$ |
| HzEGTde1 | $72.4 \pm 5.2$ | $7.1 \pm 1.9$ | $62.4 \pm 1.6$ | $13.2 \pm 2.4$ |
| HzEGTp6.9tox34 | $43.9 \pm 1.2$ | $19.1 \pm 5.1$ | $40.5 \pm 1.0$ | $13.3 \pm 2.2$ |
| HzEGThsptox34 | $49.5 \pm 1.2$ | $19.2 \pm 4.9$ | $46.4 \pm 0.7$ | $23.5 \pm 4.6$ |
| HzEGTDA26tox34 | $39.3 \pm 1.5$ | $11.5 \pm 2.5$ | $36.8 \pm 0.7$ | $18.2 \pm 3.2$ |

TABLE 11

Time-mortality response of neonate *Heliocoverpa zea* larvae infected per os with wild-type HzSNPV and various recombinant viruses. Bioassay #2.

| Virus | LC50 ET50 ± SE | LC50 Slope ± SE | LC95 ET50 ± SE | LC95 Slope ± SE |
|---|---|---|---|---|
| HzSNPV Elkar | $64.3 \pm 2.8$ | $8.9 \pm 1.7$ | $65.4 \pm 2.2$ | $12.0 \pm 2.0$ |
| HzSNPV (BSU361-) | $62.2 \pm 2.3$ | $11.6 \pm 2.5$ | $58.3 \pm 1.9$ | $10.0 \pm 1.6$ |
| HzEGTdel | $67.3 \pm 3.8$ | $9.6 \pm 2.6$ | $67.3 \pm 2.3$ | $9.5 \pm 1.5$ |
| HzEGTp6.9tox34 | $41.6 \pm 1.2$ | $14.5 \pm 3.0$ | $38.0 \pm 0.7$ | $18.3 \pm 3.1$ |

TABLE 11-continued

Time-mortality response of neonate *Heliocoverpa zea* larvae infected per os with wild-type HzSNPV and various recombinant viruses. Bioassay #2.

| | LC50 | | LC95 | |
|---|---|---|---|---|
| Virus | ET50 ± SE | Slope ± SE | ET50 ± SE | Slope ± SE |
| HzEGThsptox34 | 44.0 ± 0.9 | 20.0 ± 3.9 | 44.1 ± 0.7 | 20.6 ± 3.6 |
| HzEGTDA26tox34 | 39.1 ± 1.5 | 12.0 ± 2.8 | 35.4 ± 0.6 | 19.0 ± 3.9 |

---

We claim:

1. A recombinant DNA molecule comprising a promoter selected from the group consisting of a baculovirus 6.9K promoter, a baculovirus DA26 promoter and a heat shock gene promoter, and a coding sequence for an insect-specific toxin, said coding sequence being operably linked to and expressed under the regulatory control of said promoter provided that when the promoter is a baculovirus DA26 promoter, the sequence for an insect-specific toxin encodes an insect-specific paralytic neurotoxin of a mite of the genus Pyemotes.

2. The recombinant DNA molecule of claim 1 wherein said coding sequence encodes an insect-specific neurotoxin.

3. The recombinant DNA molecule of claim 2 wherein said coding sequence encodes an insect-specific paralytic neurotoxin from a mite of the genus Pyemotes.

4. The recombinant DNA molecule of claim 3 wherein the encoded insect-specific paralytic neurotoxin comprises an amino acid as shown in SEQ ID NO:4.

5. The recombinant DNA molecule of claim 3 wherein the encoded insect-specific paralytic neurotoxin comprises an amino acid sequence as shown in amino acids 1–252 of NO:2.

6. A baculovirus genetically engineered to contain a promoter selected from the group consisting of baculovirus 6.9K, baculovirus DA26 and a heat shock gene promoter and a coding sequence for an insect-specific toxin, said coding sequence being expressed under the regulatory control of said promoter provided that when the promoter is a baculovirus DA26 promoter, the sequence for an insect-specific toxin encodes an insect-specific paralytic neurotoxin of a mite of the genus Pyemotes.

7. The baculovirus of claim 6 wherein said coding sequence encodes an insect-specific paralytic neurotoxin of a mite of the genus Pyemotes.

8. The baculovirus of claim 7 wherein the encoded insect-specific paralytic neurotoxin comprises an amino acid sequence as shown in aminos acids 1–252 of NO:2.

9. The baculovirus of claim 7 wherein the encoded insect-specific paralytic neurotoxin comprises an amino acid sequence as shown in SEQ ID NO:4.

10. The baculovirus of claim 6 wherein said baculovirus is a nucleopolyhedrovirus.

11. The baculovirus of claim 10 wherein said nucleopolyhedrovirus is *Autographa californica* Nuclear Polyhedrosis Virus (AcMNPV).

12. The baculovirus of claim 11 which is v6.9-Tox34 or vDA26-Tox34.

13. The baculovirus of claim 10 wherein said nucleopolyhedrovirus is *Helicoverpa zea* Single Nuclear Polyhedrosis Virus (HzSNPV).

14. The baculovirus of claim 13 wherein said coding sequence encodes an insect-specific paralytic neurotoxin of a mite of the genus Pyemotes.

15. The baculovirus of claim 14 wherein the encoded insect-specific paralytic neurotoxin comprises an amino acid sequence as shown in amino acids 1–252 NO:2.

16. The baculovirus of claim 14 wherein the encoded insect-specific paralytic neurotoxin comprises an amino acid sequence as shown in SEQ ID NO:4.

17. The baculovirus of claim 15 which is vHzDA26tox34, vHSP70tox34, vHzEGTHSP70tox34, vHz6.9tox34, and vHzEGT6.9tox34, vHzHSP70tox34 or vHzEGTDA26tox34.

18. The baculovirus of claim 6 wherein said heat shock promoter is a *Drosophila melanogaster* hsp70 promoter.

19. The baculovirus of claim 18 which is vHSP70tox34.

20. The baculovirus of claim 6 in which a gene encoding an ecdysteroid UDP-glucosyl transferase has been inactivated.

21. A method for the control of insect pests comprising the step of applying the insect-toxic composition of claim 20 to a habitat of said insect pests.

22. The method of claim 21 wherein the baculovirus is v6.9Ktox34.

23. The method of claim 21 wherein the baculovirus is vHzEGT6.9tox34.

24. The method claim 21 wherein the baculovirus is vHzEGTHSP70tox34.

25. The method of claim 21 wherein the baculovirus is vHzDA26tox34.

26. The method of claim 21 wherein the baculovirus is vHSP70tox34.

27. An insect toxic composition comprising an amount of a baculovirus of claim 6 effective for causing a toxic effect on a target insect, and further comprising an agriculturally acceptable carrier.

* * * * *

UNITED STATES PATENT AND TRADEMARK OFFICE
CERTIFICATE OF CORRECTION

PATENT NO. : 6,235,278 B1
DATED : May 22, 2001
INVENTOR(S) : Miller et al.

It is certified that error appears in the above-identified patent and that said Letters Patent is hereby corrected as shown below:

Under Other Publications

In the first O'Reilly reference, delete volumn no "5" and replace with -- 25 --.

In the Popham reference, before "(1997)" insert -- *Biological Control* --.

In the second Thiem reference, delete "(1996)" and replace with -- (1989) --.

In the first Todd reference, delete "(1995) 8(4)" and replace with -- (1996) 70(4) --.

Note

Column 3,
Line 45, between "expressed" and "the" insert -- under --.
Line 61, delete "shaded" and replace with -- bolded --.

Column 4,
Line 2, delete "A" and replace with --Fig. 1A --.
Line 56, delete "Sse8387-T" and replace with -- Sse8387-I --.

Column 5,
Line 24, delete "11B presents" and replace with --11B-11C present --.
Line 26, at the end delete "(SEQ ID NO:24)".
Line 27, at the beginning delete "(SEQ ID NO:24)".
Line 39, delete "OPMNPV" and replace with --OpMNPV --.
Line 43, delete "LOGV" and replace with -- LoGV --.

Column 7,
Line 35, delete preocculuded" and replace with --proccluded --.
Line 53, between "sequence" and "the" insert -- in --.

Note

Column 11,
Line 5, between "expression" and heterologous" insert -- of --.
Line 8, delete "35".

UNITED STATES PATENT AND TRADEMARK OFFICE
CERTIFICATE OF CORRECTION

PATENT NO. : 6,235,278 B1
DATED : May 22, 2001
INVENTOR(S) : Miller et al.

It is certified that error appears in the above-identified patent and that said Letters Patent is hereby corrected as shown below:

Column 12,
Line 22, delete "22:313-3201" and replace with -- 22:313-320].
Line 54, delete "FIG. 11" and replace with -- FIG. 11A --.

Column 15,
Line 29, delete "be" and replace with -- been --.
Line 41, delete "vsp-tox21A" and replace with --vSp-tox21A --.

Column 16,
Line 62, delete "45k" and replace with -- 45% --.

Column 22,
Line 45, delete "10545-549" and replace with -- 10:545-549 --.

Column 25,
Line 16, delete "Visat" and replace with -- ViStat --.

Column 27,
Line 22, delete "reported" and replace with -- reporter --.
Line 51, underline the "C" of the sequence "CAA"; i.e. -- CAA --.

Column 29,
Line 18, delete "VEV" and replace with -- vEV --.
Line 37, delete "VEV" and replace with -- vEV --."

UNITED STATES PATENT AND TRADEMARK OFFICE
CERTIFICATE OF CORRECTION

PATENT NO. : 6,235,278 B1
DATED : May 22, 2001
INVENTOR(S) : Miller et al.

It is certified that error appears in the above-identified patent and that said Letters Patent is hereby corrected as shown below:

Column 30,
Line 30, (Table 1), underline "*scolyti* group"; I.e. -- *scolyti* group --.

Note

Column 80, claim 5,
Line 52, before "NO:2" insert -- SEQ ID --.

Column 80, claim 8,
Line 67, before "NO:2" insert -- SEQ ID --.

Column 81, claim 15,
Line 19, before "NO:2" insert -- SEQ ID --.

Signed and Sealed this

Fourth Day of December, 2001

Attest:

Nicholas P. Godici

NICHOLAS P. GODICI
*Attesting Officer*   *Acting Director of the United States Patent and Trademark Office*